United States Patent
Epshteyn et al.

(10) Patent No.: US 12,415,021 B2
(45) Date of Patent: Sep. 16, 2025

(54) EXTRACORPOREAL BLOOD FILTERING MACHINE AND METHODS

(71) Applicant: Nuwellis, Inc., Eden Prairie, MN (US)

(72) Inventors: Vitaliy Gennad'yevich Epshteyn, Maple Grove, MN (US); Steven Daniel Sandoval, Eden Prairie, MN (US); Kalley Francis Berg, Lino Lakes, MN (US); Franz Willems Ulrich, Minneapolis, MN (US)

(73) Assignee: NUWELLIS, INC., Eden Prairie, MN (US)

( * ) Notice: Subject to any disclaimer, the term of this patent is extended or adjusted under 35 U.S.C. 154(b) by 329 days.

(21) Appl. No.: 18/298,860

(22) Filed: Apr. 11, 2023

(65) Prior Publication Data

US 2024/0277931 A1 Aug. 22, 2024

Related U.S. Application Data

(63) Continuation of application No. 18/171,612, filed on Feb. 20, 2023, now Pat. No. 11,865,302.

(51) Int. Cl.
*A61M 1/16* (2006.01)
*A61M 1/14* (2006.01)
(Continued)

(52) U.S. Cl.
CPC .......... *A61M 1/154* (2022.05); *A61M 1/1601* (2014.02); *A61M 1/36224* (2022.05);
(Continued)

(58) Field of Classification Search
CPC .... A61M 1/3413–3493; A61M 1/1601; A61M 1/3451; A61M 1/1643; A61M 1/14;
(Continued)

(56) References Cited

U.S. PATENT DOCUMENTS

| | | | |
|---|---|---|---|
| 4,670,007 | A | 6/1987 | Wheeldon et al. |
| 4,728,433 | A | 3/1988 | Buck et al. |
(Continued)

FOREIGN PATENT DOCUMENTS

| | | |
|---|---|---|
| CN | 108325019 A | 7/2018 |
| CN | 110152086 A | 8/2019 |
(Continued)

OTHER PUBLICATIONS

International Search Report and Written Opinion of the International Application No. PCT/US2023/071577, mailed Nov. 22, 2023, 22 pg.

(Continued)

*Primary Examiner* — Susan S Su
(74) *Attorney, Agent, or Firm* — Fredrikson & Byron, P.A.

(57) ABSTRACT

An extracorporeal blood filtering machine can include a blood circuit, an effluent circuit, and a source fluid circuit and can be controlled by a controller. The extracorporeal blood filtering machine can also include access ports for connecting the source fluid circuit to the blood circuit, as well as blood sensors to detect possible issues with the extracorporeal blood filtering machine. The extracorporeal blood filtering machine can include density sensors and flow sensors that enable it to be more accurate and to operate while being transported. The extracorporeal blood filtering machine can further include a user interface and can display fluid inflow/outflow information. A medical fluid container can automatically empty after being filled. An apparatus for supporting a medical fluid container can include a hanger and an attachment member with the apparatus able to adjust to ensure the medical fluid container remains properly oriented directly under a medical fluid container scale.

17 Claims, 34 Drawing Sheets

(51) Int. Cl.
| | |
|---|---|
| *A61M 1/36* | (2006.01) |
| *A61M 1/10* | (2006.01) |
| *A61M 1/34* | (2006.01) |
| *A61M 5/14* | (2006.01) |
| *A61M 5/165* | (2006.01) |
| *A61M 5/172* | (2006.01) |
| *A61M 60/109* | (2021.01) |
| *A61M 60/268* | (2021.01) |

(52) U.S. Cl.
CPC ............... *A61M 1/10* (2013.01); *A61M 1/14* (2013.01); *A61M 1/155* (2022.05); *A61M 1/1562* (2022.05); *A61M 1/15632* (2022.05); *A61M 1/1566* (2022.05); *A61M 1/16* (2013.01); *A61M 1/1643* (2014.02); *A61M 1/1694* (2013.01); *A61M 1/34* (2013.01); *A61M 1/3403* (2014.02); *A61M 1/341* (2014.02); *A61M 1/3413* (2013.01); *A61M 1/342* (2013.01); *A61M 1/3424* (2014.02); *A61M 1/3427* (2014.02); *A61M 1/3431* (2014.02); *A61M 1/3434* (2014.02); *A61M 1/3437* (2014.02); *A61M 1/3441* (2013.01); *A61M 1/3444* (2014.02); *A61M 1/3451* (2014.02); *A61M 1/3607* (2014.02); *A61M 1/361* (2014.02); *A61M 1/36225* (2022.05); *A61M 1/362262* (2022.05); *A61M 1/362264* (2022.05); *A61M 1/362266* (2022.05); *A61M 1/3624* (2013.01); *A61M 1/3626* (2013.01); *A61M 1/3627* (2013.01); *A61M 1/3639* (2013.01); *A61M 1/3644* (2014.02); *A61M 1/3663* (2013.01); *A61M 1/3672* (2013.01); *A61M 5/1415* (2013.01); *A61M 5/165* (2013.01); *A61M 5/172* (2013.01); *A61M 60/109* (2021.01); *A61M 60/268* (2021.01); *A61M 2202/0042* (2013.01); *A61M 2205/3331* (2013.01); *A61M 2205/3368* (2013.01); *A61M 2205/3379* (2013.01); *A61M 2205/3393* (2013.01); *A61M 2205/50* (2013.01); *A61M 2205/502* (2013.01); *A61M 2205/505* (2013.01); *A61M 2205/82* (2013.01); *A61M 2205/8206* (2013.01); *A61M 2205/8262* (2013.01); *A61M 2230/005* (2013.01)

(58) Field of Classification Search
CPC .... A61M 1/154; A61M 1/155; A61M 1/1562; A61M 1/15632; A61M 1/1566; A61M 1/16; A61M 1/1694; A61M 1/34; A61M 1/3403; A61M 1/341; A61M 1/342; A61M 1/3424; A61M 1/3427; A61M 1/3431; A61M 1/3434; A61M 1/3437; A61M 1/3441; A61M 1/3444; A61M 1/3607; A61M 1/361; A61M 1/36224; A61M 1/36225; A61M 1/362262; A61M 1/362264; A61M 1/362266; A61M 1/3624; A61M 1/3626; A61M 1/3627; A61M 1/3639; A61M 1/3644; A61M 1/3663; A61M 1/3672; A61M 5/1415; A61M 5/165; A61M 5/172; A61M 60/109; A61M 60/268; A61M 2202/0042; A61M 2205/3331; A61M 2205/3379; A61M 2205/3393; A61M 2205/50; A61M 2205/502; A61M 2205/505; A61M 2205/82; A61M 2205/8206; A61M 2205/8262; A61M 2230/005; A61M 2205/3306; A61M 2205/3313; A61M 2205/3368; A61M 2209/082; A61M 1/1603; A61M 1/1692; A61M 2230/207; A61M 1/3455; A61M 1/3465; A61J 1/10
See application file for complete search history.

(56) References Cited

U.S. PATENT DOCUMENTS

| | | |
|---|---|---|
| 4,850,560 A | 7/1989 | Ross |
| 5,211,849 A | 5/1993 | Kitaevich et al. |
| 6,200,485 B1 | 3/2001 | Kitaevich et al. |
| 6,302,864 B1 | 10/2001 | Nowosielski |
| 6,468,241 B1 | 10/2002 | Gelfand et al. |
| 6,585,675 B1 | 7/2003 | O'Mahony et al. |
| 6,685,664 B2 | 2/2004 | Levin et al. |
| 6,695,806 B2 | 2/2004 | Gelfand et al. |
| 6,773,412 B2 | 8/2004 | O'Mahony et al. |
| 6,796,955 B2 | 9/2004 | O'Mahony et al. |
| 6,887,214 B1 | 5/2005 | Levin et al. |
| 6,890,315 B1 | 5/2005 | Levin et al. |
| 6,923,782 B2 | 8/2005 | O'Mahony et al. |
| 6,947,131 B2 | 9/2005 | O'Mahony et al. |
| RE38,869 E | 11/2005 | Polaschegg et al. |
| 7,018,182 B2 | 3/2006 | O'Mahony et al. |
| 7,135,008 B2 | 11/2006 | O'Mahony et al. |
| 7,199,312 B2 | 4/2007 | O'Mahony et al. |
| 7,230,687 B2 | 6/2007 | O'Mahony et al. |
| 7,232,418 B2 | 6/2007 | Neri et al. |
| 7,297,270 B2 | 11/2007 | Bernard et al. |
| 7,303,540 B2 | 12/2007 | O'Mahony et al. |
| 7,311,689 B2 | 12/2007 | Levin et al. |
| 7,314,554 B2 | 1/2008 | Delnevo et al. |
| 7,410,473 B2 | 8/2008 | Levin et al. |
| 7,410,582 B2 | 8/2008 | Bernard et al. |
| 7,462,786 B2 | 12/2008 | O'Mahony et al. |
| 7,547,200 B2 | 6/2009 | O'Mahony et al. |
| 7,585,286 B2 | 9/2009 | O'Mahony et al. |
| 7,647,834 B2 | 1/2010 | O'Mahony et al. |
| 7,727,391 B2 | 6/2010 | Delnevo et al. |
| 7,789,850 B2 | 9/2010 | Roger |
| 7,867,393 B2 | 1/2011 | Duchamp et al. |
| 7,886,611 B2 | 2/2011 | O'Mahony et al. |
| 7,906,737 B2 | 3/2011 | Freydank et al. |
| 7,935,071 B2 | 5/2011 | Levin et al. |
| 8,197,432 B2 | 6/2012 | O'Mahony et al. |
| 8,267,308 B2 | 9/2012 | Devergne et al. |
| 8,267,881 B2 | 9/2012 | O'Mahony et al. |
| 8,361,023 B2 | 1/2013 | Bedingfield |
| 8,459,543 B2 | 6/2013 | Devergne et al. |
| 8,562,822 B2 | 10/2013 | Roger et al. |
| 8,562,823 B2 | 10/2013 | Roger et al. |
| 8,603,021 B2 | 12/2013 | Evin et al. |
| 8,608,953 B2 | 12/2013 | Brotherton et al. |
| 8,702,638 B2 | 4/2014 | O'Mahony et al. |
| 9,089,639 B2 | 7/2015 | Breuel et al. |
| 9,138,526 B2 | 9/2015 | Ware et al. |
| 9,999,716 B2 | 6/2018 | Golarits et al. |
| 10,549,023 B2 | 2/2020 | Updyke et al. |
| 10,603,423 B2 | 3/2020 | Childers et al. |
| 10,695,481 B2 | 6/2020 | Kelly et al. |
| 10,881,347 B2 | 1/2021 | Barrett et al. |
| 10,987,461 B2 | 4/2021 | Brugger et al. |
| 11,105,669 B2 | 8/2021 | Evans et al. |
| 11,273,246 B2 | 3/2022 | Plahey |
| 11,351,291 B2 | 6/2022 | Kreymann et al. |
| 11,386,994 B2 | 7/2022 | Handler |
| 11,524,101 B2 | 12/2022 | Golarits et al. |
| 2005/0251086 A1 | 11/2005 | Sternby |
| 2005/0284815 A1* | 12/2005 | Sparks ............... G01F 1/8445 |
| | | 604/4.01 |
| 2007/0031976 A1 | 2/2007 | Trouilly et al. |
| 2007/0265594 A1 | 11/2007 | Hagermark et al. |
| 2008/0004594 A1 | 1/2008 | Pahlberg et al. |
| 2008/0015487 A1* | 1/2008 | Szamosfalvi ....... A61M 1/3413 |
| | | 210/323.1 |
| 2010/0022934 A1 | 1/2010 | Hogard |
| 2010/0038317 A1 | 2/2010 | Bissler et al. |
| 2010/0089806 A1 | 4/2010 | Peters et al. |

(56) References Cited

U.S. PATENT DOCUMENTS

| | | |
|---|---|---|
| 2010/0121246 A1 | 5/2010 | Peters et al. |
| 2010/0264086 A1 | 10/2010 | Noack et al. |
| 2011/0056897 A1 | 3/2011 | Kao |
| 2011/0189048 A1 | 8/2011 | Curtis et al. |
| 2013/0012861 A1 | 1/2013 | Zhang |
| 2013/0199998 A1 | 8/2013 | Kelly et al. |
| 2015/0238676 A1 | 8/2015 | Giordano et al. |
| 2016/0287779 A1 | 10/2016 | Orczy-Timko et al. |
| 2016/0354528 A1 | 12/2016 | Pouchoulin |
| 2018/0361046 A1 | 12/2018 | Moretti et al. |
| 2020/0353140 A1 | 11/2020 | Beden et al. |
| 2021/0030937 A1 | 2/2021 | Kelly et al. |
| 2021/0030938 A1 | 2/2021 | Kopperschmidt et al. |
| 2021/0046235 A1 | 2/2021 | Klewinghaus |
| 2021/0113753 A1 | 4/2021 | Moghaddam |
| 2021/0128806 A1 | 5/2021 | Mitrovic et al. |
| 2021/0128812 A1 | 5/2021 | Desouza et al. |
| 2021/0170084 A1 | 6/2021 | Zacharia et al. |
| 2021/0196880 A1 | 7/2021 | O'Mahony et al. |
| 2022/0054724 A1 | 2/2022 | Askenazi et al. |
| 2022/0080091 A1 | 3/2022 | Plahey |
| 2022/0080093 A1 | 3/2022 | Kogan |
| 2022/0211926 A1 | 7/2022 | Childers et al. |
| 2022/0241477 A1 | 8/2022 | Gura |

FOREIGN PATENT DOCUMENTS

| | | |
|---|---|---|
| EP | 611227 A1 | 8/1994 |
| WO | 2004069299 A2 | 8/2004 |
| WO | 20090146913 A2 | 12/2009 |
| WO | 2020132686 A1 | 6/2020 |
| WO | 2021089689 A1 | 5/2021 |
| WO | 2021089690 A1 | 5/2021 |
| WO | 2021094294 A1 | 5/2021 |
| WO | 2021094357 A1 | 5/2021 |
| WO | 2021094446 A1 | 5/2021 |
| WO | 2021219792 A1 | 11/2021 |
| WO | 2022096389 A1 | 5/2022 |
| WO | 2022167394 A1 | 8/2022 |
| WO | 2022171728 A1 | 8/2022 |

OTHER PUBLICATIONS

Prismax Manual (Baxter) https://usrenalacute.baxter.com/sites/g/files/ebysai3231/files/2020-12/Prismax%20Operator%627s%20Manual.pdf Dated Jun. 2019.

Medtronic "Small Patients. Small Solutions. Big Results. Carpediem cardio-renal pediatric dialysis emergency machine", Brochure dated Aug. 2021, 9 pgs.

Medtronic "Technical Data Sheet BL 250 complete kit for hemofiltration/hemodialysis 015 and 0258 with the CARPEDIEM cardio-renal pediatric dialysis emergency machine", dated Jun. 2021, 4 pgs.

* cited by examiner

EXTRACORPOREAL BLOOD FILTERING MACHINE AND METHODS

The present application is a continuation of U.S. Non-Provisional patent application Ser. No. 18/171,612, filed Feb. 20, 2023, the entirety of which is incorporated herein by reference.

GOVERNMENT LICENSE RIGHTS

Inventions disclosed herein were made with government support under 1R44DK127631-01A1 awarded by the National Institute of Diabetes and Digestive and Kidney Diseases. The government has certain rights in such inventions.

BACKGROUND

People whose kidneys are not functioning properly (e.g., are failing) may be treated with renal replacement therapy. Renal replacement therapy replaces the normal blood-filtering function of the kidneys and can include multiple different therapies. Examples include dialysis and hemofiltration. Currently, there are many types of renal replacement therapy machines that can perform one of the therapies and some types of renal replacement therapy machines that can perform more than one of the therapies, albeit by making difficult adjustments. Generally, renal replacement therapy machines use a semi-permeable membrane (e.g., filter) when operating to filter a patient's blood. Renal replacement therapy can be continuous or intermittent, with both having advantages and disadvantages. Some example continuous renal replacement therapies include continuous renal replacement therapy, continuous hemodialysis, continuous hemofiltration, and continuous hemodiafiltration. Some intermittent renal replacement therapies include intermittent renal replacement therapy, intermittent hemodialysis, intermittent hemofiltration, and intermittent hemodiafiltration.

Current renal replacement machines may have issues with accuracy, case of use, adaptability (e.g., ability to perform more than one therapy), safety, and transportability due to a variety of factors. For example, it can be difficult for a patient connected to a renal replacement machine to move around due to the continuous renal replacement machine receiving power from the wall, and the continuous renal replacement machine may lack accuracy while in transport. In another example, renal replacement machines may not be able to differentiate a blood leak from another condition (e.g., hemolysis) that can present safety concerns. It can also be difficult for a user to operate a renal replacement machine. For example, many current renal replacement machines require a user to remove and replace an effluent bag when it is full. Further, apparatuses that hang medical fluid bags used with renal replacement machines may cause accuracy issues. For example, the accuracy of determining a quantity of effluent removed from a patient's blood by a renal replacement machine may be decreased due to tilting of an effluent bag relative to the machine caused by the hanging apparatus.

SUMMARY

The present disclosure generally relates to extracorporeal blood filtering machines and associated methods. Embodiments disclosed herein can relate to extracorporeal blood filtering machines that include various components, including components of a blood circuit, an effluent circuit, and a source fluid circuit. The embodiments can also include components such as sensors, access ports, user inputs, and controllers.

The extracorporeal blood filtering machine, including its various components and its operation, can provide several advantages over existing renal replacement machines. For example, the extracorporeal blood filtering machine can increase safety using sensors, providing alerts, and ensuring an ability to end therapy if needed. In some examples, the extracorporeal blood filtering machine can increase accuracy using different sensors, enable multiple therapies to be used, and enable transportation of the extracorporeal blood filtering machine while still providing therapy.

Embodiments disclosed herein can also include improvements to medical fluid containers, as well as improvements for supporting the medical fluid containers. For instance, a medical fluid container can be automatically emptied, while supports for medical fluid containers can increase accuracy by ensuring the medical fluid containers are correctly supported for related measurements.

Examples provided herein include an apparatus with a bracket and a hanger configured to connect a medical fluid container to an extracorporeal blood filtering machine, a self-emptying medical fluid container, a method of operating an extracorporeal blood filtering machine in transport mode, techniques for calculating fluid flow quantities using determined (not assumed) fluid density values, selecting a single position for connecting a source fluid line to a blood circuit, displaying quantities of fluid flowing into and out of a patient, a method that enables selection of open-loop or closed-loop control, adjusting operation of a clamp based on temperature, and techniques for monitoring hemolysis. These examples can be combined in various ways to achieve synergistic advantages. For example, the apparatus with the bracket and hanger configured to connect the medical fluid container to the extracorporeal blood filtering machine may be combined with the self-emptying medical fluid container to enable further simplified handling of medical fluid containers. In another example, the method of operating the extracorporeal blood filtering machine in transport mode may be combined with the method that enables selection of open-loop or closed-loop control to facilitate open-loop control of the extracorporeal blood filtering machine while in transport mode and closed-loop control of the extracorporeal blood filtering machine while not in transport mode. In another example, selecting a single position for connecting the source fluid line to the blood circuit may be combined with techniques for calculating fluid flow quantities using determined (not assumed) fluid density values in that priming a single source fluid line can prepare the extracorporeal blood filtering machine for operation and also provide a foundation for determining the source fluid density value. These examples are merely illustrative. Other combinations may be made to achieve additional synergistic advantages.

BRIEF DESCRIPTION OF DRAWINGS

The following drawings are illustrative of particular embodiments of the invention and therefore do not limit the scope of the invention. The drawings are not necessarily to scale (unless so stated) and are intended for use with the explanations in the following detailed description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing various embodiments of the present invention. Those skilled in the art will recognize that many of the noted examples have a variety of suitable alternatives.

Figure 1:
FIG. 1 is a perspective view of an example extracorporeal blood filtering system including an extracorporeal blood filtering machine according to an aspect of the present disclosure.

FIG. 1 is a perspective view of an example extracorporeal blood filtering machine 100 according to an aspect of the present disclosure. The extracorporeal blood filtering machine 100 is generally configured to receive blood from a connected patient, filter the blood, and return the filtered blood to the patient. The extracorporeal blood filtering machine 100 can include a variety of components to perform such an operation and can also include components that improve the overall therapeutic effectiveness.

In some embodiments, the extracorporeal blood filtering machine 100 includes components that enable a source fluid line to be connected to different positions and that facilitate the extracorporeal blood filtering machine 100 to operate in different filtering modes. In some embodiments, the extracorporeal blood filtering machine 100 includes components that can help alert a user that the extracorporeal blood filtering machine 100 has a fault, such as a blood leak. In some embodiments, the extracorporeal blood filtering machine 100 includes components that help prevent serious issues, such as a gas embolism, from affecting the patient. In some embodiments, the extracorporeal blood filtering machine 100 includes components that increase the accuracy of fluid removal/addition during blood filtering.

As illustrated, the extracorporeal blood filtering machine can hold medical fluid containers, which can be part of the extracorporeal blood filtering machine. In some embodiments, the mechanism for holding the medical fluid containers is improved. In some embodiments, a medical fluid container has an improved design.

In some embodiments, the extracorporeal blood filtering machine 100 includes components that enable the extracorporeal blood filtering machine 100 to operate under closed-loop control as well as operate under open-loop control. In some embodiments, the extracorporeal blood filtering machine 100 includes components that enable the extracorporeal blood filtering machine 100 to operate on wall power or battery power and easily switch between the power sources while maintaining accuracy. In some embodiments, the extracorpcrcal blood filtering machine 100 includes components that enable a user to accurately determine fluid inflow, fluid outflow, and a fluid balance of a patient connected to the extracorporeal blood filtering machine.

The above embodiments and others are illustrated and described in detail throughout the entirety of this disclosure.

Figure 2:
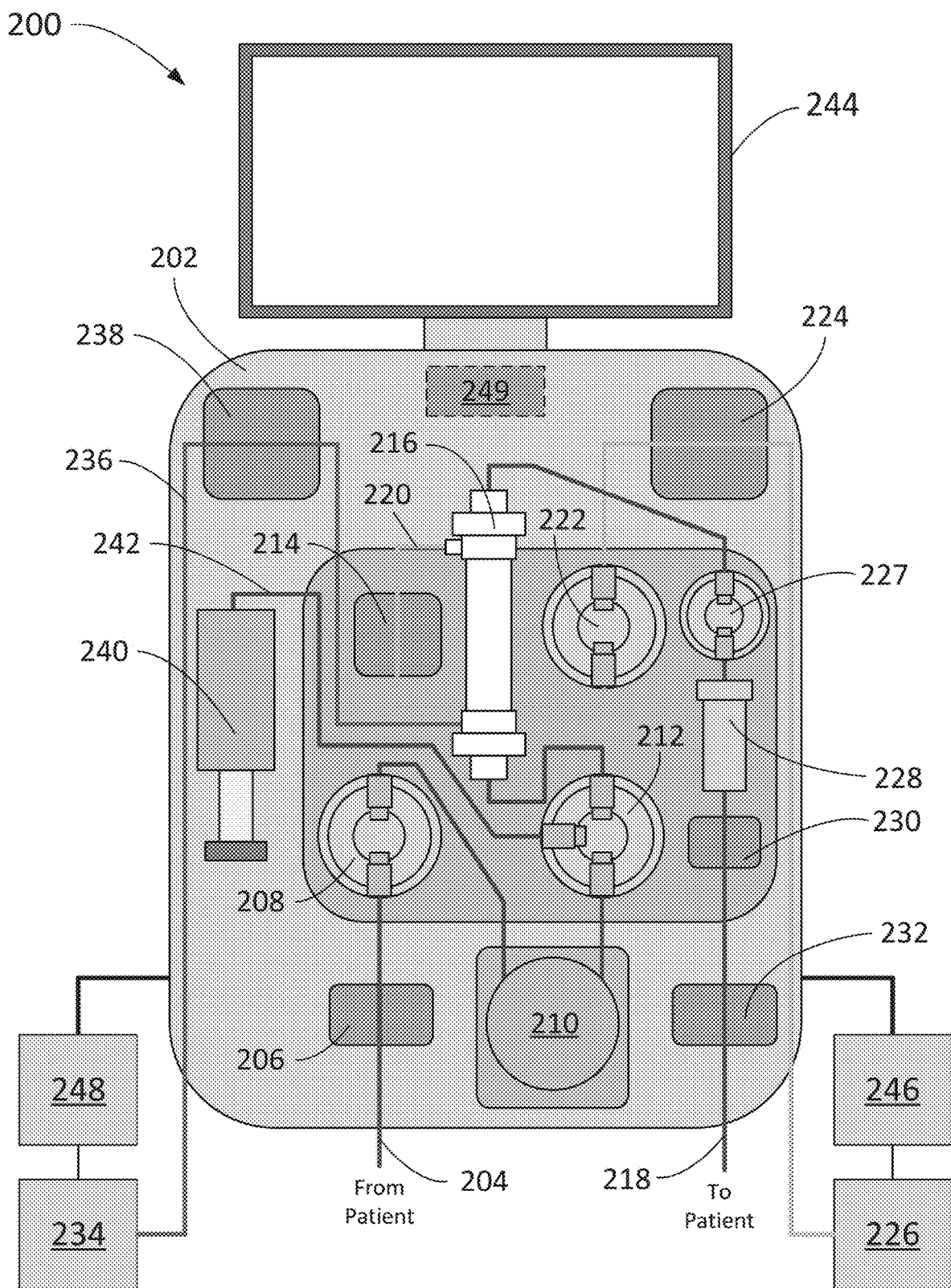
FIG. 2 is a diagrammatic view of an example extracorporeal blood filtering machine according to an aspect of the present disclosure.

Moving to FIG. 2, FIG. 2 is a diagrammatic of an example extracorporcal blood filtering machine 200 according to an aspect of the present disclosure. While the extracorporcal blood filtering machine 200 can be configured to perform various operations and incorporate various sensors, pumps, displays, and other devices, in general, the extracorporeal blood filtering machine 200 filters a patient's blood while it is outside of the patient.

To filter a patient's blood, the extracorporeal blood filtering machine 200 includes a blood circuit. The blood circuit comprises a blood line including a blood inlet 204 configured to receive blood from a patient and a blood outlet 218 configured to return the blood to the patient. The blood circuit also includes a filter 216 fluidly connected to the blood line between the blood inlet 204 and the blood outlet 218 which is configured to remove waste from blood passing through it. For components that are fluidly connected to one another, fluid can pass from one of the components to the other (e.g., blood from the blood line passes through the filter 216). The blood circuit further includes a blood pump 210 that is configured to pump the blood from the blood inlet 204 to the blood outlet 218 through the filter 216. In operation of the blood circuit, the blood pump 210 pumps blood from the patient, through the filter 216, and back into the patient.

In filtering the patient's blood, waste products are generated in the form of effluent. Accordingly, the extracorporeal blood filtering machine 200 includes an effluent circuit to remove any effluent from the filter 216. The effluent circuit includes an effluent line 220 fluidly connected to the filter 216 with the effluent line 220 configured to receive waste from the filter 216 in the form of effluent. The effluent circuit also includes an effluent pump 224 configured to pump the effluent from the filter 216, through the effluent line 220, and into an effluent receptacle 226. The effluent receptacle 226 of FIG. 2 takes the form of an effluent fluid bag, though other receptacles can be used. In some examples, the effluent circuit or parts thereof (e.g., effluent pump 224) are optional to the extracorporeal blood filtering machine 200 or are present but not used.

In some examples, it can be advantageous to know how much effluent has been filtered from the blood of a patient, such as to determine the patient's fluid balance of fluid inflow vs. fluid outflow. In some such examples, the extracorporeal blood filtering machine 200 can include an effluent scale 246. The effluent scale 246 is configured to dynamically weigh the effluent within the effluent receptacle 226. In some examples, the effluent scale can take the form of one or more load cells, though other types of effluent scales can be used. In some embodiments, the effluent scale 246 is in communication with the effluent pump 224 and can affect the rate at which the effluent pump 224 pumps effluent. Such configurations can help change or maintain a desired rate of effluent fluid that is removed from a patient's blood.

In some configurations of the extracorporeal blood filtering machine 200, external fluid is added to the patient's blood. For example, source fluid, such as dialysate replacement fluid or electrolyte fluid can be added into the patient's blood and can replace effluent that is filtered out from the blood to achieve fluid balance within the patient. Additionally or alternatively, the source fluid can include general nutritional injection fluid comprising nutrients for a patient. In the embodiment of FIG. 2, the extracorporeal blood filtering machine 200 includes a source fluid circuit which adds a source fluid to the patient's blood. The source fluid circuit includes a source fluid line 236 fluidly connected to a source fluid reservoir 234 which is configured to be connected to a single selected position in the blood circuit. The single selected position of the source fluid line can be selected from multiple potential positions, which is discussed further elsewhere herein. In FIG. 2, the source fluid line is fluidly connected at the filter 216. The source fluid circuit also includes a source fluid pump 238, which is configured to pump source fluid from the source fluid reservoir 234 through the source fluid line 236 and into the blood circuit.

In similarity with the effluent circuit, in some examples, it can be advantageous to know how much source fluid has been added into the blood of a patient such as to determine the patient's fluid balance of fluid inflow vs. fluid outflow. In some such examples, the extracorporeal blood filtering machine 200 can include a source fluid scale 248. The source fluid scale 248 is configured to dynamically weigh the source fluid within the source fluid reservoir 234. In some examples, the source fluid scale can take the form of one or more load cells, though other types of source fluid scales can be used. In some embodiments, the source fluid scale 248 is in communication with the source fluid pump 238 and can affect the rate at which the source fluid pump 238 pumps source fluid. Such configurations can help change or maintain a desired amount of source fluid that is added to a patient's blood.

In embodiments that include both a source fluid scale 248 and an effluent scale 246, the source fluid scale 248 and the effluent scale 246, along with the source fluid pump 238 and the effluent pump 224, can be used together. For example, the source fluid scale 248 with the source fluid pump 238 can be configured to add an amount of source fluid to a patient's blood that is similar to, if not the same as, an amount of effluent being removed by the effluent pump 224 and stored in the effluent receptacle 226. The fluid balance of a patient's blood can thus be maintained as the amount of effluent (e.g., fluid) removed from the patient's blood is compensated for by the addition of an approximately equal amount of source fluid. In some examples, a controller is connected to each of the source fluid scale 248, the effluent scale 246, the source fluid pump 238, and the effluent pump 224 to ensure a desired fluid balance in the patient's blood. For instance, the controller can receive weights of the source fluid and the effluent via the source fluid scale 248 and the effluent scale 246 respectively while also receiving the pump speed of both the source fluid pump 238 and the effluent pump 224. The controller can then adjust the source fluid pump 238 and/or the effluent pump 224 to maintain or change a fluid balance within the patient's blood. Additionally or alternatively, in some embodiments, the blood pump 210 can be adjusted based on any one of the source fluid scale 248, the source fluid pump 238, the effluent scale 246, or the effluent pump 224.

Continuing with the embodiment of FIG. 2, the extracorporeal blood filtering machine 200 can include an anticoagulant source 240 fluidly connected to the blood line between the blood inlet 204 and the filter 216 via an anticoagulant line 242. The anticoagulant source 240 is illustrated as a syringe, however other source types can be used. The anticoagulant source 240 can be used to introduce anticoagulant into the blood line before the filter 216 to ensure that blood does not clot within the filter and prevent blood from flowing therethrough. The anticoagulant source 240 can be used to introduce anticoagulant manually or automatically (e.g., via a motor pushing on the syringe plunger) into the blood line. In some examples, the anticoagulant source is connected to the filter directly.

In addition to the fluid lines, pumps, and scales, the extracorporeal blood filtering machine 200 also includes various sensors. For example, between the blood inlet 204 and the blood pump 210, the extracorporeal blood filtering machine 200 includes a hematocrit sensor 206 configured to sample the blood in the blood line to measure a proportion of red blood cells within the patient's blood. In some examples, the hematocrit sensor 206 is configured to output a hematocrit signal, which is indicative of the proportion of red blood cells within a patient's blood.

The extracorporeal blood filtering machine 200 also includes a series of pressure sensors 208, 212, 222, 227 configured to measure a pressure of the fluid within them. The series of pressure sensors 208, 212, 222, 227 can be monitored to verify proper fluid flows within the extracorporeal blood filtering machine 200. A first pressure sensor 208 is part of the blood circuit and is located between the blood inlet 204 and the blood pump 210. A second pressure sensor 212 is also part of the blood circuit and is located between the blood pump 210 and the filter 216. As shown, the anticoagulant line 242 connects to the blood circuit at the second pressure sensor 212. A third pressure sensor 222 is part of the effluent circuit and is located on the effluent line 220 after the filter 216 and before the effluent receptacle 226. Lastly, a fourth pressure sensor 227 is part of the blood circuit and is located after the filter 216 and before the blood outlet 218. While the pressure sensors 208, 212, 222, and 227 are illustrated in specific positions within their respective fluid circuits, the pressure sensors 208, 212, 222, and 227 can be located in different positions. For example, the fourth pressure sensor 227 is illustrated as being before the bubble trap 228 but can be located after the bubble trap 228 in some examples. The pressure sensors 208, 212, 222, and 227 can be any type of pressure sensor including an air pressure sensor.

The extracorporeal blood filtering machine 200 further includes a blood leak detector 214, which is located on the effluent line 220 after the filter 216. The blood leak detector 214 can detect if some amount of a patient's blood has leaked through the filter 216 into the effluent line 220. In some examples, the blood leak detector 214 can output a signal indicating if a threshold of blood is leaking into the effluent line.

Additionally, in the embodiment of FIG. 2, the extracorporeal blood filtering machine 200 includes a bubble trap 228 located between the filter 216 and the blood outlet 218. The bubble trap 228 is fluidly connected to the blood outlet 218 and removes air bubbles present in the blood line. After the bubble trap 228, the extracorporeal blood filtering machine 200 includes a bubble sensor 230 (e.g., air bubble sensor) that detects/identifies if any gas bubbles (e.g., air bubbles) are present in the blood outlet 218 connected to the patient. If the bubble sensor 230 detects any gas bubbles are present in the blood outlet, the bubble sensor 230, or a controller connected thereto, can activate a clamp 232 to clamp the blood outlet 218 and prevent any gas bubbles from flowing into the patient's body. The clamp 232 can stop all flow of blood to the patient to ensure no gas bubbles enter the patient's body. Additionally, if the bubble sensor 230 detects a gas bubble in the blood outlet 218, the bubble sensor, or a controller connected thereto, can stop the blood pump 210, the source fluid pump 238, and/or the effluent pump 224 from pumping to prevent a pressure buildup within the fluid lines of the extracorporeal blood filtering machine 200.

In addition to the sensors and the fluid components, the extracorporeal blood filtering machine 200 can include a display 244. The display 244 can be configured to display information about the extracorporeal blood filtering machine 200 including any data generated by the various sensors and pumps. The display 244 can also be configured to display information about a patient and information that is obtained from another machine (e.g., via electronic communication). In some examples, the display 244 comprises a user interface (e.g., via touch screen).

The extracorporeal blood filtering machine 200 can also include a controller 249. The controller can be in communication (e.g., electric communication) with one or more of the hematocrit sensor 206, the pressure sensors 208, 212, 222, 227 the blood pump 210, the blood leak detector 214, the effluent pump 224, the bubble sensor 230, the clamp 232, the source fluid pump 238, the display 244, the effluent scale 246, and/or the source fluid scale 248. In some examples, the controller 249 is also in communication with the anticoagulant source 240. In general, the controller 249 can receive signals and/or send signals to any one or more of the above listed components and can perform functions related to received and/or sent signals. For example, the controller can receive signals from the various sensors, use those signals in a comparison, and output signals to one or more of the various pumps to adjust operation of one or more of the pumps based on received signals from the various sensors.

Moving to an example operation of FIG. 2, the blood inlet 204 receives blood from a patient with the blood passing through the hematocrit sensor 206. The hematocrit sensor 206 can measure a proportion of red blood cells within the patient's blood. Next, the blood passes through the first pressure sensor 208 which measures the blood pressure in the blood line before the blood is pumped through the blood pump 210. Once pumped through the blood pump 210, the blood passes into the second pressure sensor 212, which measures the blood pressure in the blood line after the blood pump 210. At this same point, anticoagulant can be added from the anticoagulant source 240, through the anticoagulant line 242, and into the blood line before the filter 216.

Next, the blood passes through the filter 216, which removes waste from the blood in the form of effluent. The blood continues through the blood line to the fourth pressure sensor 227, which measures the blood pressure in the blood line after the filter 216. The blood further continues to the bubble trap 228, which removes any air bubbles from the blood line. The blood then passes through the bubble sensor 230, which determines if any gas bubbles are present in the blood line. The blood continues past the clamp 232, which can clamp the blood line for reasons such as gas bubbles present within the blood line and finally returns back to the patient via the blood outlet 218.

While blood moves through the filter 216, effluent removed from the blood by the filter 216 is pumped through the effluent line 220 through the blood leak detector 214 via the effluent pump 224. The blood leak detector can detect if some amount of a patient's blood has leaked into the effluent line 220. Next, the effluent continues to the third pressure sensor 222, which can measure the pressure of the effluent within the effluent line 220. The effluent is then pumped to the effluent receptacle 226, which is attached to the effluent scale 246. The effluent scale 246 can measure the weight of the effluent and can determine the amount of effluent within the effluent receptacle 226.

Further, while blood moves through the filter 216, source fluid can be added to the blood line at the filter 216. The source fluid can be pumped from the source fluid reservoir 234, through the source fluid line 236, to the filter 216 via the source fluid pump 238. The source fluid reservoir 234 is connected to the source fluid scale 248, which can measure the weight of the source fluid pumped into the blood line and can determine the amount of source fluid added to the blood line. Information about the source fluid added, effluent removed, the blood pump speed, and other information about the operation of the extracorporeal blood filtering machine 200 can be displayed in the display 244.

The illustrated embodiment of FIG. 2 is one configuration of an example extracorporcal blood filtering machine 200 that incorporates blood filtering, effluent removal, and source fluid replacement. Some configurations of an extracorporeal blood filtering machine are similar to FIG. 2; however, they incorporate the source fluid into the blood circuit at different locations. Alternatively, some configurations of an extracorporeal blood filtering machine may not include source fluid replacement.

Figure 3:
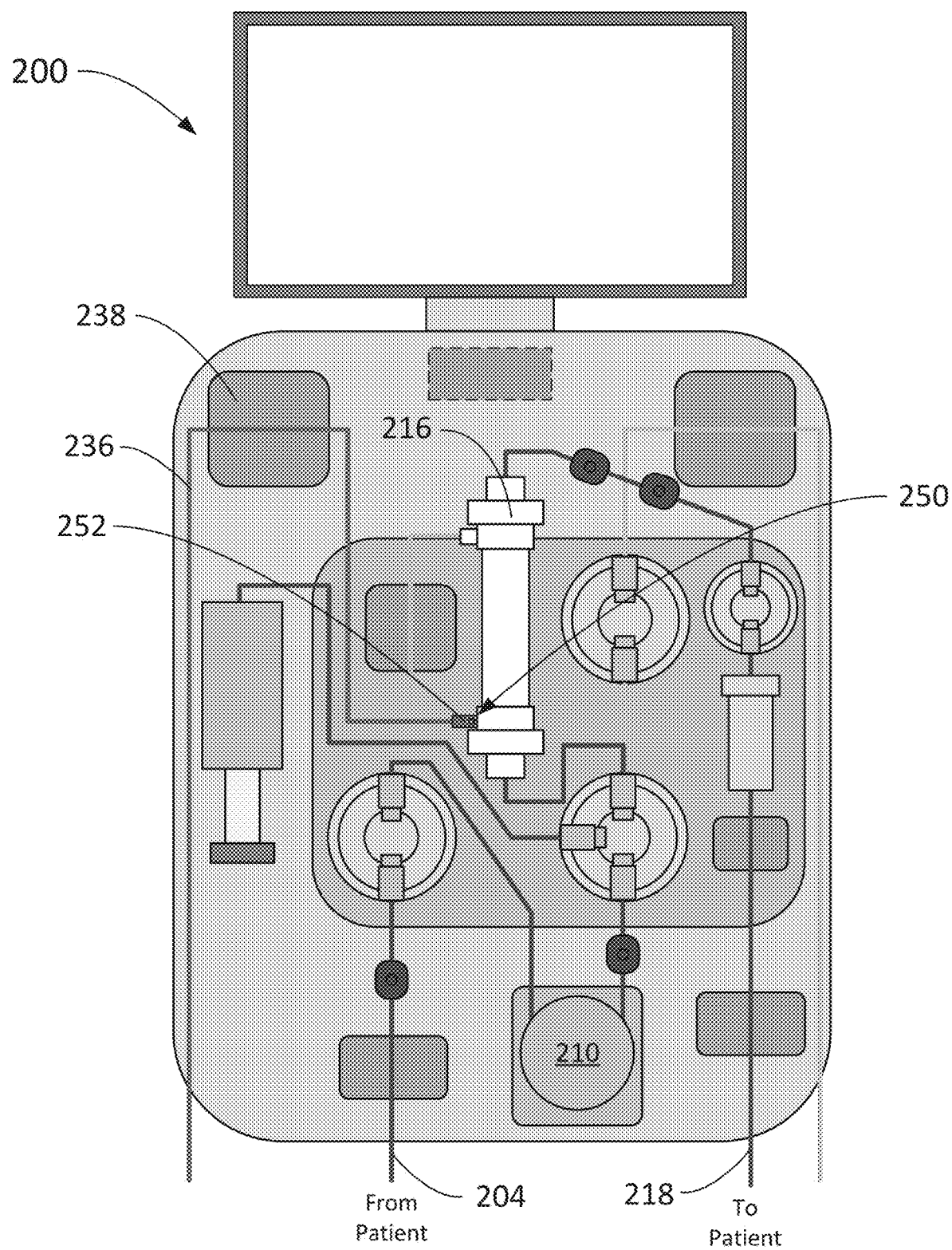
FIG. 3 is a diagrammatic view of the example extracorporeal blood filtering machine of FIG. 2 in one example configuration according to an aspect of the present disclosure.

Moving to FIG. 3, FIG. 3 is a diagrammatic view of the example extracorporcal blood filtering machine 200 of FIG. 2 in one example configuration according to an aspect of the present disclosure. Specifically, the extracorporeal blood filtering machine 200 is in a configuration for performing continuous venovenous hemodialysis. In this configuration, the source fluid line 236 is connected to a first position 250 in the blood circuit, with the first position 250 being at the filter 216. To connect the source fluid line 236 at the first position 250, the extracorporeal blood filtering machine 200 includes an access port 252, which can be referred to as a continuous venovenous hemodialysis access port 252. The continuous venovenous hemodialysis access port 252 facilitates connection of the source fluid line 236 to the filter 216.

In operation of the embodiment of FIG. 3, blood is pumped from the patient through the blood inlet 204 via the blood pump 210. At the same time, source fluid is pumped from a source fluid reservoir (e.g., 234) through the source fluid line 236 via the source fluid pump 238 to the first position 250. At the filter 216, the source fluid is pumped in the same direction to the flow of blood (e.g., co-axially) in the filter 216 with the filter 216 including a highly permeable membrane. The filter 216 filters out waste from the blood in the form of effluent, with the effluent then pumped into an effluent receptacle (e.g., 226) via the effluent pump (e.g., 224). The filtered blood continues through the blood circuit until it returns to the patient via the blood outlet 218. In some examples, the source fluid is pumped in an opposite direction to the flow of blood (e.g., counter-axially) in the filter 216, with the filter 216 including a highly permeable membrane.

Figure 4:
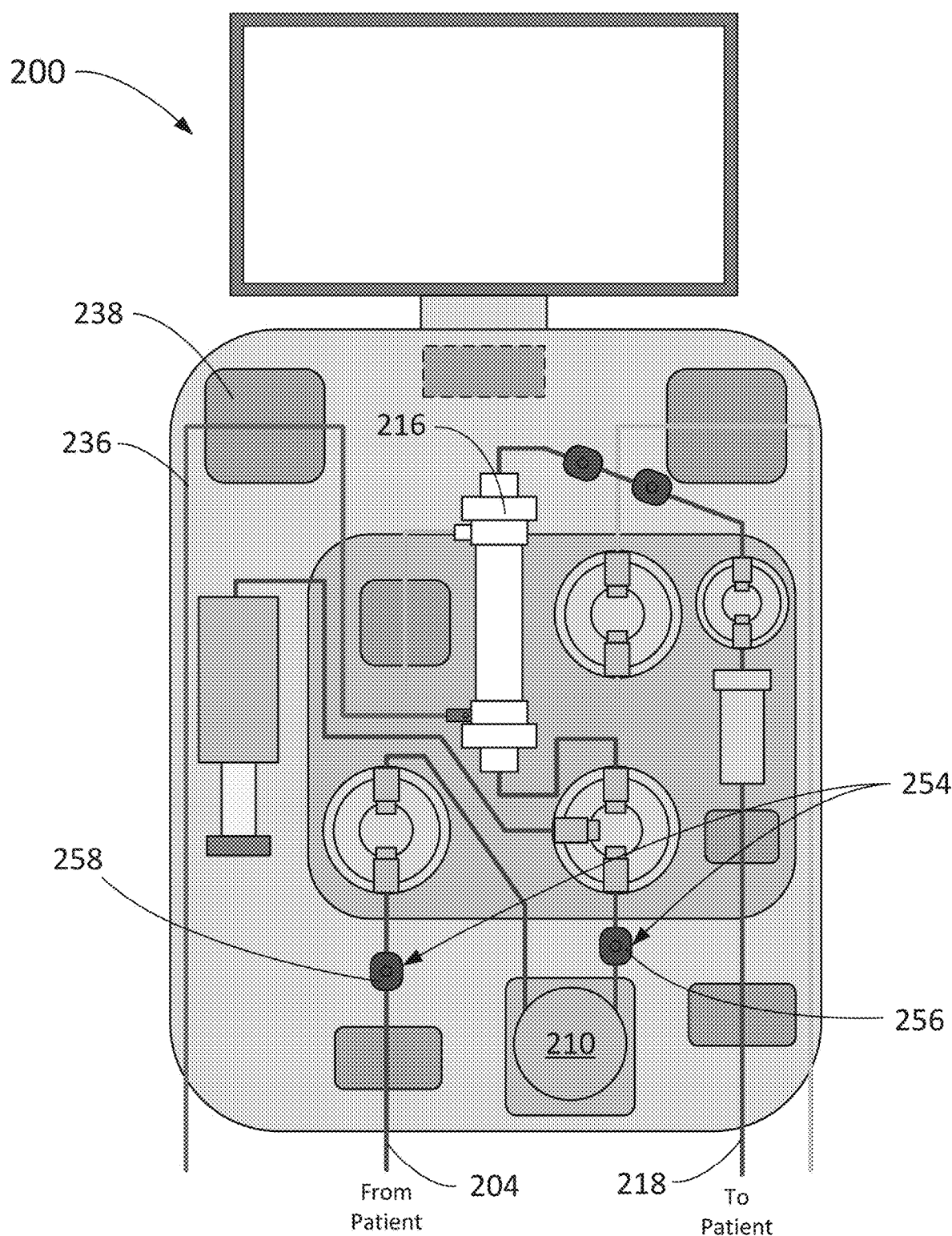
FIG. 4 is a diagrammatic view of the example extracorporeal blood filtering machine of FIG. 2 in an alternate example configuration according to an aspect of the present disclosure.

Moving to FIG. 4, FIG. 4 is a diagrammatic view of the example extracorpoxcal blood filtering machine 200 of FIG. 2 in an alternate example configuration according to an aspect of the present disclosure. Specifically, the extracorporeal blood filtering machine 200 is in a configuration for performing continuous venovenous hemofiltration, with source fluid being added pre-filter. In this configuration, the source fluid line 236 is connected to a second position 254 in the blood circuit, with the second position 254 being between the blood inlet 204 and the filter 216. In some examples, the second position 254 is defined as being between a hematocrit sensor (e.g., 206) and the filter 216. To connect the source fluid line 236 at the second position 254, the extracorporeal blood filtering machine 200 includes access ports 256, 258, which can each be referred to as a first continuous venovenous hemofiltration access port 256, 258. The access ports 256, 258 facilitate connection of the source fluid line 236 to the blood line between the blood inlet 204 and the filter 216.

Both the access ports 256, 258 are located at the second position 254, however, the access port 258 is located before the blood pump 210 while the access port 256 is located after the blood pump 210. The source fluid line 236 can connect to either of the access ports 256, 258 to introduce source fluid to the blood line. In some examples, only one of access port 256 or access port 258 is incorporated into the extracorporeal blood filtering machine 200. Alternatively, in some examples, more than one access port can be included between the blood inlet 204 and the filter 216 (e.g., in the second position 254).

In operation of the embodiment of FIG. 4, blood is pumped from the patient through the blood inlet 204 via the blood pump 210. At the same time, source fluid is pumped from a source fluid reservoir (e.g., 234) through the source fluid line 236 via the source fluid pump 238 to the second position 254. At the second position 254, between the blood inlet 204 and the filter 216, the source fluid is introduced directly into the blood line and combines with the blood. The blood and source fluid combination then continues through the filter 216, with the filter 216 filtering out waste from the blood and source fluid combination in the form of effluent. The effluent is then pumped into an effluent receptacle (e.g., 226) via the effluent pump (e.g., 224). The filtered blood and source fluid combination then continues through the blood circuit until it returns to the patient via the blood outlet 218.

Figure 5:
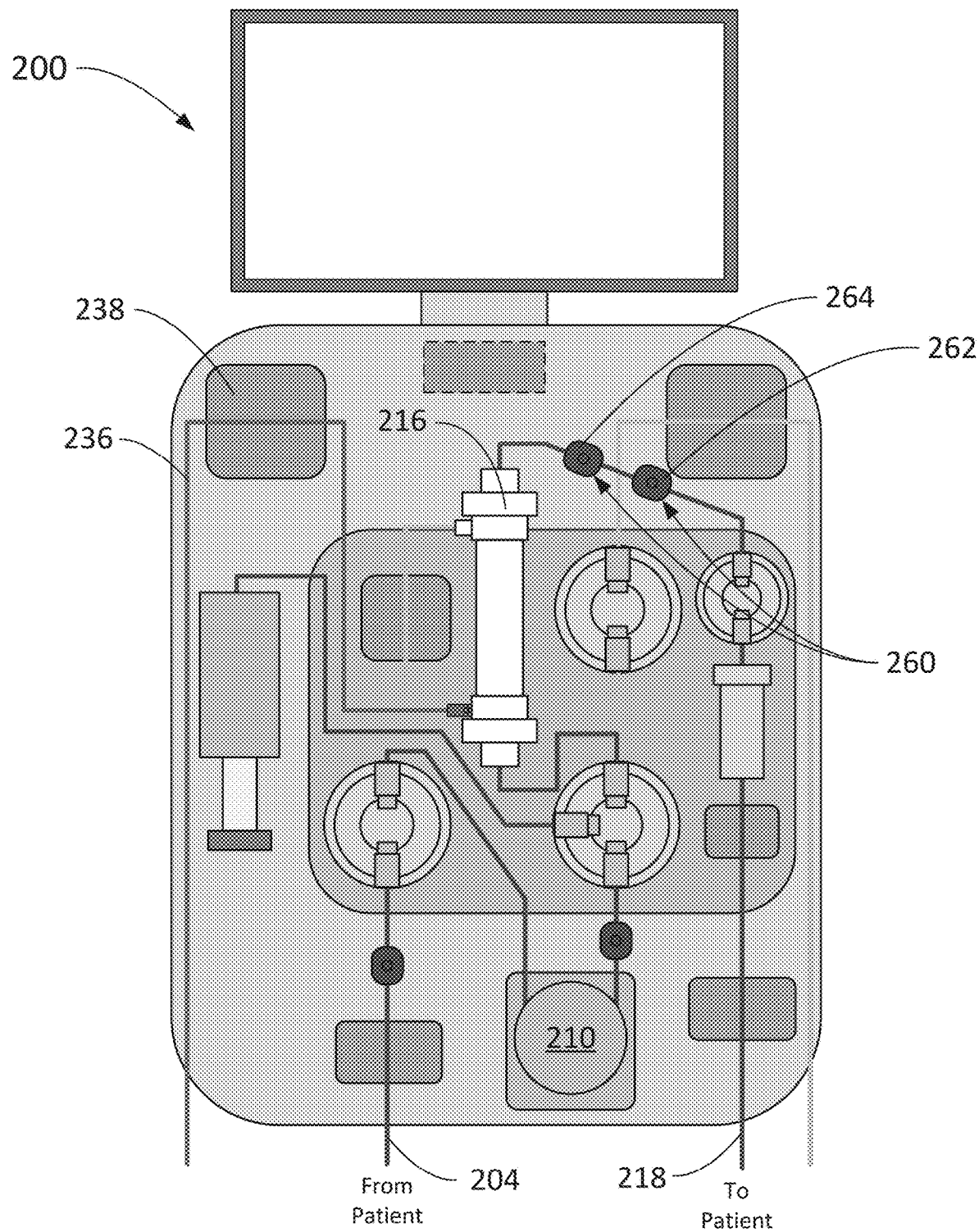
FIG. 5 is a diagrammatic view of the example extracorporeal blood filtering machine of FIG. 2 in an alternate example configuration according to an aspect of the present disclosure.

Moving to FIG. 5, FIG. 5 is a diagrammatic view of the example extracorporeal blood filtering machine 200 of FIG. 2 in an alternate example configuration according to an aspect of the present disclosure. Specifically, the extracorporeal blood filtering machine 200 is in a configuration for performing continuous venovenous hemofiltration with source fluid being added post-filter. In this configuration, the source fluid line 236 is connected to a third position 260 in the blood circuit, with the third position 260 being between the filter 216 and the blood outlet 218. In some examples, the third position 260 is defined as being between the filter 216 and an air bubble sensor (e.g., 230). To connect the source fluid line 236 at the third position 260, the extracorporeal blood filtering machine 200 includes access ports 262, 264, which can each be referred to as a second continuous venovenous hemofiltration access port. The access ports 262, 264 facilitate connection of the source fluid line 236 to the blood line between the filter 216 and the blood outlet 218.

Both the access ports 262, 264 are located at the third position 260, however, the access port 264 is located closer to the filter 216 in the blood line than the access port 262. The source fluid line 236 can connect to either of the access ports 262, 264 to introduce source fluid to the blood line. In some examples, only one of access port 262 or access port 264 is incorporated into the extracorporeal blood filtering machine 200. Alternatively, in some examples, more than one access port can be included between the filter 216 and the blood outlet 218.

In operation of the embodiment of FIG. 5, blood is pumped from the patient through the blood inlet 204 via the blood pump 210 to the filter 216. The blood is then filtered with the filter 216, removing waste from the blood in the form of effluent. The effluent is then pumped into an effluent receptacle (e.g., 226) via the effluent pump (e.g., 224). At the same time, source fluid is pumped from a source fluid reservoir (e.g., 234) through the source fluid line 236 via the source fluid pump 238 to the third position 260. At the third position 260, between the filter 216 and the blood outlet 218, the source fluid is introduced directly into the blood line and combines with blood that has already been filtered by the filter 216. The filtered blood and source fluid combination then continues through the blood circuit until it returns to the patient via the blood outlet 218.

Figure 6:
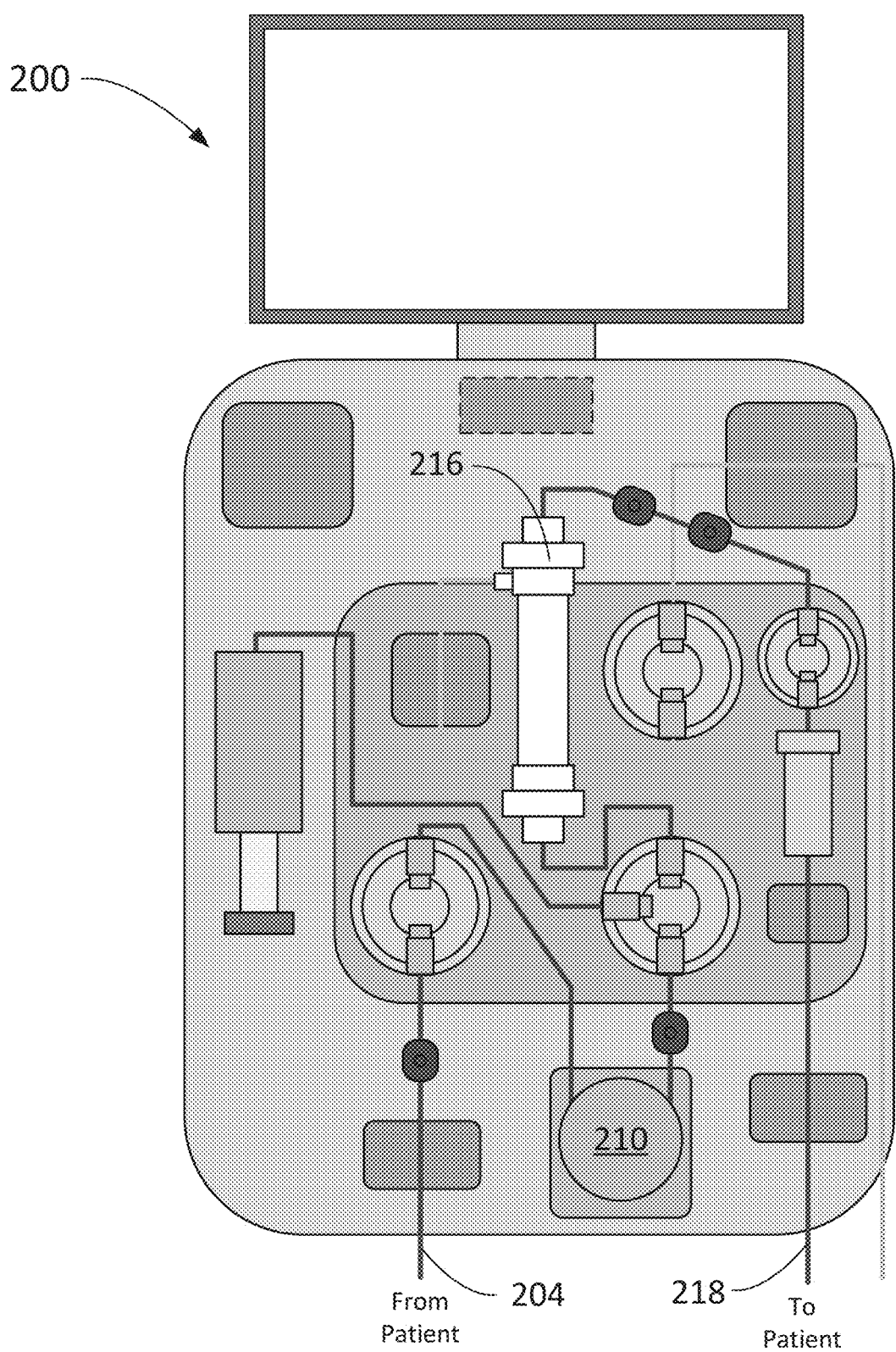
FIG. 6 is a diagrammatic view of the example extracorporeal blood filtering machine of FIG. 2 in an alternate example configuration according to an aspect of the present disclosure.

Moving to FIG. 6, FIG. 6 is a perspective view of the example extracorporeal blood filtering machine 200 of FIG. 2 in an alternate example configuration according to an aspect of the present disclosure. Specifically, the extracorporeal blood filtering machine 200 is in a configuration for performing slow continuous ultrafiltration with no source fluid being added by the extracorporeal blood filtering machine 200. In this configuration, a patient's blood is filtered to remove waste and excess fluid.

In operation of the embodiment of FIG. 6, blood is pumped from the patient through the blood inlet 204 via the blood pump 210 to the filter 216. The blood is then filtered with the filter 216, removing waste from the blood in the form of effluent. The effluent is then pumped into an effluent receptacle (e.g., 226) via the effluent pump (e.g., 224). The filtered blood then continues through the blood circuit until it returns to the patient via the blood outlet 218.

Now referring to the illustrated embodiments of FIGS. 2-6, the extracorporeal blood filtering machine 200 of each of the illustrated embodiments include all the access ports including the continuous venovenous hemodialysis access port 252, the first continuous venovenous hemofiltration access port 256, 258, and the second continuous venovenous hemofiltration access port 262, 264. The continuous venovenous hemodialysis access port 252 can facilitate connection of the source fluid line 236 to the first position 250, which is at the filter 216. The first continuous venovenous hemofiltration access port 256, 258 can facilitate connection of the source fluid line 236 at the second position 254, which is between the blood inlet 204 and the filter 216. The second continuous venovenous hemofiltration access port 260, 262 can facilitate connection of the source fluid line 236 to the third position 260, which is between the filter 216 and the blood outlet 218. Accordingly, the extracorporeal blood filtering machine 200 has a source fluid line 236 that can be connected to a single selected position in the blood circuit, with the single selected position being selected from among multiple potential positions, including the first position 250, the second position 254, the third position 260, and no position (e.g., not connected as in FIG. 6). The ability to connect the source fluid line 236 to any of the selected positions is advantageous as a user can use the extracorporeal blood filtering machine 200 for different therapies that involve supplying source fluid at different points within the blood circuit.

In the illustrated embodiments of FIGS. 2-6, each of the continuous venovenous hemodialysis access port 252, the first continuous venovenous hemofiltration access port 256, 258, and the second continuous venovenous hemofiltration access port 262, 264, can comprise a self-sealing luer. In some examples, all the access ports of the extracorporeal blood filtering machine 200 comprise self-sealing luers. Using self-sealing luers for the access ports can be advantageous as a user can easily connect and disconnect a source fluid line from an access port without needing to clamp the access port to prevent air from entering the line and prevent fluid from leaking.

In some examples, the various access ports can enable a connected source fluid line 236 to be disconnected from a selected position (e.g., a second position 254) and reconnected to a different position (e.g., a third position 260) in the blood circuit while the blood pump 210 and the effluent pump 224 are operating. In some such examples, the access ports comprise self-sealing luers to prevent air from entering the line and prevent fluid leaks.

As discussed with respect to FIG. 2, the extracorporeal blood filtering machine 200 can include a controller 249. In some examples, the controller 249 can be used to ensure that the source fluid line 236 is connected to the selected position rather than to an unselected position. For instance, the controller 249 can be configured to receive a measurement of pressure in the blood line, such as from the pressure sensors 208, 212, and/or 227, during priming of the blood line. The controller 249 can further be configured to compare the received measurement with an expected value associated with a selected position (e.g., a first position 250, at the filter 216). The controller 249 may alert a user if the received pressure measurement is not within a threshold of the expected value as that would indicate an incorrect source fluid line connection to the blood line.

Figure 7:
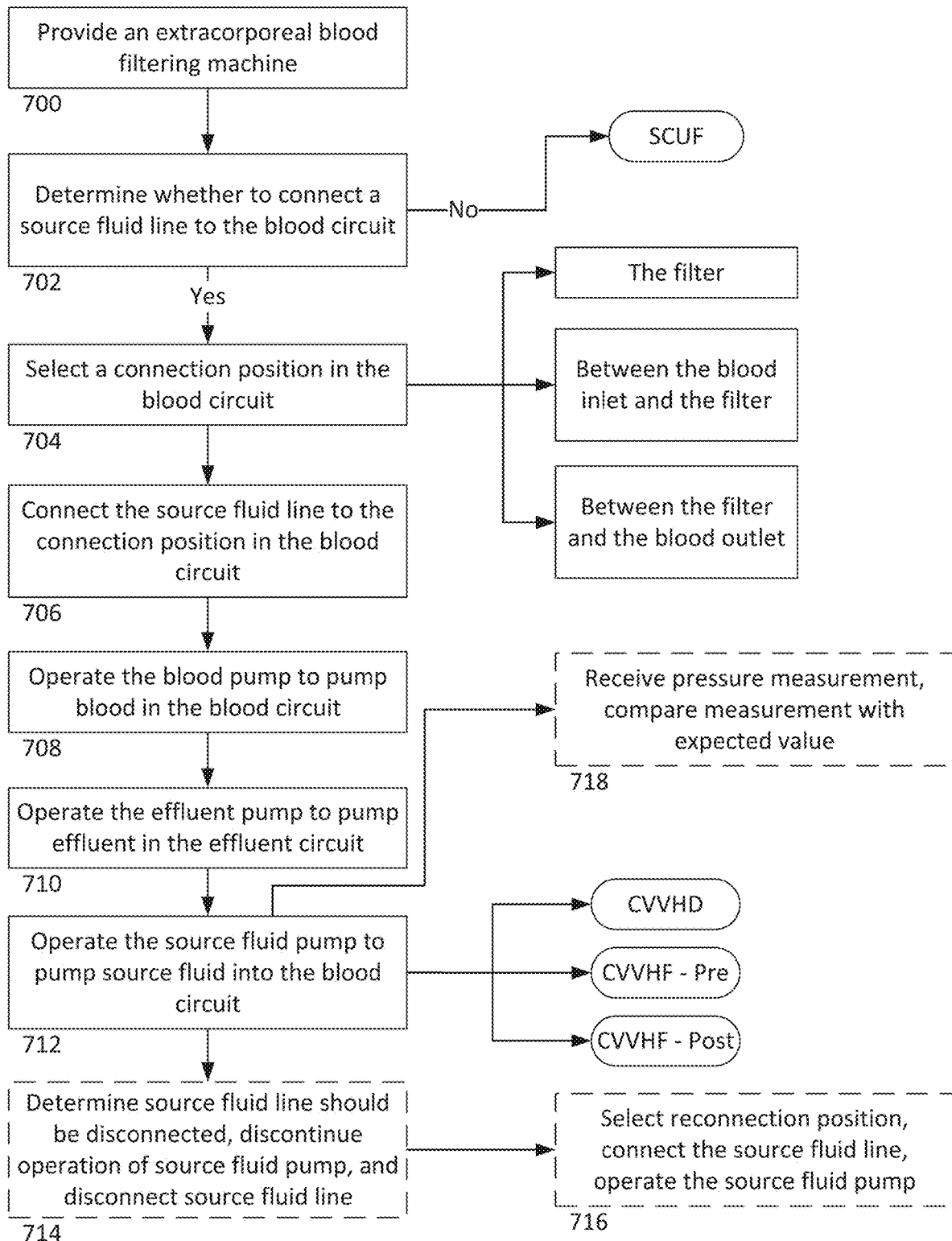
FIG. 7 is a flow chart of an example method related to the illustrated embodiments of FIGS. 2-6, according to an aspect of the present disclosure.

Moving to FIG. 7, FIG. 7 is a flow chart of an example method related to the illustrated embodiments of FIGS. 2-6. The method starts at step 700 with providing an extracorporeal blood filtering machine. As discussed elsewhere herein, the extracorporeal blood filtering machine can comprise a blood circuit, an effluent circuit, and a source fluid circuit. The blood circuit can include a blood line with a blood inlet and blood outlet, a filter fluidly connected to the blood line between the blood inlet and the blood outlet, and a blood pump. The effluent circuit can include an effluent line fluidly connected to the filter and an effluent pump. The source fluid circuit can include a source fluid line fluidly connected to a source fluid reservoir and a source fluid pump. In some examples, the extracorporeal blood filtering machine also includes a hematocrit sensor in the blood line between the blood inlet and the filter. Also, in some examples, the extracorporeal blood filtering machine includes an air bubble sensor in the blood line between the filter and the blood outlet. The extracorporeal blood filtering machine can further include an anticoagulant source fluidly connected to the blood line between the blood inlet and the filter.

The method continues with step 702 with determining whether to connect a source fluid line to the blood circuit. If a determination is made to not connect the source fluid line to the blood circuit, the method can end with the extracorporeal blood filtering machine performing slow continuous ultrafiltration (SCUF). One example of SCUF operation is illustrated in FIG. 6. However, if a determination is made to connect the source fluid line to the blood circuit, the method continues to step 704, selecting a connection position in the blood circuit from among: the filter, between the blood inlet and the filter, and between the filter and the blood outlet. Once selected, the method continues with connecting the source fluid line to the connection position in the blood circuit as in step 706. In many examples, the source fluid line is connected to the connection position in the blood circuit and to no other positions in the blood circuit. In this way, only one source fluid line need be primed, and setup of the extracorporeal blood filtering machine can be significantly simplified.

The method continues with operating the blood pump to pump blood in the blood circuit in step 708. Specifically, the method includes operating the blood pump to pump blood from the blood inlet, through the blood line and the filter, and to the blood outlet, with the filter removing waste from the blood and providing the waste to the effluent line in the form of effluent. Next, the method continues in step 710 with operating the effluent pump to pump effluent in the effluent circuit. Specifically, the method includes operating the effluent pump to pump the effluent from the filter through the effluent line into an effluent receptacle. In some example methods, though, the effluent pump need not be operated. The method further continues with operating the source fluid pump to pump source fluid into the blood circuit in step 712. Specifically, the method includes operating the source fluid pump to pump source fluid from the source fluid reservoir through the source fluid line into the blood circuit. Depending upon which connection position is selected in step 704, the extracorporeal blood filtering machine will operate in one of continuous venovenous hemodialysis (CVVHD), continuous venovenous hemofiltration pre-filter (CVVHF—Pre), or continuous venovenous hemofiltration post-filter (CVVHF—Post). An example of CVVHD connection is illustrated in FIG. 3. An example of CVVHF—Pre is illustrated in FIG. 4. An example of CVVHF—Post is illustrated in FIG. 5.

As discussed with respect to FIGS. 2-6, the connection position can be chosen relative to other components of the extracorporeal blood filtering machine. For instance, in some embodiments, the connection position is between a hematocrit sensor and the filter. In some embodiments, the connection position is between the filter and an air bubble sensor.

The method can optionally continue in step 714 with determining that the source fluid line should be disconnected from the connection position in the blood circuit, discontinuing operation of the source fluid pump, and disconnecting the source fluid line from the connection position in the blood circuit. Next, the method can optionally continue in step 716 with selecting a reconnection position in the blood circuit. For instance, the reconnection position can be selected from among the filter, between the blood inlet and the filter, and between the filter and the blood outlet. Further in step 716, the method includes connecting the source fluid line to the reconnection position in the blood circuit and operating the source fluid pump to pump source fluid from the source fluid reservoir through the source fluid line into the blood circuit.

In addition to or in lieu of the optional step 714, the method can continue in optional step 718 with receiving a measurement of pressure in the blood line during priming of the blood line. The method further includes comparing the measurement with an expected value associated with the single selected connection position rather than to a different position. This method step can ensure the extracorporeal blood filtering machine is connected according to a selected connection position.

While the steps of FIG. 7 may be illustrated and discussed in a particular order, it will be appreciated that the steps of FIG. 7 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps. Moreover, while some steps are illustrated with dotted lines to indicate they are optional, in some examples, steps illustrated with solid lines can also be optional.

The extracorporeal blood filtering machine described with respect to FIGS. 2-6 and the accompanying method described with respect to FIG. 7 has several advantages over existing systems. For example, the extracorporeal blood filtering machine can be configured to perform four different methods of filtration including SCUF, CVVHD, CVVHF—Pre, and CVVHF—Post. The flexibility in operation of the extracorporeal blood filtering machine can allow it to replace multiple machines that may each perform only one method of filtration. Additionally, it can be relatively easy to change the operation of the extracorporeal blood filtering machine from one method of filtration to another. For example, one can remove the source fluid line from one connection point that has a self-sealing luer and does not require extra clamping, and can move and connect the source fluid line to a different connection point that also has a self-sealing luer for a quick connection. In some examples, being able to select a connection position from among multiple potential positions simplifies a priming operation. In such examples, the priming operation can include priming the single source fluid line, which then can be connected to the single selected connection position, as opposed to having to prime multiple source fluid lines that are each connected to a different position. Priming and connecting multiple source fluid lines to multiple different positions on the extracorporeal blood filtering machine to preserve optionality can be unnecessarily complex.

Figure 8:
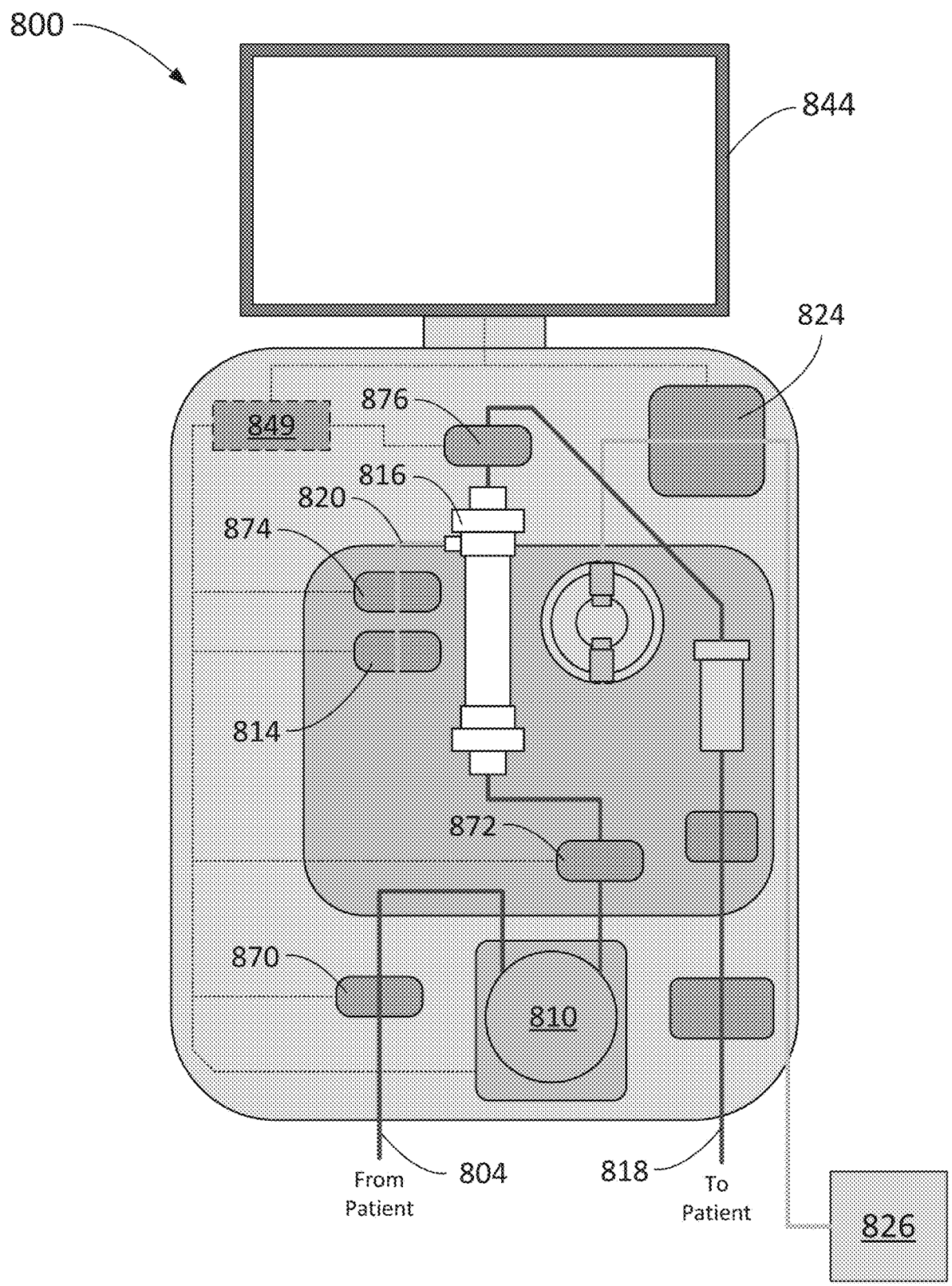
FIG. 8 is a schematic view of an example extracorporeal blood filtering machine according to an aspect of the present disclosure.

Moving to FIG. 8, FIG. 8 is a schematic view of an example extracorporcal blood filtering machine 800 according to an aspect of the present disclosure. The extracorporeal blood filtering machine 800 of FIG. 8 is similar to that of FIG. 2 in that it filters blood and can include some of the same components. However, the extracorporeal blood filtering machine 800 can include some additional components while not including other components of the extracorporeal blood filtering machine embodiment of FIG. 2. Further, for ease of readability, the extracorporeal blood filtering machine 800 in FIG. 8 does not illustrate some components that can be a part of the extracorporeal blood filtering machine 800. Some of these components include: a hematocrit sensor (e.g., 206), various pressure sensors (e.g., 208, 212, 222, 227), a source fluid reservoir (e.g., 234), a source fluid scale (e.g., 248), a source fluid line (e.g., 236), a source fluid pump (e.g., 238), an anticoagulant source (e.g., 240), an anticoagulant line (e.g., 242), and an effluent scale (e.g., 246). One having ordinary skill in the art will appreciate that some or all of the listed components can be included in the extracorporeal blood filtering machine 800 of FIG. 8.

Continuing with FIG. 8, the extracorporeal blood filtering machine 800 includes a blood circuit. The blood circuit comprises a blood line with a blood inlet 804 configured to receive blood from a patient and a blood outlet 818 configured to return the blood to the patient. The blood circuit also includes a filter 816 fluidly connected to the blood line between the blood inlet and the blood outlet and a blood pump 810. The filter 816 is configured to remove waste from the blood, such as in the form of effluent. The blood pump 810 is configured to pump the blood from the blood inlet 804, through the filter 816, and to the blood outlet 818. The extracorporeal blood filtering machine 800 also includes an effluent circuit. The effluent circuit comprises an effluent line 820 fluidly connected to the filter 816 with the effluent line configured to receive the waste from the filter 816 in the form of effluent. The effluent circuit also includes an effluent pump 824 configured to pump the effluent from the filter 816, through the effluent line 820, and into an effluent receptacle 826. The effluent circuit can additionally include a blood leak detector 814, which is configured to detect a presence of blood within the effluent line 820. The extracorporeal blood filtering machine 800 further includes a controller 849 and a display 844 with the controller 849 in communication with various components of the extracorporeal blood filtering machine 800 including the display 844 and the blood leak detector 814.

Further in FIG. 8, the extracorporeal blood filtering machine 800 includes one or more hemolysis sensors 870, 872, 874, 876, which are configured to sample fluid in a fluid line and output a hemolysis signal indicative of a detected degree of hemolysis in the fluid. A hemolysis sensor at a first location 870 can be used to sample the blood in the blood line between the blood inlet 804 and the blood pump 810. A hemolysis sensor at a second location 872 can be used to sample blood in the blood line between the blood pump 810 and the filter 816. A hemolysis sensor at a third location 874 can be used to sample effluent in the effluent line 820 between the filter 816 and the effluent pump 824. A hemolysis sensor at a fourth location 876 can be used to sample blood in the blood line between the filter 816 and the blood outlet 818. While four hemolysis sensors are illustrated, the extracorporeal blood filtering machine 800 can include one, two, three, four, or more hemolysis sensors. For example, the extracorporeal blood filtering machine 800 can include a single hemolysis sensor such as the hemolysis sensor at the third position 874. In another example, the extracorporeal blood filtering machine 800 can include two hemolysis sensors such as the hemolysis sensor at the first position 870 and the hemolysis sensor at the fourth position 876. Additionally, while each of the hemolysis sensors 870, 872, 874, 876 are illustrated as being located at a specific point within the blood line or effluent line, the hemolysis sensors 870, 872, 874, 876 can be located at different points within the blood line or effluent line.

In some examples, the hemolysis sensors 870, 872, 874, 876 are indirect sensors whereby they are not in direct contact with the fluid they are sampling. For example, the hemolysis sensors can be in optical communication with a fluid line. Alternatively, in some examples, the hemolysis sensors 870, 872, 874, 876 are direct contact sensors whereby they are in fluid communication with the fluid they are sampling. In some examples, some of the hemolysis sensors are indirect sensors and some of the hemolysis sensors are direct contact sensors. The hemolysis sensors 870, 872, 874, 876 can include optical-type sensors and use the electromagnetic spectrum to determine an amount of hemolysis present in the fluid.

Continuing with FIG. 8, the controller 849 is in electronic communication with each of the hemolysis sensor at the first position 870, the hemolysis sensor at the second position 872, the hemolysis sensor at the third position 874, and the hemolysis sensor at the fourth position 876. Each of the hemolysis sensors 870, 872, 874, 876 can output a hemolysis signal to the controller 849, with the hemolysis signal being indicative of a detected degree of hemolysis. The controller 849 is also in communication with the blood pump 810 and the effluent pump 824 and can receive signals indicative of the pump speed (e.g., rpm) of each and can output signals to control the blood pump 810 and the effluent pump 824. The controller 849 is further in communication with the blood leak detector 814 and can receive a signal from the blood leak detector 814 indicative of a blood leak in the effluent line. Additionally, the controller is in communication with the display 844 and can send and/or receive signals from the display 844.

In one example operation of the extracorporeal blood filtering machine 800 involving the controller 849, the blood leak detector 814 can detect a presence of blood within the effluent line 820 and can output a signal to the controller 849 indicative of the blood leak condition. The controller 849 can receive the signal from the blood leak detector 814 and can output a blood leak alarm signal. In some examples, the blood leak alarm signal is sent to the display 844 to alert a user of the blood leak condition. In some examples, the controller 849 can adjust operation of one or more of the blood pump 810 or the effluent pump 824 in response to receiving a signal from the blood leak detector indicative of a blood leak. For instance, the controller 849 can be configured to stop the effluent pump 824 if the blood leak detector 814 detects the presence of blood within the effluent line 820.

In some examples, the blood leak detector 814 can work together with the hemolysis sensor at the third position 874. For example, blood may improperly pass through the filter 816 into the effluent line either because the filter 816 is improperly allowing blood to pass through the filter 816 or because the blood is hemolyzed and is thus small enough to pass through the filter 816. The blood leak detector 814 can help determine if the filter 816 is improperly allowing blood to pass through the filter 816. The hemolysis sensor at the third position 874 can help determine if the blood is hemolyzed and is thus small enough to pass through the filter 816. In some examples, the controller 849 can receive a signal from the blood leak detector 814 and a hemolysis signal from the hemolysis sensor at the third position 874 and can identify a blood leak condition and/or a hemolysis condition.

In another example operation of the controller 849, the controller 849 can receive a hemolysis signal from one or more of the hemolysis sensors 870, 872, 874, 876. If, for instance, the received hemolysis signal indicates a detected degree of hemolysis exceeding a hemolysis threshold, the controller 849 can output a hemolysis alert signal to the display 844. The display 844 can then display a hemolysis alert to alert a user of the hemolysis condition. In some examples, the controller 849 can adjust operation of one or more of the blood pump 810 or the effluent pump 824 in response to receiving a hemolysis signal from a hemolysis sensor (e.g., 870, 872, 874, 876) exceeding a hemolysis threshold. For example, the controller 849 can completely stop the blood pump 810 and/or the effluent pump 824 in response to receiving a hemolysis signal exceeding the hemolysis threshold.

In some embodiments, multiple hemolysis thresholds can be used. For example, if the controller 1249 receives a hemolysis signal that exceeds a first hemolysis threshold, the controller 1249 can output a hemolysis alert signal. In this example, if the controller 1249 receives a hemolysis signal that exceeds a second hemolysis threshold, which is larger than the first hemolysis threshold, the controller 1249 can adjust (e.g., stop) operation of the blood pump 810 and/or the effluent pump 824.

In some examples, a hemolysis threshold comprises a slope threshold (e.g., function) of hemolysis over time. For example, a slope threshold can include an increased degree of hemolysis over a specific period of time. Using a slope threshold can be advantageous as a patient's condition can be the cause of hemolysis detected by the one or more hemolysis sensors instead of the machine. Accordingly, using an absolute value threshold may only alert a user of the extracorporeal blood filtering machine of a patient's condition and not of the condition of the machine. Thus, in some examples, the controller 1249 can receive multiple hemolysis signals from a hemolysis sensor (e.g., 870, 872, 874, 876) over time and can compare the slope or function of the multiple hemolysis signals to a slope or function indicating an increasing amount of hemolysis over time. An increasing amount of hemolysis can indicate the extracorporcal blood filtering machine is contributing to the hemolysis that is already present due to a patient's condition.

In general, it can be advantageous to include a hemolysis sensor (e.g., 872, 874, 876) between the blood pump 810 and the blood outlet 818 to determine if hemolysis is present in the blood line and/or effluent line. However, in some examples, it is further advantageous to include multiple hemolysis sensors (e.g., 872, 874, 876) located before and after one or more components (e.g., blood pump 810, filter 816) to determine if hemolysis is caused by the one or more components.

In some such examples, the extracorporeal blood filtering machine 800 includes a hemolysis sensor at the first position 870, which can be considered a reference hemolysis sensor 870. The reference hemolysis sensor 870 can be in communication with the controller 849 and configured to sample the blood in the blood line between the blood inlet and the blood pump. The reference hemolysis sensor 870 can then output a reference hemolysis signal indicative of a reference degree of hemolysis to the controller 849. The extracorporeal blood filtering machine 800 can further include a hemolysis sensor located anywhere between the blood pump 810 and the blood outlet 818. For instance, the extracorporeal blood filtering machine 800 can include a hemolysis sensor at the fourth position 876, which is configured to sample the blood in the blood line between the filter 816 and the blood outlet 818. The hemolysis sensor at the fourth position 876 can also be configured to output a hemolysis signal indicative of a detected degree of hemolysis.

As the controller 849 is in communication with both the reference hemolysis sensor 870 and the hemolysis sensor at the fourth position 876, the controller 849 can receive and compare the reference hemolysis signal and the hemolysis signal from the hemolysis sensor at the fourth position 876. The controller 849 can then output a hemolysis mismatch alert signal if the hemolysis signal from the hemolysis sensor at the fourth position 876 differs from the reference hemolysis signal by more than a threshold amount. In some such examples, the controller 849 can output the hemolysis mismatch signal to the display 844, which can display the hemolysis mismatch signal. By comparing the reference hemolysis signal with the hemolysis signal from the hemolysis sensor at the fourth position 876, the controller can determine if the blood pump 810, the filter 816, or other components in the blood line (e.g., pressure sensors 208, 212 of FIG. 2) are causing hemolysis.

While the above example uses the hemolysis sensor at the first position 870 as the reference hemolysis sensor along with the hemolysis sensor at the fourth position 876, any two hemolysis sensors can be used. For example, the reference hemolysis sensor can be the hemolysis sensor at the first position 870 while a subsequent hemolysis sensor can be the hemolysis sensor at the second position 872. This configuration would enable the controller 849 to determine if the blood pump is causing hemolysis. In another example, the reference hemolysis sensor can be the hemolysis sensor at the second position 872 while a subsequent hemolysis sensor can be the hemolysis sensor at the third position 874. This configuration would enable the controller 849 to determine if the filter 816 is causing hemolysis. In many cases, it is advantageous to have the hemolysis sensor at the first location 870 be the reference hemolysis sensor as it can sample blood that has not yet traveled through any components of the extracorporeal blood filtering machine 800 such as the blood pump 810 or the filter 816. Thus, the reference hemolysis sensor would only include hemolysis present in the patient, not hemolysis caused by any component of the extracorporeal blood filtering machine 800.

Figure 9:
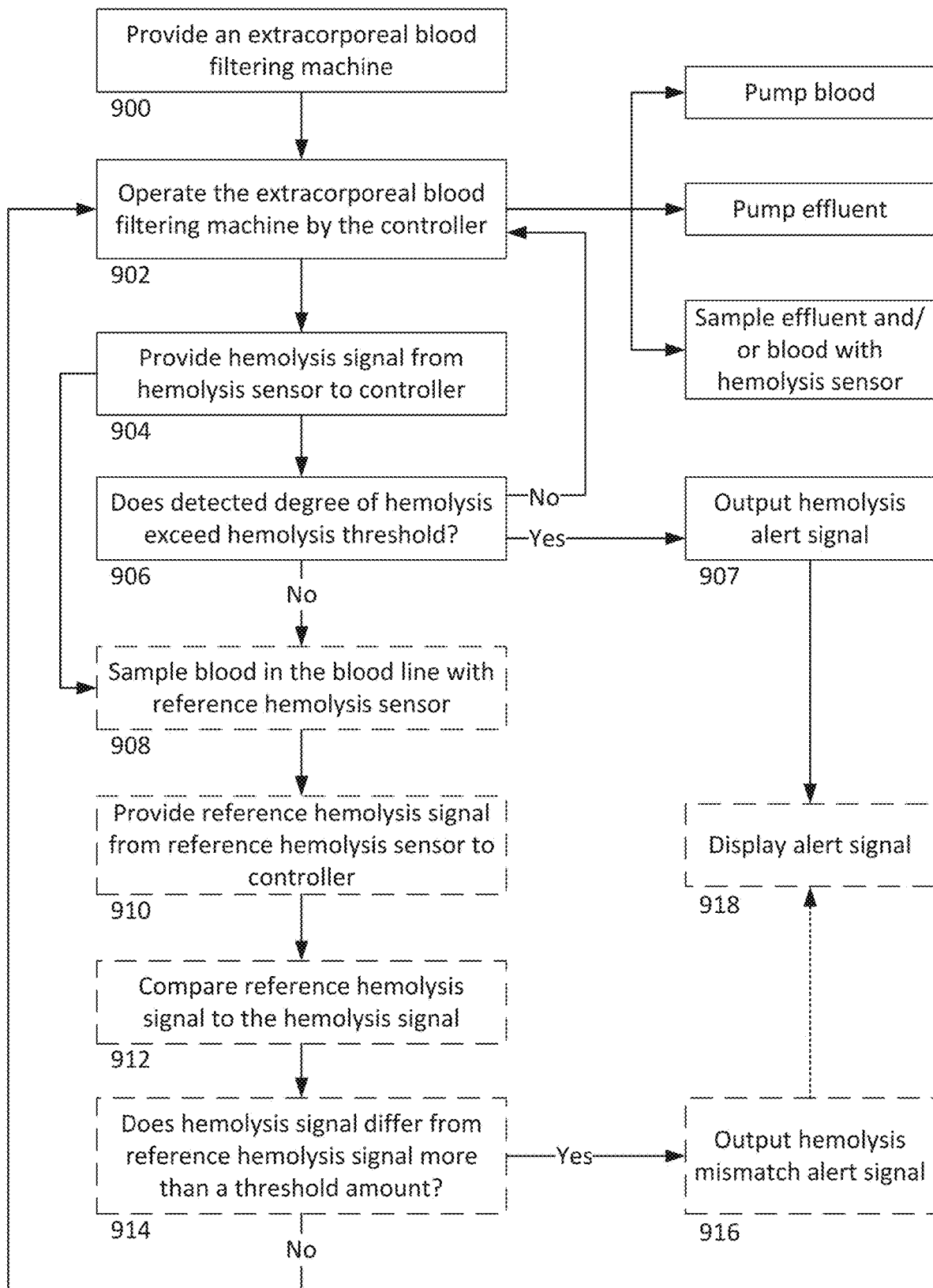
FIG. 9 is an example method using the extracorporeal blood filtering machine of FIG. 8 according to an aspect of the present disclosure.

Moving to FIG. 9, FIG. 9 illustrates an example method using the extracorporeal blood filtering machine of FIG. 8 and one or more of the hemolysis sensors 870, 872, 874, 876 according to an aspect of the present disclosure. The method starts at step 900 with providing an extracorporeal blood filtering machine. As discussed with respect to FIG. 8, the extracorporeal blood filtering machine can include a blood circuit comprising a blood line with a blood inlet. The blood circuit can further include a filter fluidly connected to the blood line between the blood inlet and the blood outlet and a blood pump configured to pump blood from the blood inlet, through the filter, and to the blood outlet. The extracorporeal blood filtering machine can also include an effluent circuit with an effluent line fluidly connected to the filter and an effluent pump configured to pump effluent generated by the filter through the effluent line to an effluent receptacle. The extracorporeal blood filtering machine also includes a hemolysis sensor and a controller in communication with the blood pump, the effluent pump, and the hemolysis sensor.

The method continues at step 902 with operating the extracorporeal blood filtering machine via the controller. Operating the extracorporeal blood filtering machine includes pumping blood with the blood pump from a patient into the blood inlet, through the blood line to the filter, and back to the patient through the blood line and out of the blood outlet. The filter can remove waste from the blood and provide the waste to the effluent line in the form of effluent. Operating the extracorporeal blood filtering machine also includes pumping the effluent with the effluent pump through the effluent line into an effluent receptacle. In some examples, the effluent pump and other components need not be operated when operating the extracorporcal blood filtering machine. Operating the extracorporeal blood filtering machine further includes sampling the effluent in the effluent line and/or blood in the blood line with the hemolysis sensor.

The method then continues at step 904 with providing a hemolysis signal indicative of a detected degree of hemolysis from the hemolysis sensor to the controller. Next, in step 906, a determination is made to whether the detected degree of hemolysis from the hemolysis sensor exceeds a hemolysis threshold. If the detected degree of hemolysis does exceed the hemolysis threshold, then the method continues with the controller outputting a hemolysis alert signal as in step 907. If the detected degree of hemolysis does not exceed the hemolysis threshold, then the method can continue back with step 902, operating the extracorporeal blood filtering machine. Optionally, in some examples, the controller can output a hemolysis alert signal to a display, which can then display the hemolysis alert signal as in step 918.

In some examples, the method can include providing a reference hemolysis sensor in addition to the hemolysis sensor sampling effluent from the effluent line and/or blood from the blood line. In such examples, the method can include steps 908-916. The method can either go from step 904 directly to step 908, or alternatively, can go to step 908 after a negative result of the hemolysis threshold determination of step 906.

In step 908, the method continues with sampling the blood in the blood line between the blood inlet and the blood pump with the reference hemolysis sensor. The method further continues in step 910 with providing a reference hemolysis signal indicative of a reference degree of hemolysis from the reference hemolysis sensor to the controller. Next, in step 912, the controller compares the reference hemolysis signal to the hemolysis signal. A determination is then made in step 914 of whether the hemolysis signal differs from the reference hemolysis signal by more than a threshold amount. If the hemolysis signal does differ from the reference hemolysis signal by more than the threshold amount, the controller can output a hemolysis mismatch alert signal as in step 916. If the hemolysis signal does not differ from the reference hemolysis signal by more than the threshold amount, the method can continue with step 902, operating the extracorporeal blood filtering machine. In some examples, the controller can output the hemolysis mismatch alert signal to the display which can display the hemolysis mismatch alert signal.

While the steps of FIG. 9 may be illustrated and discussed in a particular order, it will be appreciated that the steps of FIG. 9 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps. Moreover, while some steps are illustrated with dotted lines to indicate they are optional, in some examples, steps illustrated with solid lines can also be optional.

Figure 10:
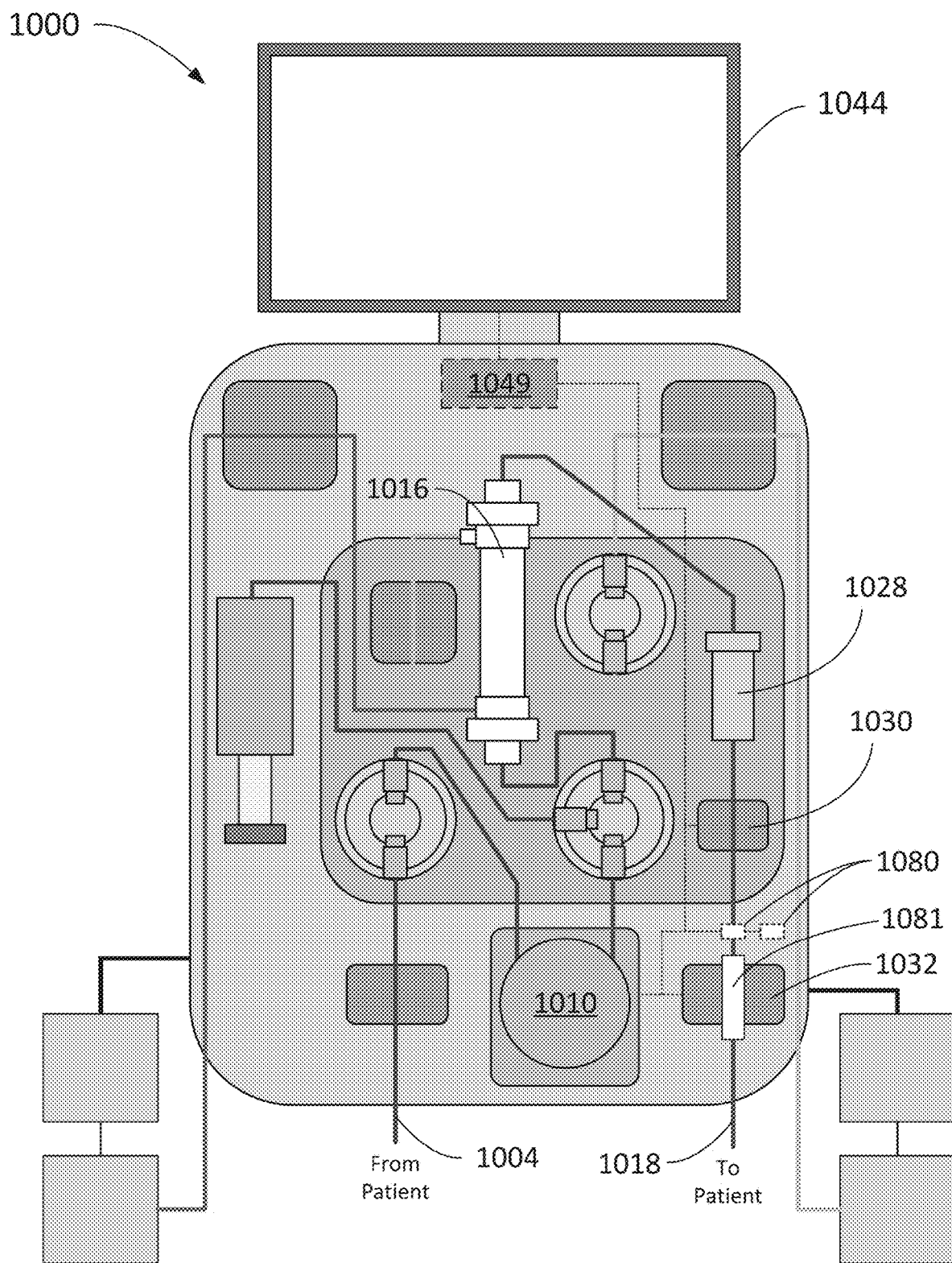
FIG. 10 is a diagrammatic view of an example extracorporeal blood filtering machine according to an aspect of the present disclosure.

Moving to FIG. 10, FIG. 10 is a diagrammatic view of an example extracorporeal blood filtering machine 1000 according to an aspect of the present disclosure. The extracorporeal blood filtering machine 1000 of FIG. 10 is similar to that of the extracorporeal blood filtering machine of FIG. 2 and can include some or all of the components of FIG. 2. However, the extracorporeal blood filtering machine 1000 can include additional components not found in FIG. 2.

In the illustrated embodiment of FIG. 10, the extracorporeal blood filtering machine 1000 includes a blood circuit with a blood line having a blood inlet 1004 configured to receive blood from a patient and a blood outlet 1018 configured to return the blood to the patient. The blood circuit also includes a filter 1016 fluidly connected to the blood line between the blood inlet 1004 and the blood outlet 1018. The blood circuit further includes a blood pump 1010 configured to pump the blood from the blood inlet 1004 to the blood outlet 1018 through the filter 1016, with the filter 1016 configured to remove waste from the blood.

The extracorporeal blood filtering machine 1000 also includes a bubble trap 1028 configured to remove gas bubbles from the blood line before the blood outlet 1018. After the bubble trap 1028, the extracorporeal blood filtering machine 1000 includes a bubble sensor 1030 configured to identify gas bubbles within the blood line before the blood outlet 1018. For instance, in some examples, the bubble sensor 1030 can be an air bubble sensor configured to identify an air bubble in the blood line and output an air bubble signal to a connected controller 1049.

The extracorporeal blood filtering machine 1000 additionally includes a clamp 1032 configured to engage the blood line and to move between a clamp-open position, in which the blood line is open for blood to return to the patient through the blood outlet 1018, and a clamp-closed position, in which the blood line is closed off and blood is prevent from returning to the patient through the blood outlet 1018. In some examples, the clamp 1032 is configured to impart a predetermined clamping force on the blood line when in the clamp-closed position. The clamp 1032 can be configured to prevent blood from returning to the patient for a variety of reasons, including preventing a detected air bubble from entering the patient's circulatory system. In some examples, the extracorporeal blood filtering machine 1000 can include thermal insulation 1081 around the blood line. The thermal insulation 1081 can be bonded to the blood line in any location and extend for any length of the blood line. However, in the example of FIG. 10, the thermal insulation 1081 is bonded to where the clamp 1032 engages the blood line before the blood outlet 1018. The thermal insulation 1081 can reduce temperature-based fluctuations in the pliability of the blood line.

Further in FIG. 10, the extracorporeal blood filtering machine 1000 includes a temperature sensor 1080 configured to measure an ambient air temperature and/or a temperature of the blood line. In FIG. 10, the temperature sensor 1080 is illustrated as being located on the exterior of the blood line proximate the clamp 1032, or as being located proximate the clamp 1032. In some examples, the extracorporeal blood filtering machine 1000 includes more than one temperature sensor. For instance, one temperature sensor can be located on the exterior of the blood line while another temperature sensor is located away from the blood line (e.g., not contacting the blood line). In some examples, a temperature sensor on the exterior of the blood line can measure the temperature of an exterior of the blood line while a temperature sensor away from the blood line can measure an ambient air temperature.

The extracorporeal blood filtering machine 1000 can also include a controller 1049 and a display 1044. The controller 1049 is in communication with the blood pump 1010 and the clamp 1032 and can be in further communication with the temperature sensor 1080 and the bubble sensor 1030. The controller 1049 can also be in communication with the display 1044. In some examples, the controller 1049 can be in communication with other components of the extracorporeal blood filtering machine 1000, including components described in connection with FIG. 2 and FIG. 8.

In operation, the controller 1049 can be configured to receive the ambient air temperature and/or the blood line temperature from the temperature sensor 1080 and can adjust an operation of the clamp 1032 based on the received ambient air temperature and/or blood line temperature. This operation of the clamp 1032 can be advantageous as the tubing on which the clamp 1032 clamps down can become stiffer over time due to a change in its temperature. For instance, in some examples, the controller 1049 is configured to adjust the predetermined clamping force of the clamp 1032 based on the received ambient air temperature and/or blood line temperature. In some such examples, the controller 1049 can be configured to increase the predetermined clamping force when the ambient air temperature and/or the blood line temperature is below a first threshold. Similarly, the controller 1049 can be configured to decrease the predetermined clamping force when the ambient air temperature and/or the blood line temperature is above a second threshold. Decreasing the predetermined clamping force of the clamp 1032 can be advantageous as clamping too hard on the tubing may cause it to rupture.

In another operation, the controller 1049 can adjust operation of the clamp 1032 by causing the clamp to move from the clamp-open position to the clamp-closed position and back to the clamp-open position if the ambient air temperature and/or the blood line temperature is below a threshold. Again, the tubing of the blood line on which the clamp 1032 clamps down can become stiffer over time, in part due to temperature changes (e.g., colder temperatures). By adjusting the operation of the clamp 1032 to move between a clamp-open position to the clamp-closed position and back again (e.g., to squeeze the tube one or two or several times), the tubing of the blood line can be kept soft enough to clamp with a predetermined clamping force. In some examples, the controller 1049 can be configured to pause the blood pump 1010 when the clamp 1032 is in the clamp-closed position. This operation can prevent a pressure buildup in the blood line. In some examples, the controller 1049 can repeat the process of clamping and unclamping the clamp 1032 periodically to maintain a desired stiffness of the tubing of the blood line.

In some examples, the controller 1049 can be configured to initiate an alarm mode in which the controller controls the clamp 1032 to move from the clamp-open position to the clamp-closed position. In some such examples, the controller 1049 can initiate the alarm mode when the controller 1049 itself identifies an alarm condition. Additionally or alternatively, the controller 1049 can be configured to initiate an alarm mode when the controller 1049 receives an alarm signal. The alarm signal can comprise any number of signals including, for instance, an alarm signal from the bubble sensor 1030. For example, if the bubble sensor 1030 identifies an air bubble in the blood line, it can send an air bubble signal to the controller 1049 which the controller 1049 receives and subsequently initiates the alarm mode. Thus, if the bubble sensor 1030 identifies an air bubble in the blood line, the controller 1049 can cause the clamp 1032 to move to the clamp-closed position and prevent the air bubble from entering a patient's bloodstream.

Figure 11:
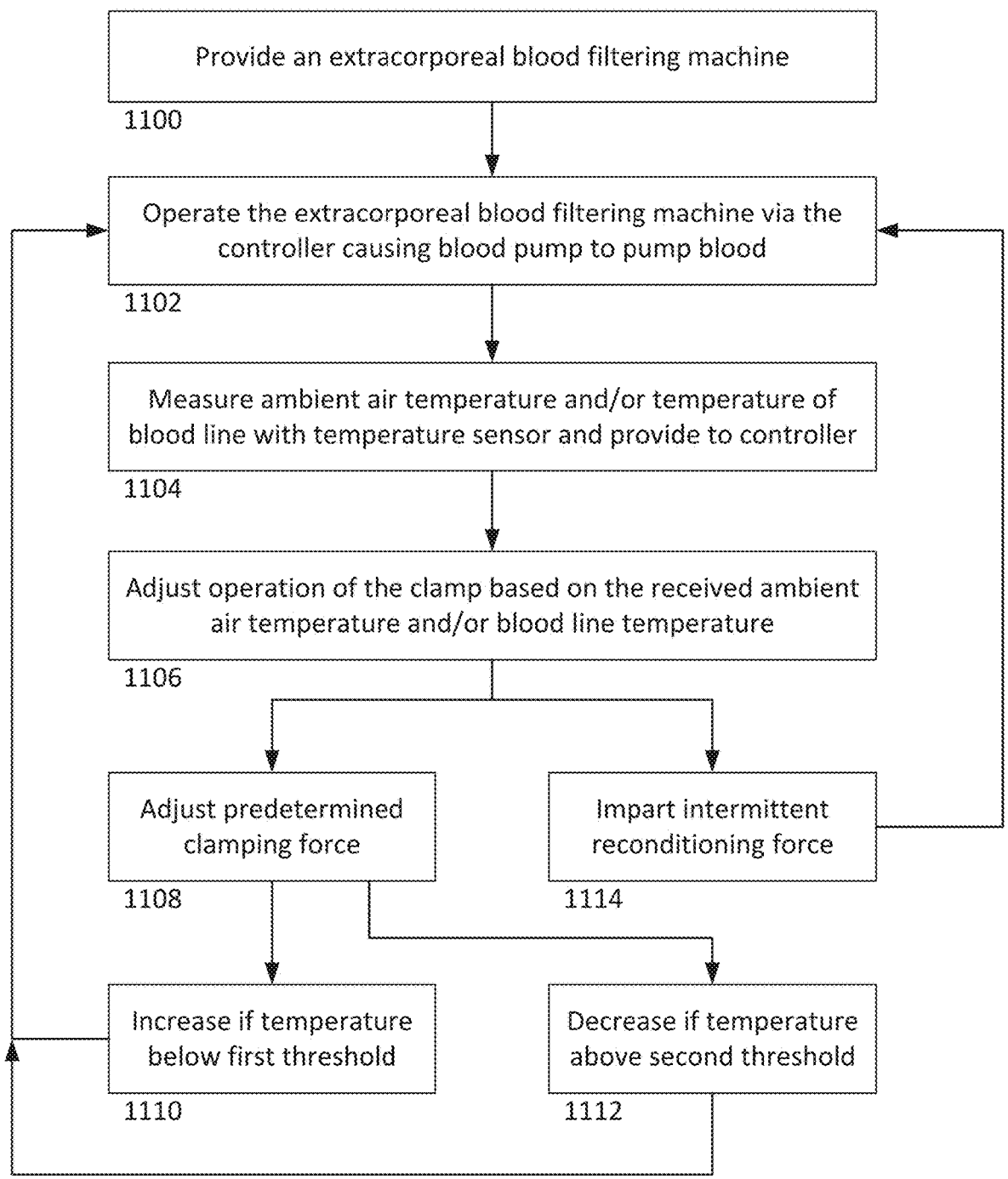
FIG. 11 is a flowchart of an example operation of the example extracorporeal blood filtering machine of FIG. 10.

Moving to FIG. 11, FIG. 11 is a flowchart of an example operation of the example extracorporeal blood filtering machine of FIG. 10. The method starts at step 1100 with providing an extracorporeal blood filtering machine. The extracorporeal blood filtering machine comprises a blood circuit. The blood circuit comprises a blood line including a blood inlet and a blood outlet, a filter fluidly connected to the blood line between the blood inlet and the blood outlet, and a blood pump. The extracorporeal blood filtering machine also includes a clamp engaged with the blood line, a temperature sensor, and a controller in communication with the blood pump and the clamp.

Next, in step 1102, the controller operates the extracorporeal blood filtering machine causing the blood pump to pump blood from a patient, through the blood inlet, into the filter, and out through the blood outlet back to the patient. The method also includes measuring the ambient air temperature and/or temperature of the blood line with the temperature sensor and providing the ambient air temperature and/or the temperature of the blood line to the controller in step 1104. The method continues with step 1106 with the controller adjusting an operation of the clamp based on the received ambient air temperature and/or blood line temperature.

In some examples, the controller adjusting the operation of the clamp includes adjusting a predetermined clamping force the clamp imparts to the blood line to prevent blood from returning to the patient through the blood circuit as in 1108. In some such examples, adjusting the predetermined clamping force includes increasing the predetermined clamping force via the controller when the ambient air temperature and/or the blood line temperature is below a first threshold (e.g., when tubing is stiffer) as in 1110. Further, in some such examples, adjusting the predetermined clamping force includes decreasing the predetermined clamping force via the controller when the ambient air temperature and/or the blood line temperature is above a second threshold (e.g., when tubing is softer).

In some examples, the controller adjusting operation of the clamp includes causing the clamp to impart an intermittent reconditioning force on the blood line by the controller as in step 1114. The intermittent reconditioning force can include the clamp moving from a clamp-open position to a clamp-closed position and back to the clamp-open position (e.g., squeezing the blood line a few times). In some examples, the intermittent reconditioning force includes the clamp moving from the clamp-open position to a partially-closed position where some blood still flows through the blood line past the clamp.

In some embodiments, only one of adjusting the predetermined clamping force or imparting an intermittent reconditioning force is performed. Alternatively, in some embodiments, both can be performed. For example, the controller can adjust the predetermined clamping force of the clamp based on a received ambient air temperature and/or blood line temperature and can further intermittently apply the adjusted, predetermined clamping force to the blood line.

While the steps of FIG. 11 may be illustrated and discussed in a particular order, it will be appreciated that the steps of FIG. 11 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps.

The above embodiments are advantageous as they can help ensure that the clamp can maintain proper operation and prevent blood, which may contain gas bubbles, from being returned to the patient and causing the patient harm.

Figure 12:
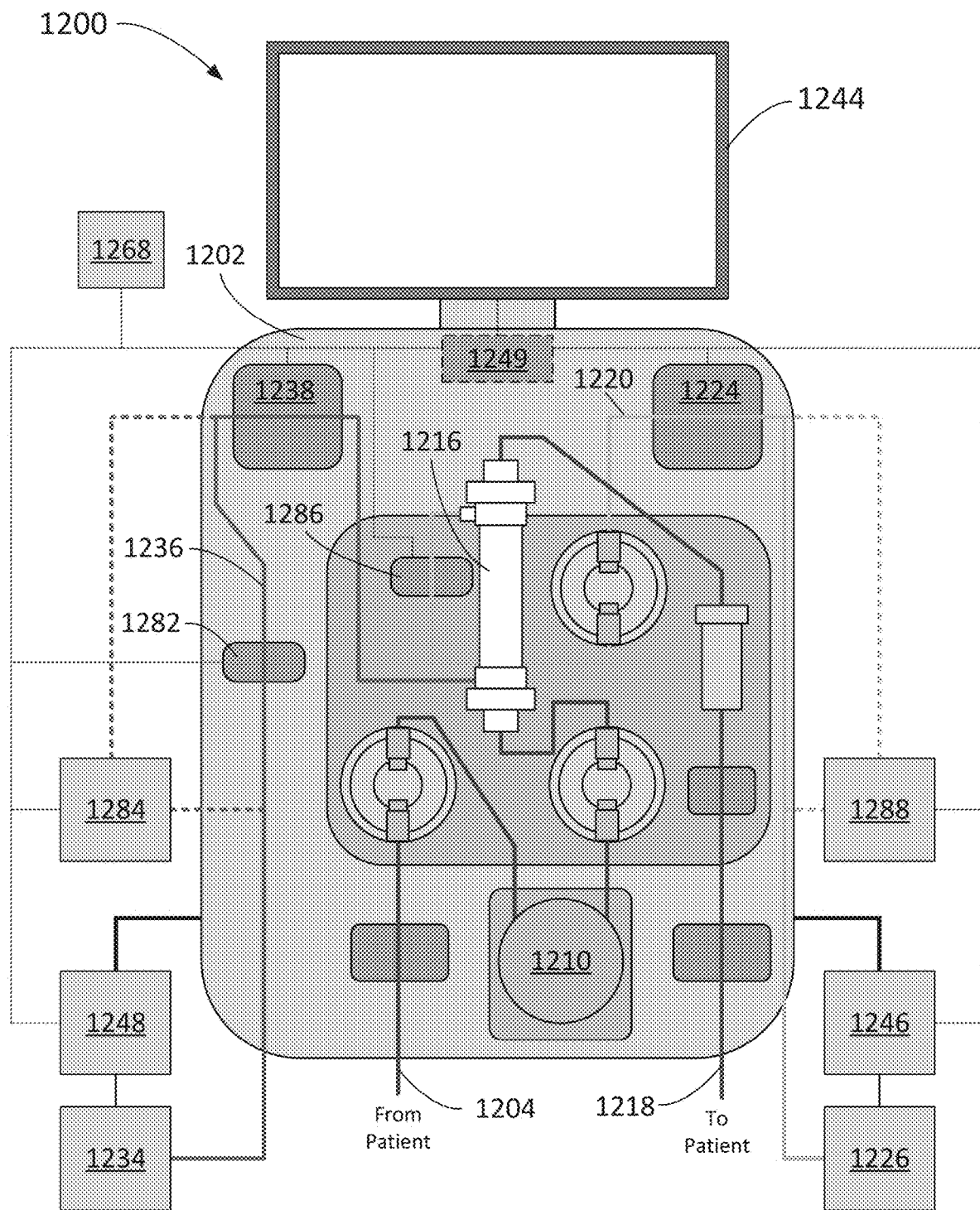
FIG. 12 is a diagrammatic view of an example extracorporeal blood filtering system according to an aspect of the present disclosure.

Moving to FIG. 12, FIG. 12 is a diagrammatic view of an example extracorporeal blood filtering system 1200 according to an aspect of the present disclosure. The extracorporeal blood filtering system 1200 can include some or all of the components described elsewhere herein such as in connection with FIG. 2 and FIG. 10. However, the extracorporeal blood filtering system 1200 can also include additional components. For example, the extracorporeal blood filtering system 1200 includes one or more density sensors 1282, 1284, 1286, 1288. One of ordinary skill in the art will appreciate the extracorporeal blood filtering system 1200 is not limited to the illustrated components of FIG. 12 and that any additional components illustrated and described in FIG. 12 can be added to other extracorporeal blood filtering machines or systems described elsewhere herein. In examples like the one shown in FIG. 12, extracorporeal blood filtering systems can determine the density of fluids (e.g., source fluid, effluent) flowing within the system and use the determined density values to ensure optimal fluid balance. Determining fluid densities in the ways described herein can provide significant benefits as compared to simply assuming that the density of such fluids matches the density of water.

The extracorporeal blood filtering system 1200 includes a blood circuit. The blood circuit includes a blood line with a blood inlet 1204 configured to receive blood from a patient and a blood outlet 1218 configured to return the blood to the patient. The blood circuit also includes a filter 1216 fluidly connected to the blood line between the blood inlet 1204 and the blood outlet 1218 and a blood pump 1210 configured to pump the blood from the blood inlet 1204 to the blood outlet 1218 through the filter 1216 with the filter 1216 configured to remove waste from the blood.

The extracorporeal blood filtering system 1200 also includes an effluent circuit. The effluent circuit includes an effluent line 1220 fluidly connected to the filter, with the effluent line configured to receive the waste from the filter 1216 in the form of effluent. The effluent circuit also includes an effluent pump 1224 configured to pump the effluent from the filter 1216, through the effluent line 1220, to an effluent receptacle 1226. In some examples, the effluent circuit can also include an effluent scale 1246 configured to measure an effluent weight value of the effluent receptacle 1226.

In some examples, the extracorporeal blood filtering system 1200 includes a source fluid circuit. The source fluid circuit includes a source fluid line 1236 fluidly connected to a source fluid reservoir 1234 and to the blood circuit. The source fluid circuit also includes a source fluid pump 1238 configured to pump source fluid from the source fluid reservoir 1234, through the source fluid line 1236, into the blood circuit. In some such examples, the source fluid circuit can also include a source fluid scale 1248 configured to measure a source fluid weight value of the source fluid reservoir 1234.

In some embodiments, the extracorporeal blood filtering system 1200 includes a display 1244. The display 1244 can be used to display information and/or to act as a user input and receive user inputs. For example, the display 1244 can be used to display information about the extracorporeal blood filtering system 1200 and/or used as a touch display configured to receive a user input in the form of touch.

In some examples, the extracorporeal blood filtering system 1200 includes a user input device 1268 which is configured to receive a user input. The user input device 1268 can be separate from the extracorporeal blood filtering system 1200 or can be integrated into the extracorporeal blood filtering system 1200. Some examples of a user input device 1268 can include a computer mouse, a keyboard, or a touch interface.

In some embodiments, the extracorporeal blood filtering system 1200 includes one or more density sensors 1282, 1284, 1286, 1288 each configured to measure a fluid density of a connected fluid line. In FIG. 12, a first source fluid density sensor 1282 can be used to sample source fluid in the source fluid line 1236 between the source fluid reservoir 1234 and the filter 1216. The first source fluid density sensor 1282 can be considered inline with the source fluid line 1236 as it is within the extracorporeal blood filtering machine 1202, and the source fluid line 1236 runs through it.

A second source fluid density sensor 1284 can also be used to sample source fluid between the source fluid reservoir and filter 1216. However, the second source fluid density sensor 1284 can be considered offline from the source fluid line 1236 as it is outside of the extracorporeal blood filtering machine 1202 and the source fluid line 1236 need not run through it. In some examples, the source fluid line 1236 can run from the source fluid reservoir 1234, through the second source fluid density sensor 1284, and back into the source fluid pump 1238. Additionally or alternatively, a different fluid line is connected between the source fluid reservoir 1234 and the second source fluid density sensor 1284. In some embodiments, the second source fluid density sensor 1284 is part of a separate machine than the extracorporeal blood filtering machine 1202 and is housed in a separate housing. In some such embodiments, though, the second source fluid density sensor can be considered part of the extracorporeal blood filtering system 1200. While two source fluid density sensors 1282, 1284 are illustrated, the extracorporeal blood filtering system 1200 can include only one of the first source fluid density sensor 1282 or the second source fluid density sensor 1284. In some embodiments, no source fluid density sensor is included in the extracorporeal blood filtering system.

Continuing with FIG. 12, the extracorporeal blood filtering system 1200 includes a first effluent density sensor 1286, which can be used to sample effluent in the effluent line 1220 between the filter 1216 and the effluent receptacle 1226. The first effluent density sensor 1286 can be considered inline with the effluent line 1220 as it is within the extracorporeal blood filtering machine 1202, and the effluent line 1220 runs through it.

A second effluent density sensor 1288 can also be used to sample effluent between the filter 1216 and the effluent receptacle 1226. However, the second effluent density sensor 1288 can be considered offline from the effluent line 1220 as it is outside of the extracorporeal blood filtering machine 1202, and the effluent line 1220 need not run through it. In some examples, the effluent line 1220 can run from the filter 1216, through the second effluent density sensor 1288, and to the effluent receptacle 1226. Additionally or alternatively, a different fluid line can be connected between the filter 1216 and the second effluent density sensor 1288. In some embodiments, the second effluent density sensor 1288 is part of a separate machine than the extracorporeal blood filtering machine 1202 and is housed in a separate housing. In some such embodiments, though, the second effluent density sensor can be considered part of the extracorporeal blood filtering system 1200. While two effluent density sensors 1286, 1288 are illustrated, the extracorporeal blood filtering system 1200 can include only one of the first effluent density sensor 1286 or the second effluent density sensor 1288. In some embodiments, no effluent density sensor is included in the extracorporeal blood filtering system.

The extracorporeal blood filtering system 1200 further includes a controller 1249, which can be in communication with various components within the extracorporeal blood filtering system 1200. In FIG. 12, the controller 1249 is in communication with the effluent pump 1224, the effluent scale 1246, the source fluid pump 1238, the source fluid scale 1248, the display 1244, the one or more density sensors 1282, 1284, 1286, 1288, and the user input device 1268. The controller 1249 can also be in communication with further components of the extracorporeal blood machine (e.g., the blood pump 1210).

In one example operation, the controller 1249 is configured to determine a quantity (e.g., a volume) of effluent pumped through the effluent line 1220 into the effluent receptacle 1226 based on a determined effluent density value. The controller 1249 can be configured to receive the determined effluent density value in multiple ways. For instance, in some examples, the controller 1249 can receive the determined effluent density value from one of the first effluent density sensor 1286 or the second effluent density sensor 1288. Additionally or alternatively, in some examples, the controller 1249 can receive the determined effluent density value from a user input such as from the user input device 1268 or the display 1244. In some such examples, the controller 1249 can receive a user input that is indicative of the determined effluent density value output by an effluent density sensor (e.g., the second effluent density sensor 1288). Thus, the controller 1249 can receive a determined effluent density value from an effluent density sensor which is offline from the extracorporeal blood filtering machine 1202.

In some examples, to determine the quantity (e.g., the volume) of effluent pumped through the effluent line 1220 into the effluent receptacle 1226, the controller 1249 can receive a determined effluent density value and receive an effluent weight value from the effluent scale 1246. The controller 1249 can then take the effluent weight value from the effluent scale 1246 and divide it by the determined effluent density value to determine a quantity of effluent in the effluent receptacle 1226.

The controller 1249 can also be configured to output a system control signal based on the determined quantity of effluent. The system control signal can include a signal to control one or more aspects of the extracorporeal blood filtering system 1200 such as the effluent pump 1224.

In a similar example operation, the controller 1249 is configured to determine a quantity (e.g., a volume) of source fluid pumped through the source fluid line 1236 from the source fluid reservoir 1234 based on a determined source fluid density value. The controller 1249 can be configured to receive the determined source fluid density value in multiple ways. For instance, in some examples, the controller 1249 can receive the determined source fluid density value from one of the first source fluid density sensor 1282 or the second source fluid density sensor 1284. Additionally or alternatively, in some examples, the controller 1249 can receive the determined source fluid density value from a user input such as from the user input device 1268 or the display 1244. In some such examples, the controller 1249 can receive a user input that is indicative of the determined source fluid density value output by a source fluid density sensor (e.g., the second source fluid density sensor 1284). Thus, the controller 1249 can receive a determined source fluid density value from a source fluid density sensor that is offline from the extracorporeal blood filtering machine 1202.

In some examples, to determine the quantity of source fluid pumped through the source fluid line 1236 from the source fluid reservoir 1234, the controller 1249 can receive a determined source fluid density value and receive a source fluid weight value from the source fluid scale 1248. The controller 1249 can then take the source fluid weight value from the source fluid scale 1248 and divide it by the determined source fluid density value to determine a quantity of source fluid pumped from the source fluid reservoir 1234.

The controller 1249 can also be configured to output a system control signal based on the determined quantity of source fluid. The system control signal can include a signal to control one or more aspects of the extracorporeal blood filtering system 1200 such as the source fluid pump 1238.

In some examples, the controller 1249 is configured to determine both the quantity (e.g., volume) of effluent pumped through the effluent line 1220 and the quantity (e.g., volume) of source fluid pumped through the source fluid line 1236. In some such examples, the controller 1249 can use an effluent density sensor 1286 that is inline with the effluent line 1220 and use a source fluid density sensor 1284 that is offline from the source fluid line 1236. Alternatively, in some examples, the controller 1249 can use an effluent density sensor 1288 that is offline from the effluent line 1220 and a source fluid density sensor 1282 that is inline with the source fluid line 1236. Other combinations of an effluent density sensor being inline/offline and a source fluid density sensor being offline/inline are also contemplated.

The extracorporeal blood filtering system 1200 of FIG. 12 can be operated in a priming operation and a standard operation. A priming operation is used to flush air from the blood line by using a fluid (e.g., saline) within the blood line. The priming operation is usually performed once before a standard operation. During the priming operation, the source fluid pump 1238 is configured to pump priming fluid from a priming fluid reservoir through the source fluid line. Additionally, during the priming operation, the source fluid scale 1248 is configured to measure a priming fluid weight value of the priming fluid reservoir. In some examples, the priming fluid reservoir is the source fluid reservoir 1234, however in some examples, the priming fluid reservoir is a separate reservoir. During the standard operation, the source fluid pump 1238 is configured to pump source fluid from the source fluid reservoir 1234 through the source line into the blood circuit. Additionally, during the standard operation, the source fluid scale 1248 is configured to measure a source fluid weight value of the source fluid reservoir 1234.

The controller 1249 can control aspects of the extracorporeal blood filtering system 1200 during both the priming operation and the standard operation. For example, the controller 1249 is configured to determine a source fluid pump rate during the priming operation based on the priming fluid weight value and known priming fluid density value. The priming fluid density value can be known beforehand as a user can input the priming fluid density into a user input, which the controller 1249 can then receive. The controller 1249 can also be configured to determine the determined source fluid density value during standard operation based on the source fluid weight value and the source fluid pump rate. Thus, the extracorporeal blood filtering system 1200 can be primed with a known density liquid, and the controller 1249 can determine a source fluid pump rate and subsequently determine a source fluid density due to the known source fluid pump rate and the source fluid weight value.

In some examples, the controller 1249 is further configured to determine an effluent pump rate, such as that of effluent pump 1224, during the priming operation. In some such examples, the effluent pump rate can be based on an effluent weight value measured by the effluent scale 1246 and the known priming fluid density value. To obtain the effluent pump rate, a user can configure the extracorporeal blood filtering system 1200 such that the priming fluid is pumped through the effluent pump 1224 and is weighed by the effluent scale 1246. The controller 1249 can be configured to determine the determined effluent density value during standard operation based on the effluent weight value and the effluent pump rate. Thus, the extracorporeal blood filtering system 1200 can be primed with a known density liquid, and the controller 1249 can determine an effluent pump rate and subsequently determine an effluent density due to the known effluent pump rate and the effluent weight value.

Figure 13:
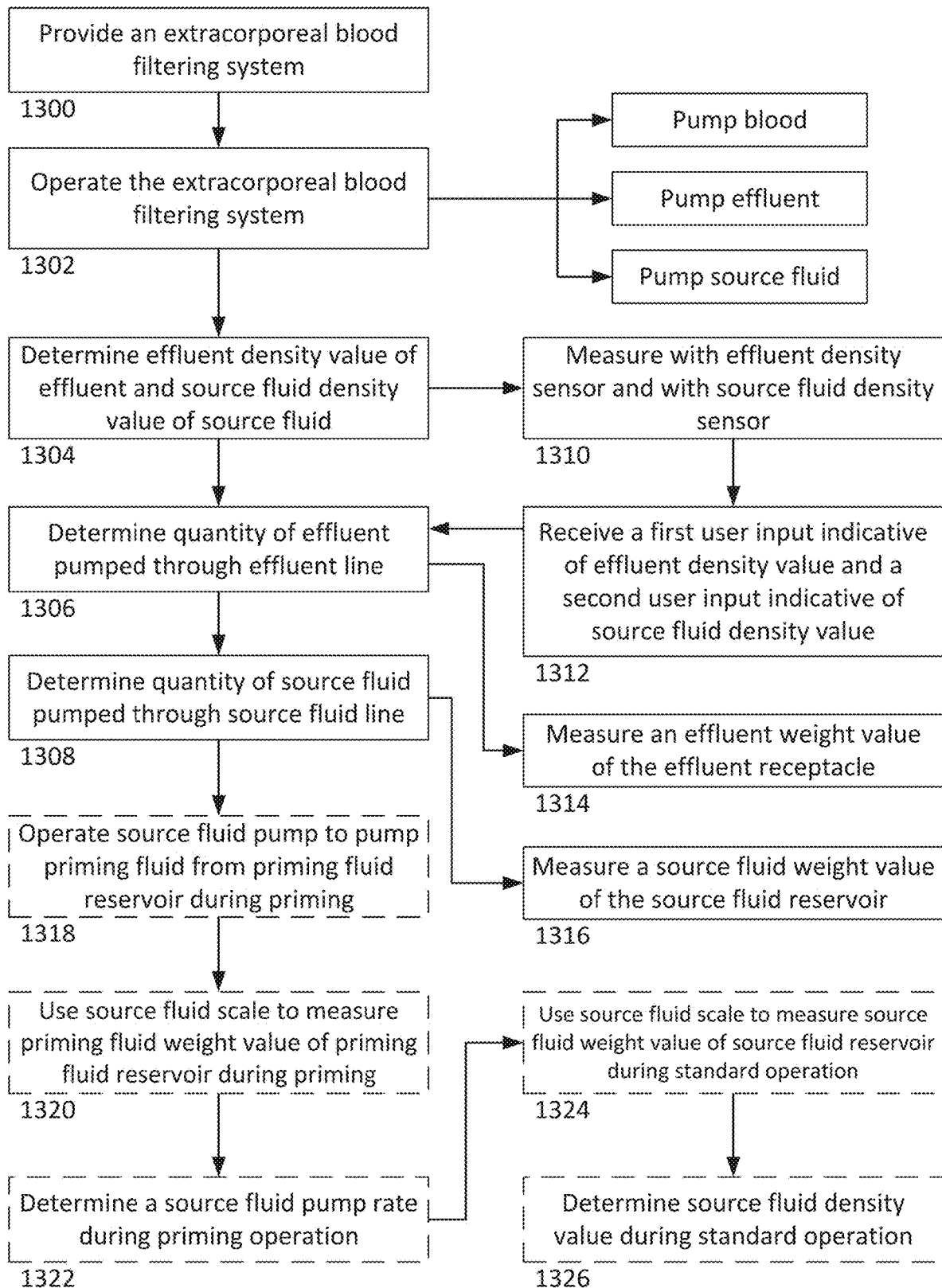
FIG. 13 is flowchart of an example operation of the extracorporeal blood filtering system of FIG. 12 according to an aspect of the present disclosure.

Moving to FIG. 13, FIG. 13 is flowchart of an example operation of the extracorporeal blood filtering system 1200 of FIG. 12 according to an aspect of the present disclosure. The method starts at step 1300 with providing an extracorporeal blood filtering system. As discussed in connection with FIG. 11, the extracorporeal blood filtering machine includes a blood circuit. The blood circuit includes a blood line with a blood inlet configured to receive blood from a patient and a blood outlet configured to return the blood to the patient. The blood circuit also includes a filter fluidly connected to the blood line between the blood inlet and the blood outlet and a blood pump. The extracorporeal blood filtering system also includes an effluent circuit, which comprises an effluent line fluidly connected to the filter and an effluent pump. In some examples, the extracorporeal blood filtering system further includes a source fluid circuit, which comprises a source fluid line fluidly connected to a source fluid reservoir and to the blood circuit along with a source fluid pump. In some examples, the extracorporeal blood filtering system includes one or more density sensors such as an effluent density sensor and a source fluid density sensor. In some examples, the extracorporeal blood filtering machine includes an effluent scale and a source fluid scale.

The method continues at step 1302 with operating the blood pump to pump blood received from a patient at the blood inlet through the filter and back to the patient at the blood outlet, with the filter removing waste from the blood and providing the waste to the effluent line in the form of effluent. Next, in step 1304, the method continues with determining an effluent density value of the effluent and a source fluid density value of the source fluid. In some examples, the step of determining the effluent density value of the effluent and determining the source fluid density value of the source fluid comprises measuring the effluent density value with an effluent density sensor and measuring the source fluid density value with a source fluid density sensor as in step 1310. In some such examples, the effluent density sensor and the source fluid density sensor can be inline with the effluent line and source fluid line respectively. Alternatively, in some such examples, the effluent density sensor and the source fluid density sensor can be offline from the effluent line and source fluid line respectively. In some examples, the effluent density sensor is inline, while the source fluid density sensor is offline. In some examples, the effluent density sensor is offline, while the source fluid density sensor is inline. In some embodiments where the effluent density sensor and/or the source fluid density sensor are offline, determining the effluent density value of the effluent and/or the source fluid density value of the source fluid can include receiving user input. For example, at step 1312, the method includes receiving a first user input indicative of the effluent density value output by the effluent density sensor and receiving a second user input indicative of the source fluid density value output by the source fluid density sensor.

Based on the determined effluent density value, the method can continue with determining a quantity (e.g., a volume) of effluent pumped through the effluent line into the effluent receptacle at step 1306. In some examples, determining the quantity of effluent pumped can include measuring an effluent weight value of the effluent receptacle with the effluent scale as in step 1314. Then, determining the quantity of effluent pumped is based on the determined effluent density value and the effluent weight value.

Additionally, based on the determined source fluid density value, the method can continue with determining a quantity (e.g., a volume) of source fluid pumped through the source fluid line from the source fluid reservoir at step 1308. In some examples, determining the quantity of source fluid pumped can include measuring a source fluid weight value of the source fluid reservoir with the source fluid scale as in step 1316. Then, determining the quantity of source fluid pumped is based on the determined source fluid density value and the source fluid weight value.

After determining the quantity of effluent and source fluid pumped, the method continues at step 1310 with outputting a system control signal based on the determined quantity of effluent and source fluid pumped.

Optionally, the method can further continue at step 1318 with operating the source fluid pump to pump a priming fluid from a priming fluid reservoir through the source fluid line during a priming operation. The method further continues with using the source fluid scale to measure a priming fluid weight value of the priming fluid reservoir during the priming operation at step 1320. Next, in step 1322, the method includes determining a source fluid pump rate during the priming operation based on the priming fluid weight value and a known priming fluid density value. Once the source fluid pump rate is determined, the method can continue with operating the source fluid pump in a standard operation and then using the source fluid scale to measure a source fluid weight value of the source fluid reservoir during the standard operation at step 1324. Lastly, in step 1326, the method includes determining the source fluid density value during standard operation based on the source fluid weight value and the source fluid pump rate. A similar method can be employed to determine an effluent pump rate during the priming operation and determining the effluent density value during standard operation based on an effluent weight value and the effluent pump rate.

While the steps of FIG. 13 may be illustrated and discussed in a particular order, it will be appreciated that the steps of FIG. 13 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps. Moreover, while some steps are illustrated with dotted lines to indicate they are optional, in some examples, steps illustrated with solid lines can also be optional.

Figure 14:
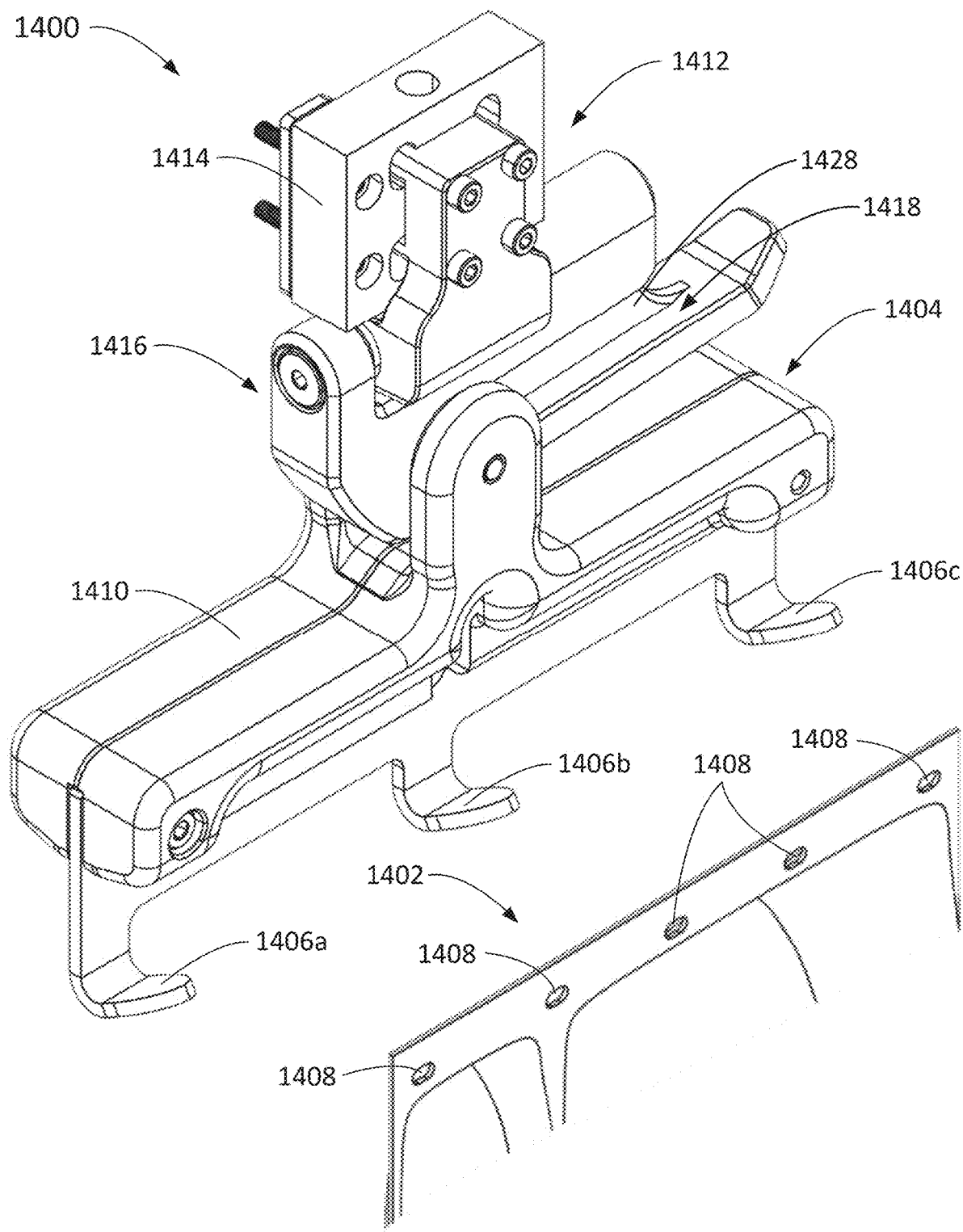
FIG. 14 is a perspective view of an example apparatus for hanging a medical fluid container and a perspective view of a portion of the medical fluid container according to an aspect of the present disclosure.
Figure 15:
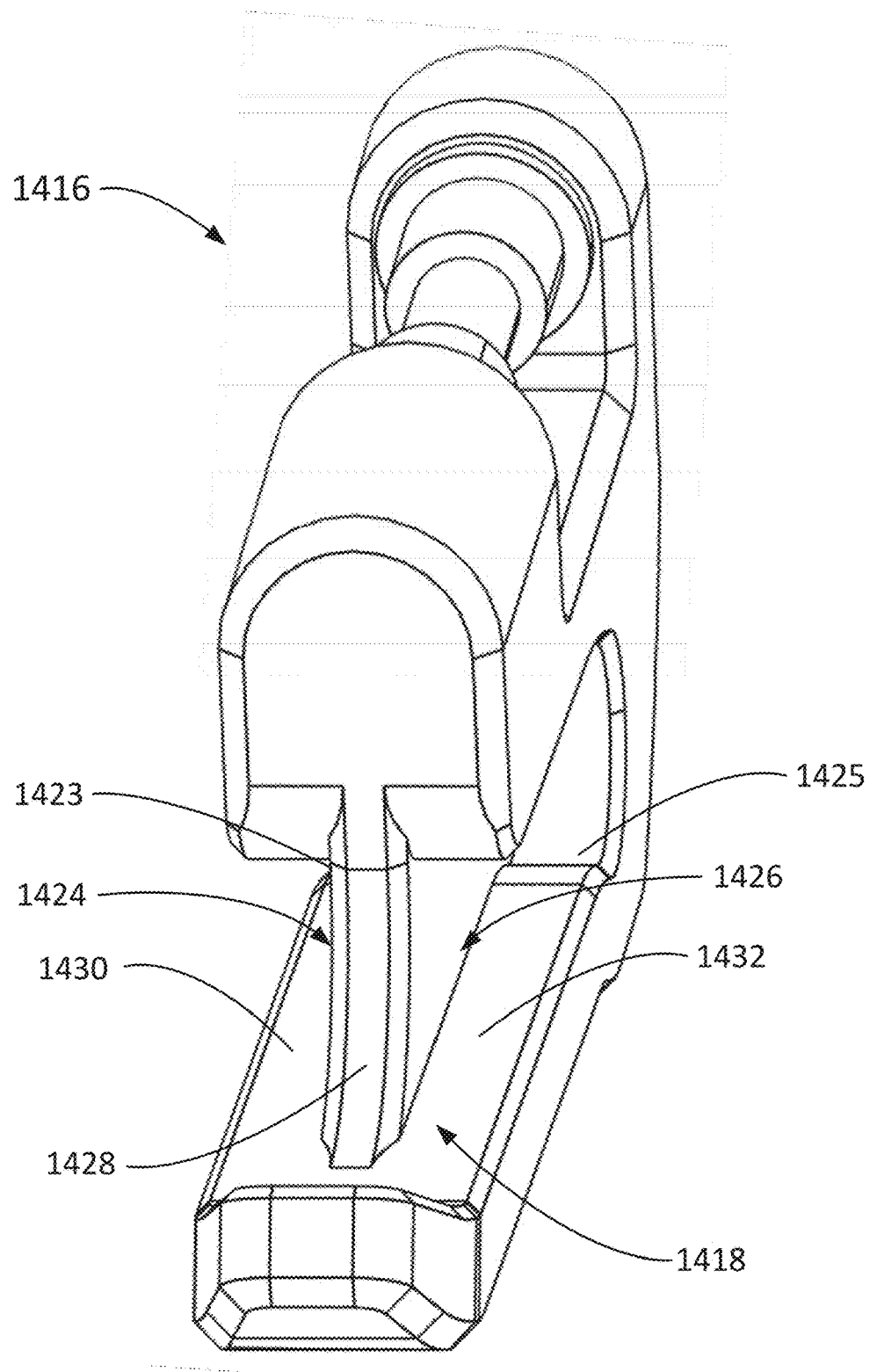
FIG. 15 is a perspective view of a rail assembly of the apparatus of FIG. 14 according to an aspect of the present disclosure.
Figure 16:
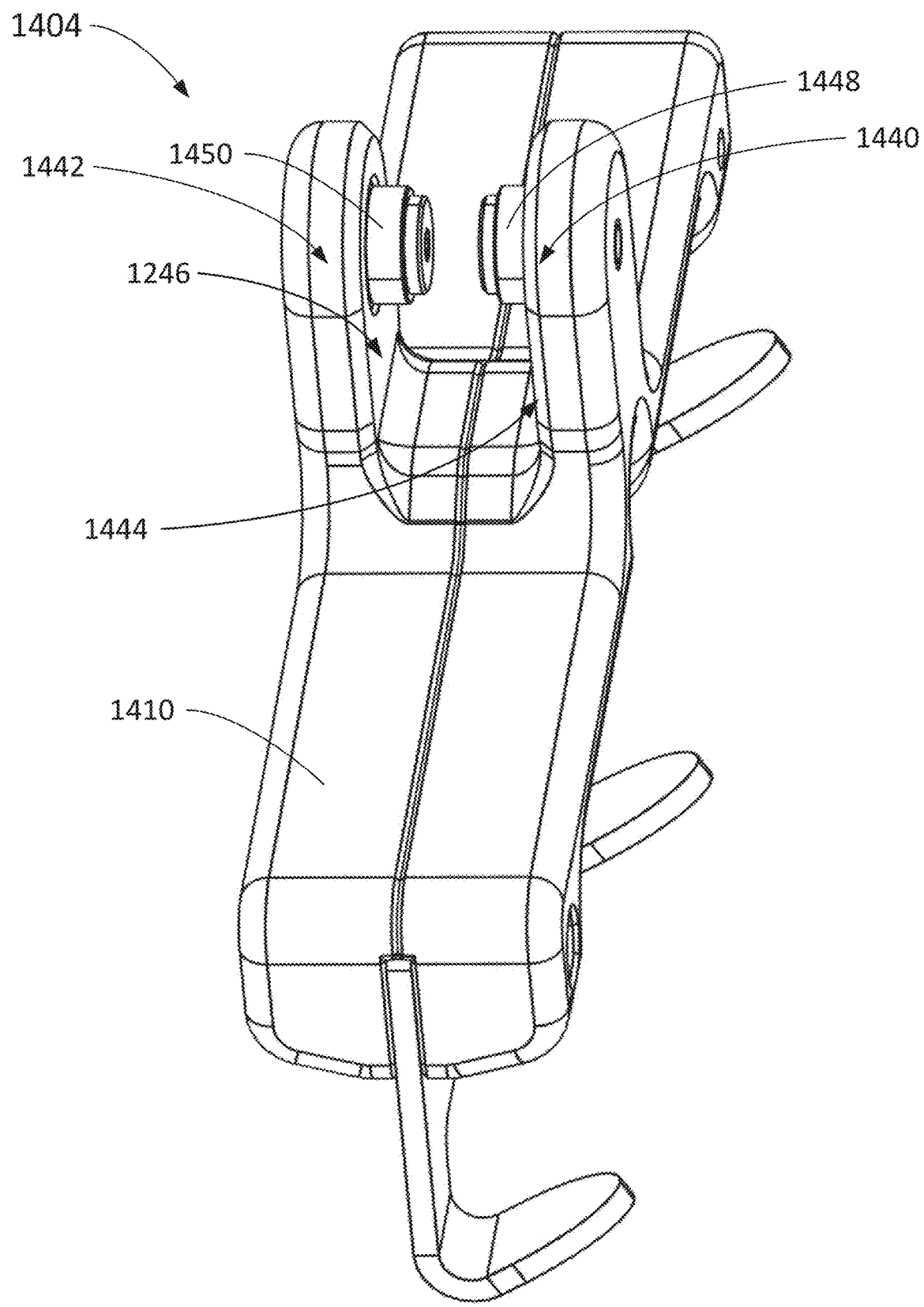
FIG. 16 is a perspective view of a hanger of the apparatus of FIG. 14 according to an aspect of the present disclosure.
Figure 17:
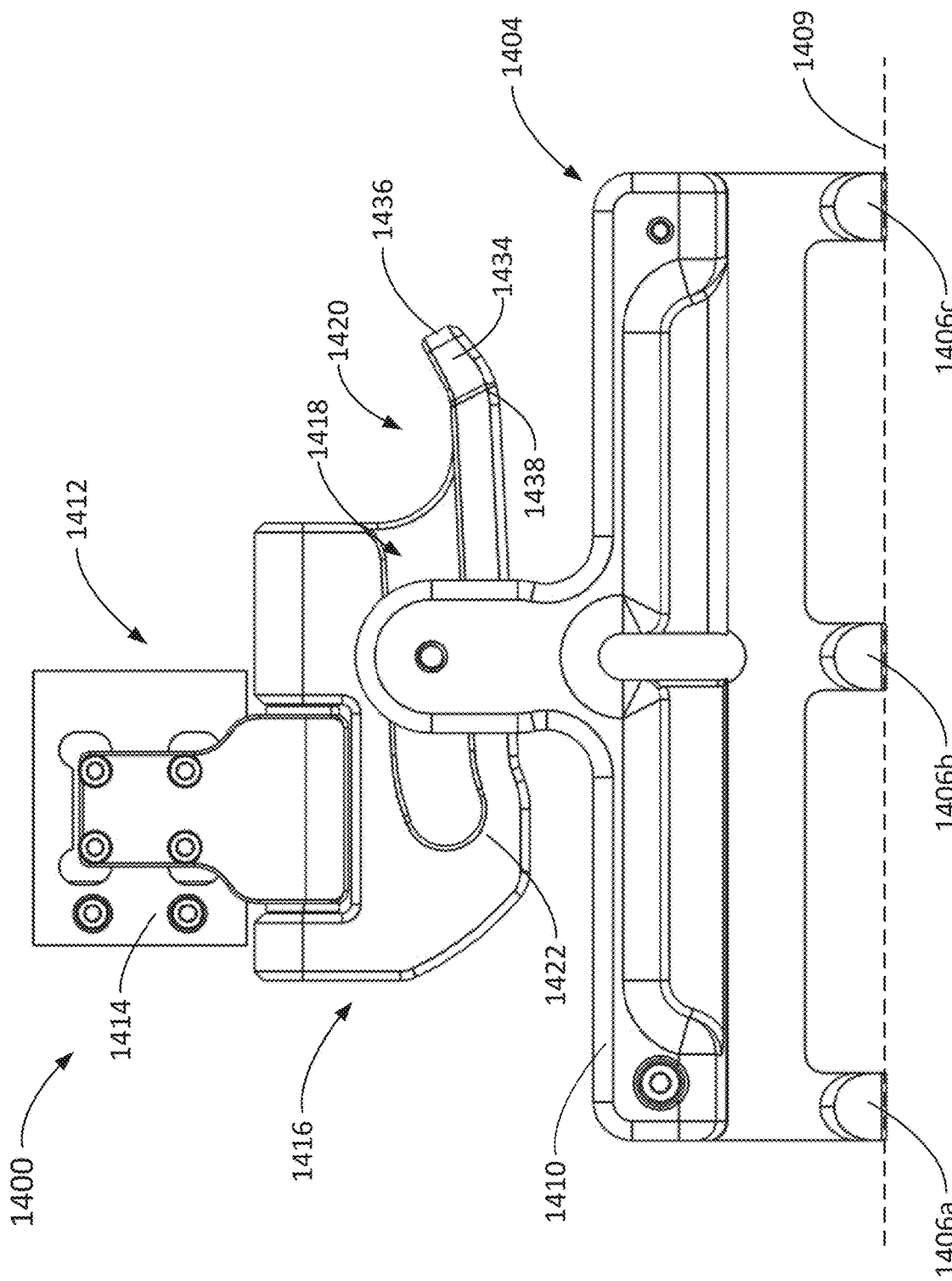
FIG. 17 is a front perspective view of the example apparatus of FIG. 14 with a hanger being slightly translated on the apparatus according to an aspect of the present disclosure.
Figure 18:
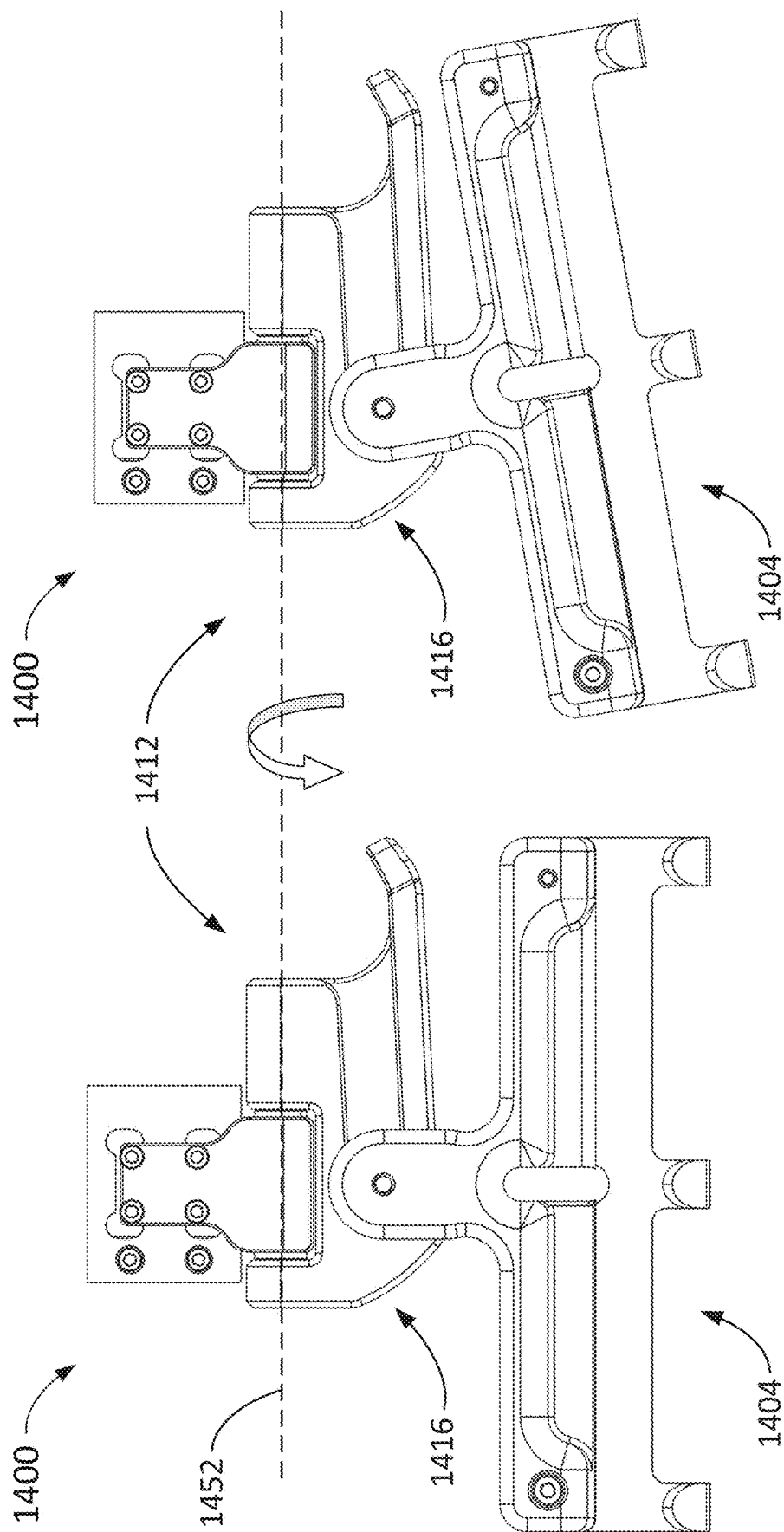
FIG. 18A and FIG. 18B are front perspective views of the example apparatus of FIG. 14 illustrating the example apparatus being rotated about an axis.
Figure 19:
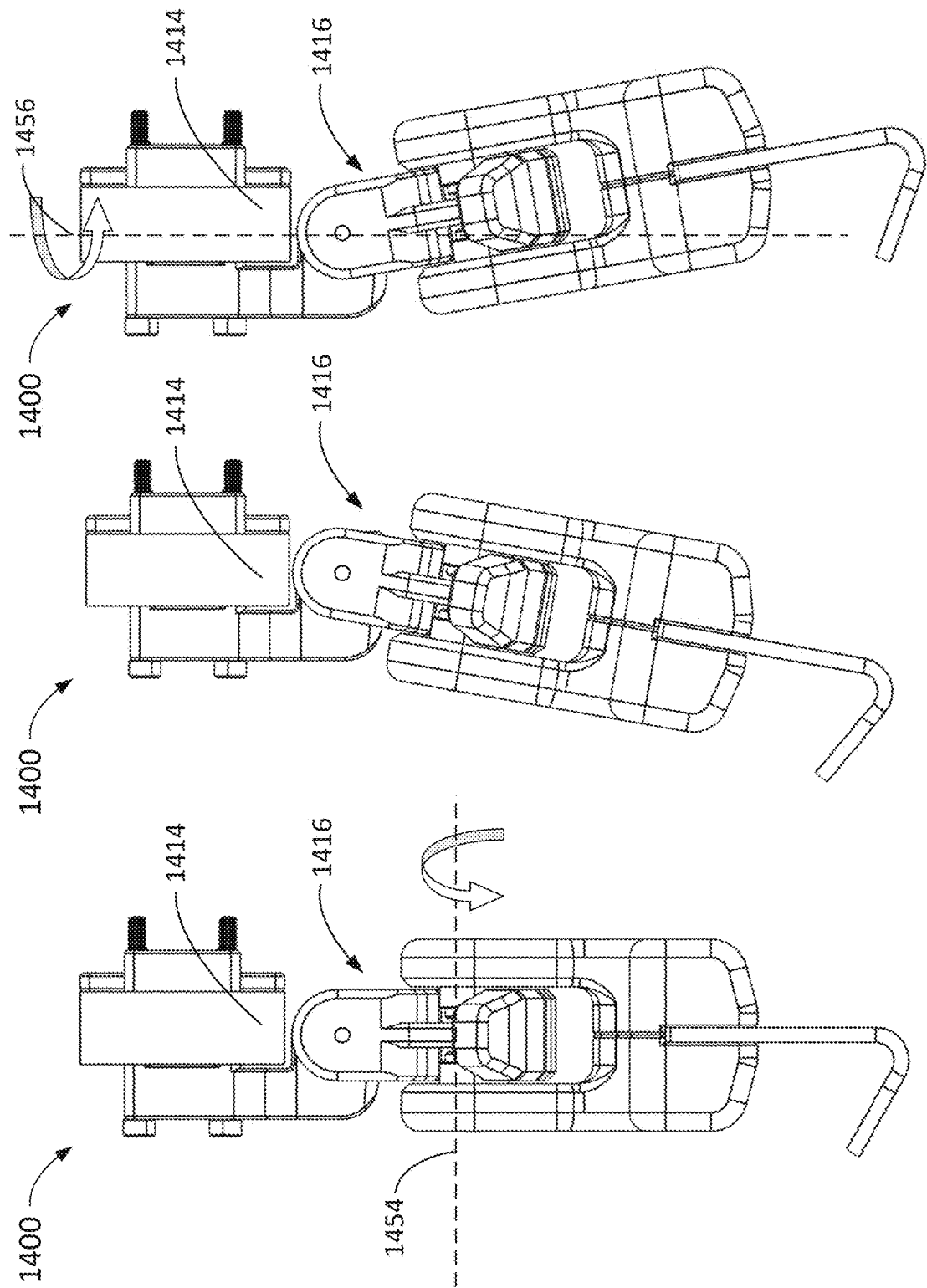
FIG. 19A, FIG. 19B, and FIG. 19C are side perspective views of the example apparatus of FIG. 14 illustrating the example apparatus being rotated about another axis.

Now referencing FIGS. 14-19C, FIGS. 14-19C include various views of an apparatus 1400 for hanging a medical fluid container 1402. FIG. 14 is a perspective view of an example apparatus 1400 for hanging the medical fluid container 1402 and a perspective view of a portion of the medical fluid container 1402. FIG. 15 is a perspective view of just the rail assembly 1416 of FIG. 14. FIG. 16 is a perspective view of just the hanger 1404 of FIG. 14. FIG. 17 is a front perspective view of the example apparatus 1400 of FIG. 14 with a hanger 1404 being slightly translated on the apparatus 1400. FIGS. 18A-18B are front perspective views of the example hanger of FIG. 14 illustrating the example apparatus 1400 being rotated about an axis. FIGS. 19A-19C are side perspective views of the example apparatus 1400 of FIG. 14 illustrating the example apparatus 1400 being rotated about another axis. In preferred embodiments, an apparatus for hanging a medical fluid container will enable the medical fluid container to self-align with a weight scale (e.g., by permitting the medical fluid container to pivot about one or more horizontal axes and by preventing rotation of the medical fluid container about a vertical axis, which can cause the medical fluid container to become tangled and prevent self-alignment.

In the illustrated embodiments, the hanger 1404 of the apparatus 1400 is configured to hang the medical fluid container 1402, which in some examples, can include a medical fluid bag (e.g., saline bag). To hold the medical fluid container 1402, the hanger 1404 includes one or more hooks 1406a, 1406b, 1406c configured to engage one or more holes 1408 of the medical fluid container 1402. In some embodiments, the hanger 1404 includes three hooks, which comprise a first hook 1406a, a second hook 1406b, and a third hook 1406c. The first hook 1406a can be spaced apart from the second hook 1406b by approximately 3 inches, and the second hook 1406b can be spaced apart from the third hook 1406c by approximately 3 inches. As illustrated in FIG. 17, the first hook 1406a, the second hook 1406b, and the third hook 1406c can be aligned along a horizontal axis 1409. In some embodiments, such as in FIG. 14, the medical fluid container 1402 includes three or more holes 1408. In some such embodiments, three of the three or more holes 1408 are secured to the three hooks 1406a, 1406b, 1406c, while other holes remain unsecured and/or are doubled up on the same hooks.

In addition to the hanger 1404, the apparatus 1400 includes a bracket 1412 configured to attach to an extracorporeal blood filtering machine (e.g., extracorporeal blood filtering machine 1202). The bracket 1412 can include a mount 1414, which includes one or more fasteners (e.g., screws, clips) to secure the bracket 1412, and the overall apparatus 1400, to the extracorporeal blood filtering machine.

The bracket 1412 is also configured to removably connect the hanger 1404 to the extracorporeal blood filtering machine. For example, the bracket 1412 comprises a rail assembly 1416 with a rail 1418 onto which the attachment member 1410 of the hanger 1404 secures. In general, the hanger 1404 can connect with the bracket 1412. More specifically, the attachment member 1410 of the hanger 1404 is configured to fit into the rail 1418 and slide along the rail 1418 to connect with the rail 1418 of the bracket 1412.

As illustrated in FIG. 17, the rail 1418 of the rail assembly 1416 includes an inlet 1420 configured to receive the hanger 1404. The attachment member 1410 of the hanger 1404 can insert into the inlet 1420 and slide along the rail 1418. The bracket 1412 further includes a seat 1422, with the seat 1422 being on one end of the bracket 1412 and the inlet 1420 being on an opposite end of the bracket 1412. The seat 1422 extends lower on the bracket 1412 than the inlet 1420, which can enable the attachment member 1410 of the hanger 1404 to slide along the rail 1418 to the seat 1422 and to be seated in the seat 1422. In some examples, the rail 1418 can form a declined angle with the horizontal, which can aid in the attachment member 1410 sliding to the seat 1422.

Now referencing FIG. 15, the bracket 1412, and specifically the rail assembly 1416, can comprise two sides. Each of the two sides can be approximately the same shape and include many of the same features. In general, each side of the bracket 1412 is configured to enable the hanger 1404 to connect to the bracket 1412. In some examples, the two sides are bonded together to produce the bracket 1412.

Starting with the seat 1422, the seat 1422 can comprise a first seat 1423 (e.g., on a first side) and a second seat 1425 (e.g., on a second side) separated by a center wall 1428.

Continuing with the rail 1418, the rail 1418 can include a first rail side 1424 and a second rail side 1426 that are separated by the center wall 1428. The first rail side 1424 can extend between the inlet 1420 and the first seat 1423, while the second rail side 1426 can extend between the inlet 1420 and the second seat 1425. The first rail side 1424 can comprise a first lower wall 1430, while the second rail side 1426 can comprise a second lower wall 1432.

Now referencing both FIG. 15 and FIG. 17, the inlet 1420 of the rail 1418 can include a lip 1434 extending from the first lower wall 1430 and the second lower wall 1432. The lip 1434 can be angled upward from the first lower wall 1430 and the second lower wall 1432 and can be used to guide the attachment member 1410 to secure the attachment member 1410 to the rail 1418. In some embodiments, the lip 1434 can include a tip 1436 and a base 1438 with the tip 1436 being narrower than the base 1438. This can help in aligning the hanger 1404 with the lip 1434.

Referencing FIG. 16, the hanger 1404, and specifically the attachment member 1410, can also comprise two sides. Each of the two sides can be approximately the same shape and include many of the same features. The two sides can be used to enable the attachment member 1410 to connect to the bracket 1412. The attachment member 1410 can comprise a first attachment member 1440 (e.g., on a first side) and a second attachment member 1442 (e.g., on a second side). The first attachment member 1440 is configured to slide along the first rail side of the bracket 1412, contact the first lower wall of the bracket 1412 while sliding, and settle (e.g., be seated) in the first seat. The second attachment member 1442 is configured to slide along the second rail side of the bracket 1412, contact the second lower wall of the bracket 1412 while sliding, and settle (e.g., be seated) in the second seat.

The attachment member 1410 includes a first side wall 1444 on one side and a second side wall 1446 on the other side. The first side wall 1444 can be positioned near the first rail side 1424 when the attachment member 1410 is sliding along the rail 1418. Additionally, the second side wall 1446 can be positioned near the second rail side 1426 when the attachment member 1410 is sliding along the rail 1418.

The attachment member 1410 also includes a first protrusion 1448 extending from the first side wall 1444 toward the second side wall 1446 and a second protrusion 1450 extending from the second side wall 1446 toward the first side wall 1444. The first protrusion 1448 can be configured to contact the first lower wall 1430 of the rail 1418 to enable the attachment member 1410 to slide along the first rail side 1424. Additionally, the second protrusion 1450 can be configured to contact the second lower wall 1432 of the rail 1418 to enable the attachment member 1410 to slide along the second rail side 1426. In some embodiments, the first protrusion 1448 includes a first bearing configured to roll along the first lower wall 1430 and the second protrusion 1450 includes a second bearing configured to roll along the second lower wall 1432. The bearings can reduce the friction between the protrusions 1448, 1450 and the lower walls 1430, 1432 of the rail 1418, enabling smoother movement.

In some embodiments, the lip 1434 of the rail 1418 is configured to contact the first side wall 1444 and the second side wall 1446 of the attachment member 1410 to guide the first protrusion 1448 into contact with the first lower wall 1430 and to guide the second protrusion 1450 into contact with the second lower wall 1432. In some examples, the tip 1436 of the lip 1434 is narrower than the base 1438 to align the first side wall 1444 and the second side wall 1446 of the attachment member 1410 as the attachment member 1410 is fitted into the inlet 1420 of the rail 1418.

Now referencing FIGS. 18A-18B and FIGS. 19A-19C, the hanger 1404 is configured to align the medical fluid container 1402 with a scale (e.g., 1248 of FIG. 12) of the extracorporeal blood filtering machine when the attachment member 1410 is fit into the inlet 1420 of the rail 1418. In some examples, the hanger 1404 is configured to align the medical fluid container 1402 with the scale by hanging the medical fluid container 1402 directly under, and vertically in line with, the scale. This can ensure the scale receives an accurate reading when it weighs the medical fluid container as the weight is pulling directly downward without tilting in a direction.

In the illustrated embodiments, the hanger 1404 and the bracket 1412 are configured to permit the medical fluid container 1402 to pivot about a first horizontal axis 1452 and a second horizontal axis 1454 that differs from the first horizontal axis 1452. This pivoting can enable the medical fluid container 1402 to hang directly under, and vertically in line with, the scale as the hanger 1404 and medical fluid container 1402 can pivot relative to the extracorporeal blood filtering device. In this way, the medical fluid container 1402 can self-align with the scale. While the hanger 1404 and the bracket 1412 are configured to permit the medical fluid container 1402 to pivot about the first horizontal axis 1452 and a second horizontal axis 1454, the hanger 1404 and the bracket 1412 can prevent the medical fluid container 1402 from pivoting about a vertical axis 1456. Pivoting about the vertical axis is illustrated by the arrow in FIG. 19C. Pivoting about a vertical axis 1456 can be disadvantageous as such rotation can, for example, cause the medical fluid container to contact other devices, tubing, sensor contacts or the like, which can result in misalignment and/or erroneous weight scale measurements.

In FIGS. 18A-18B, even though the first horizontal axis 1452 is illustrated, the hanger 1404 pivots about the second horizontal axis 1454, which is illustrated in FIGS. 19A-19C. The second horizontal axis 1454, if illustrated in FIG. 18A/B, would go into the page at the center point of the protrusions 1448, 1450 of the hanger 1404. The hanger 1404, when the attachment member 1410 is seated in the seat 1422, is configured to pivot relative to the rail assembly 1416 of the bracket 1412 about the second horizontal axis 1454. This pivot of the hanger 1404 is illustrated in FIG. 18B and by the arrow found in FIG. 19A. While the hanger 1404 is only illustrated as pivoting such that a right side of the hanger is raised higher relative to the left side of the hanger, the hanger 1404 can pivot in the other direction. In some examples, though, pivoting the hanger 1404 such that the left side raises and the right side lowers, can result in the hanger 1404 sliding out of the seat 1422 and toward the inlet 1420. However, in some such examples, the raised lip 1434 can prevent the hanger 1404 from completely sliding off of the bracket 1412.

In FIGS. 19A-19C, even though the second horizontal axis 1454 is illustrated, the rail assembly 1416 pivots about the first horizontal axis 1452, which is illustrated in FIGS. 18A-18B. The first horizontal axis 1452, if illustrated in FIGS. 19A-19C, would go into the page at the center point of the rail assembly's 1416 connection to the mount 1414. The rail assembly 1416 is configured to pivot relative to the mount 1414 about the first horizontal axis 1452. This pivot is illustrated in FIGS. 19B-19C, and by the arrow found in FIGS. 18A-18B.

The ability of the hanger 1404 to pivot relative to the rail assembly 1416, along with ability of the rail assembly 1416 to pivot relative to the mount 1414, enables the hanger 1404 and the attached medical fluid container 1402 to stay directly under the mount 1414. Because the mount 1414 is attached to the extracorporeal blood filtering machine, and can be specifically attached to a scale, the hanger 1404 and the attached medical fluid container 1402 can be aligned (e.g., directly under and vertically in line) with the scale.

Figure 20:
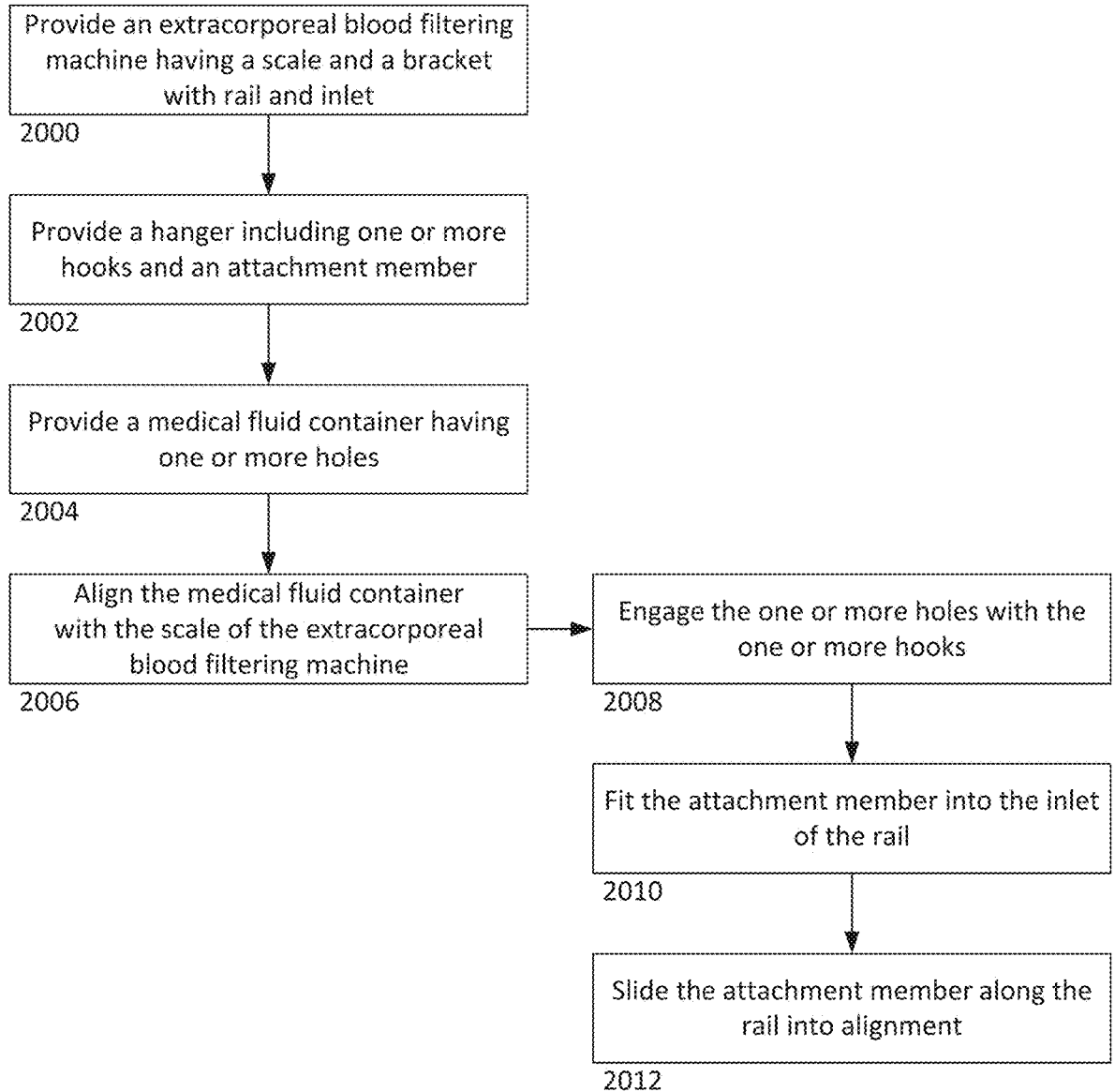
FIG. 20 is a flowchart of an example operation of the apparatus of FIG. 14 according to an aspect of the present disclosure.

Moving to FIG. 20, FIG. 20 is a flowchart of an example operation of the apparatus 1400 of FIG. 14 according to an aspect of the present disclosure. The method starts at step 2000 with providing an extracorporcal blood filtering machine that includes a scale and a bracket having a rail and an inlet. The method also includes providing a hanger that includes one or more hooks and an attachment member as in step 2002. The method further includes providing a medical fluid container having one or more holes as in step 2004. Next, the method includes aligning the medical fluid container with the scale of the extracorporeal blood filtering as in step 2006. The aligning step can itself include the steps of 2008 through 2012. In step 2008, the method includes engaging the one or more holes of the medical fluid container with the one or more hooks of the hanger to hang the medical fluid container onto the hanger. Next, in step 2010, the method includes fitting the attachment member into the inlet of the rail. Further, in step 2012, the method includes sliding the attachment member along the rail into alignment. In some embodiments, aligning the medical fluid container with the scale of the extracorporeal blood filtering machine comprises hanging the medical fluid container directly under and vertically in line with the scale.

While the steps of FIG. 20 may be illustrated and discussed in a particular order, it will be appreciated that the steps of FIG. 20 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps. Moreover, while some steps are illustrated with dotted lines to indicate they are optional, in some examples, steps illustrated with solid lines can also be optional.

Figure 21:
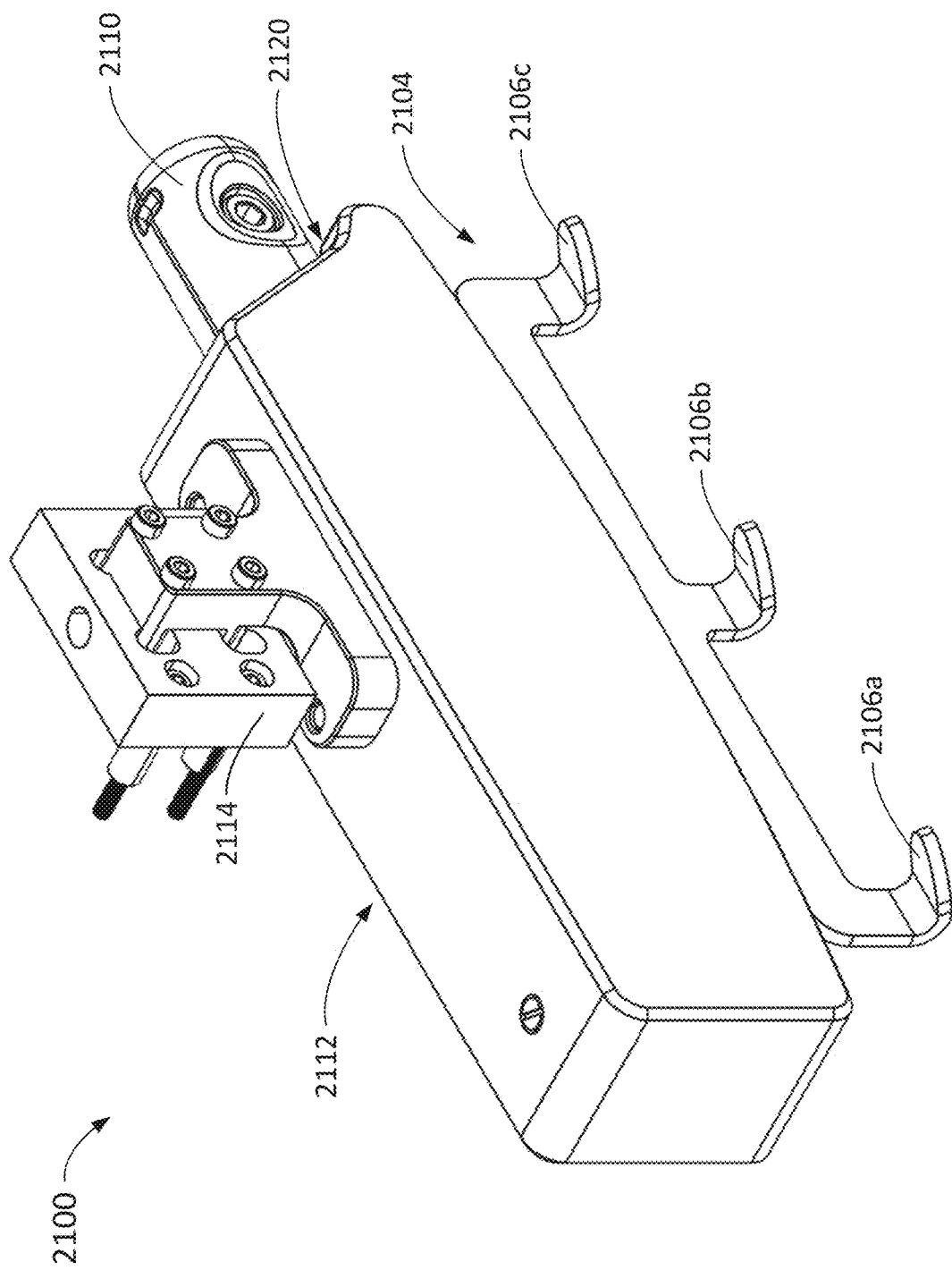
FIG. 21 is a perspective view of an alternate example apparatus for hanging a medical fluid container according to an aspect of the present disclosure.
Figure 22:
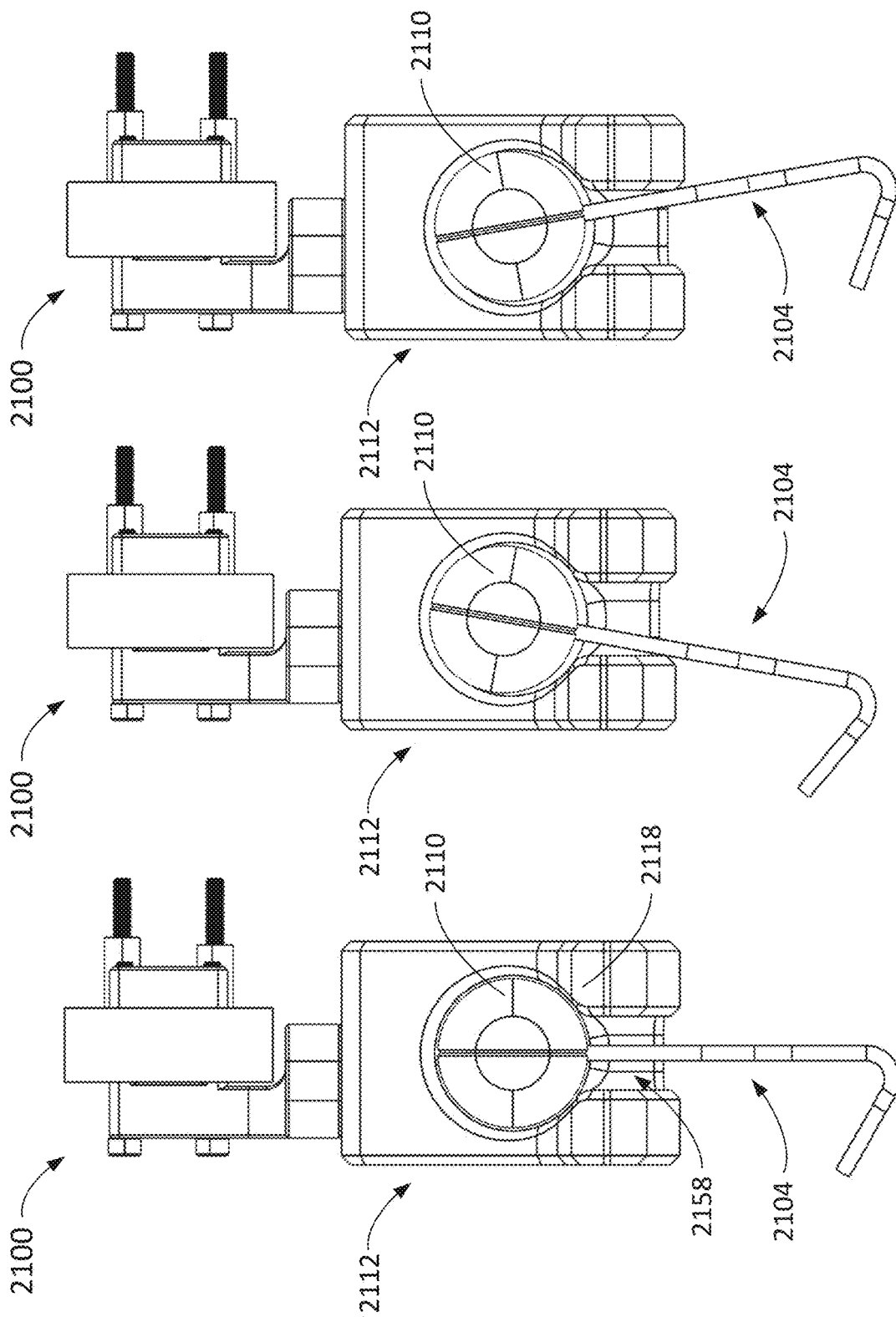
FIG. 22A, 22B, 22C are side perspective views of the apparatus of FIG. 21 illustrating the example apparatus being rotated about an axis according to an aspect of the present disclosure.
Figure 23:
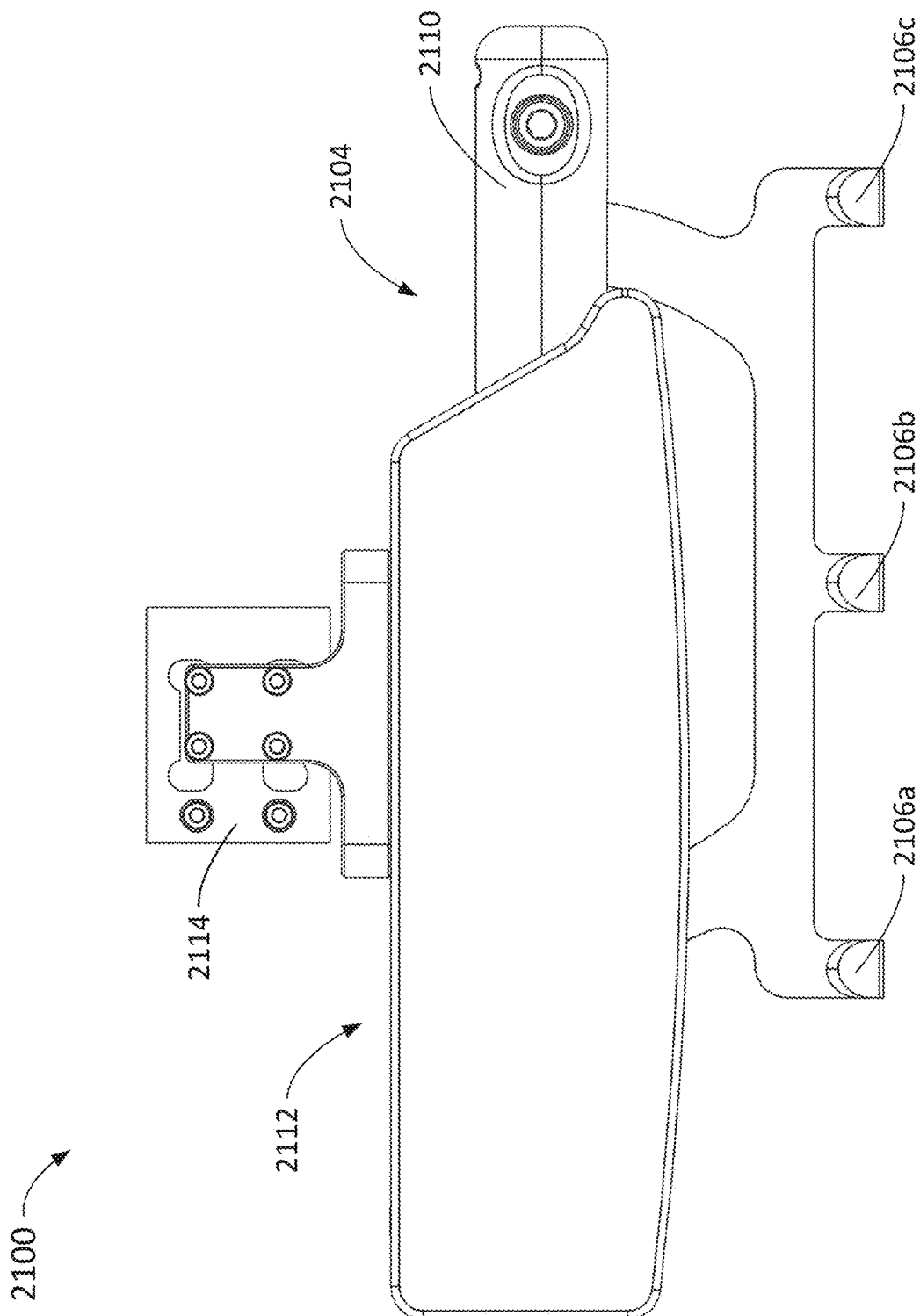
FIG. 23 is a front perspective view of the apparatus of FIG. 21 with a hanger being slightly translated on the apparatus according to an aspect of the present disclosure.
Figure 24:
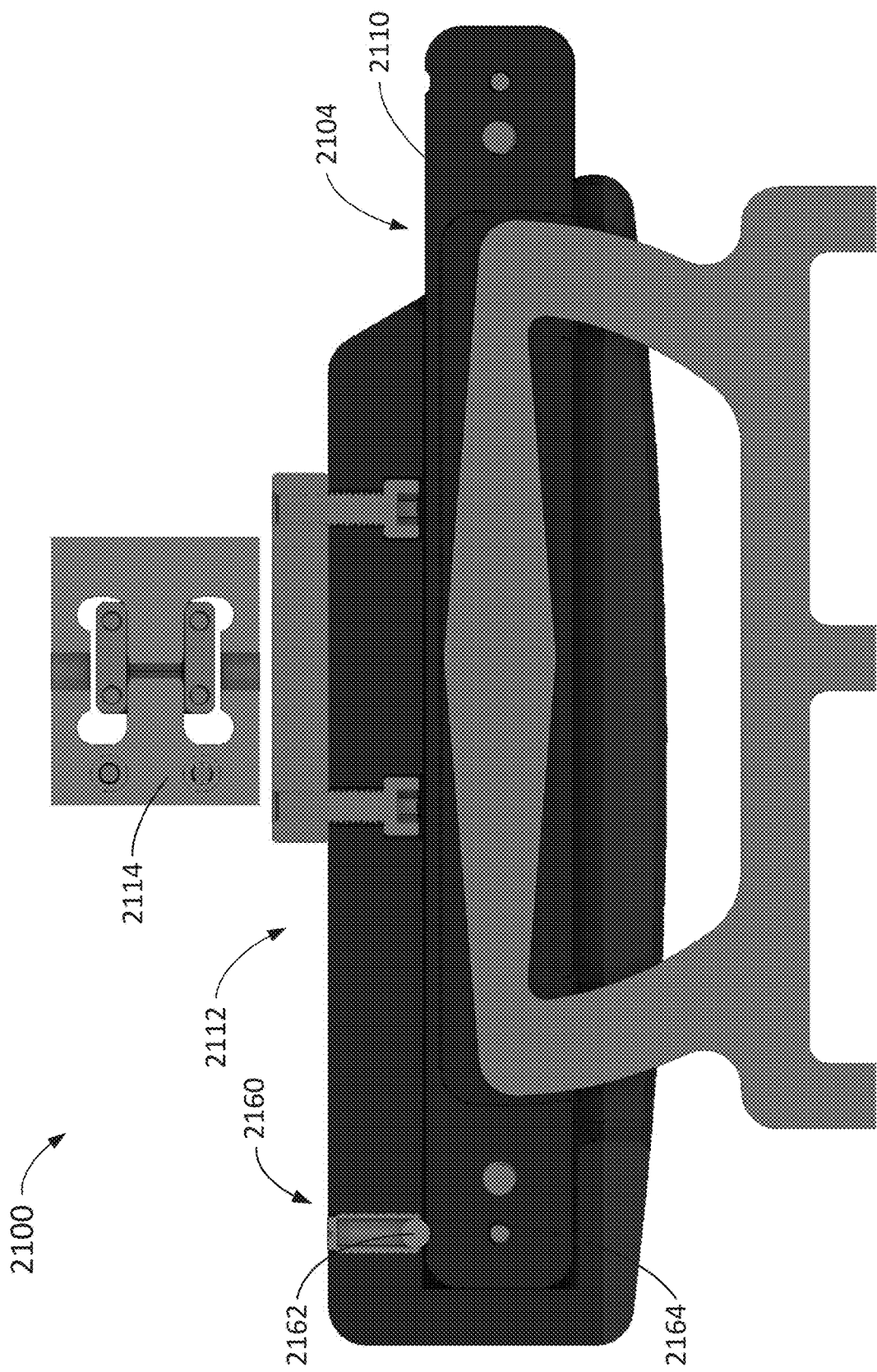
FIG. 24 is a front sectional view of the apparatus of FIG. 21 according to an aspect of the present disclosure.

Now referencing FIGS. 21-24, FIGS. 21-24 are views of an alternate apparatus 2100 for hanging a medical fluid container (e.g., 1402 of FIG. 14) according to aspects of the present disclosure. FIG. 21 is a perspective view of the apparatus 2100 for hanging a medical fluid container. FIGS. 22A-22C are side perspective views of the apparatus of FIG. 21 illustrating the example apparatus being rotated about an axis. FIG. 23 is a front perspective view of the apparatus of FIG. 21, with a hanger being slightly translated on the apparatus 2100. FIG. 24 is a front sectional view of the apparatus of FIG. 21.

The apparatus 2100 includes a hanger 2104 configured to hang a medical fluid container (e.g., 1402 of FIG. 14). The hanger 2104 includes one or more hooks 2106a, 2106b, 2106c, which are configured to engage one or more holes (e.g., 1408) in the medical fluid container (e.g., 1402). The hanger 2104 also includes an attachment member 2110.

The apparatus 2100 further includes a bracket 2112 configured to attach to an extracorporeal blood filtering machine. The bracket 2112 can include a mount 1414, which is used to secure to the extracorporeal blood filtering machine. The bracket 2112 also includes a rail 2118 with an inlet 2120, with the attachment member 2110 of the hanger 2104 configured to fit into the inlet 2120 of the rail 2118 and slide along the rail 2118. In this configuration, the hanger 2104 is configured to align the medical fluid container with a scale of the extracorporeal blood filtering machine when the attachment member 2110 is fit into the inlet 2120 of the rail 2118.

The bracket 2112 can also define an attachment member opening 2158 with a bottom of the attachment member opening 2158 being defined by the rail 2118. The attachment member 2110 can be inserted into the attachment member opening 2158 and slidable contact the rail 2118. When the attachment member 2110 is inserted into the attachment member opening 2158, the one or more hooks 2106a, 2106b, 2106c of the hanger 2104 protrude downward through the attachment member opening 2158. As illustrated in FIGS. 22A-22C, the attachment member opening 2158 includes space on either side of the one or more hooks 2106a, 2106b, 2106c. This configuration can enable the hanger 2104, which includes the attachment member 2110, to pivot relative to the bracket 2112 about a first axis. Further, the attachment member 2110 can be configured to slide along the rail on a second axis, as illustrated in FIG. 23. The ability of the hanger to pivot relative to the bracket and to further slide along the rail can keep a medical fluid container hooked on the hanger to remain under a scale of an extracorporeal blood filtering machine. This can help maintain the accuracy of the scale despite the extracorporeal blood filtering machine being on an incline, for example.

Now referencing FIG. 24, the bracket 2112 can comprise a locking mechanism 2160 which is configured to prevent the attachment member 2110 from sliding relative to the bracket 2112 when the attachment member 2110 is in a first position. The first position is illustrated in FIG. 24 and comprises the attachment member 2110 being fully inserted into the attachment member opening 2158. The locking mechanism 2160 includes a portion of the bracket 2112 and a portion of the attachment member 2110. The bracket 2112 comprises a protruding member 2162 at an opposite end while the attachment member 2110 comprises a detent 2164 at an attachment member end. The protruding member 2162 is configured to insert into the detent 2164 and prevent the attachment member 2110 from sliding within the attachment member opening 2158. However, because the protruding member 2162 can comprise a bearing, and because the detent 2164 can extend slightly around a circumference of the attachment member 2110, the locking mechanism 2160 does not prevent the attachment member 2110 from pivoting relative to the bracket 2112 about a first axis.

Figure 25:
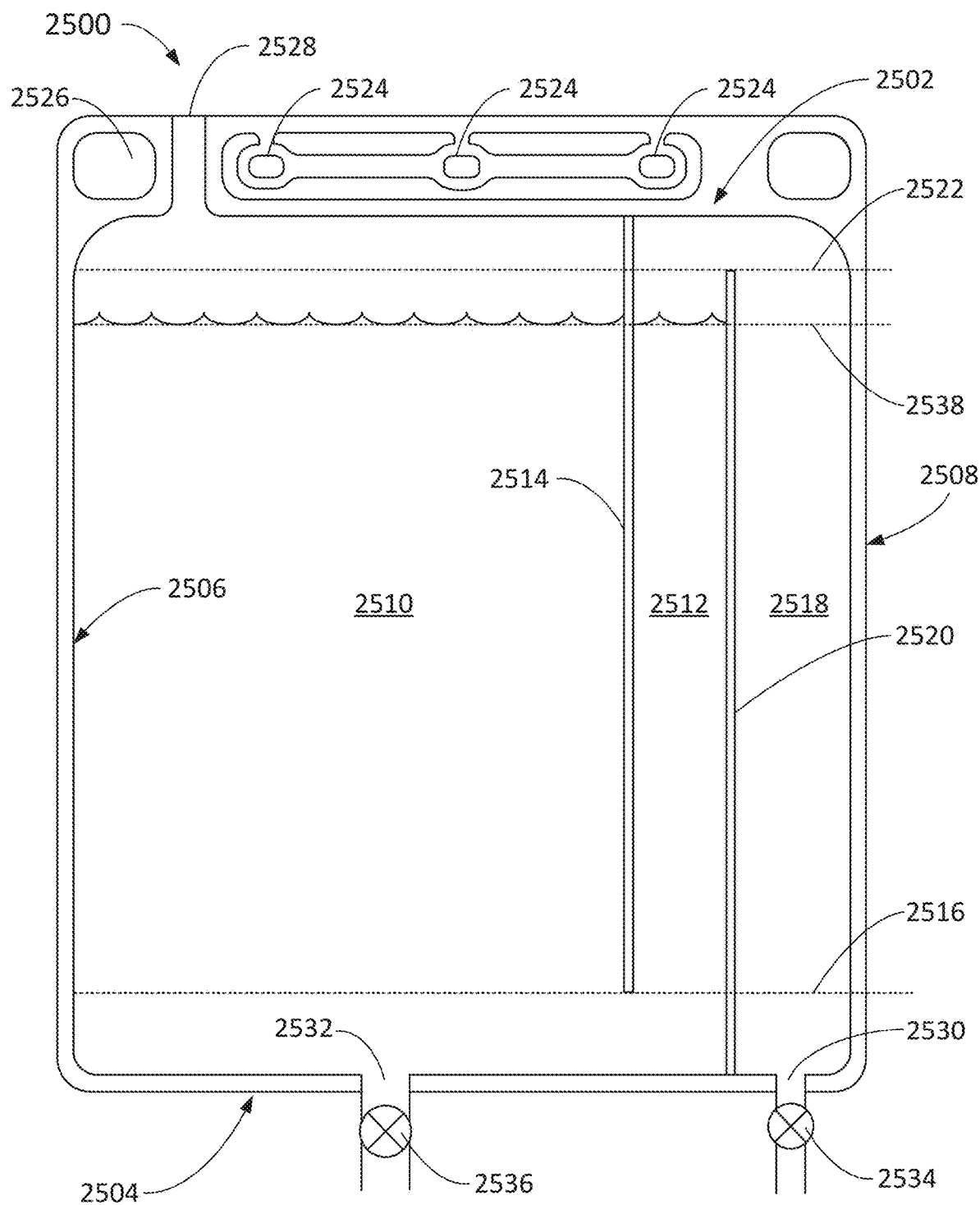
FIG. 25 is a front view of an example medical fluid container according to an aspect of the present disclosure.

Moving to FIG. 25, FIG. 25 is a front view of an example medical fluid container 2500 according to an aspect of the present disclosure. In operation, the medical fluid container 2500 is configured to receive a fluid and to subsequently empty the fluid automatically once the fluid reaches a specific level (e.g., full). In some examples, the received fluid is effluent, such as the effluent generated from filtering blood as described elsewhere herein.

The medical fluid container 2500 has a top 2502, a bottom 2504, and two sides 2506, 2508. The medical fluid container 2500 includes a primary chamber 2510 configured to hold a fluid and a secondary chamber 2512, in fluid communication with the primary chamber 2510, which is also configured to hold the fluid. The secondary chamber 2512 is partially separated from the primary chamber 2510 by a first wall 2514 that extends from the top 2502 of the medical fluid container to an empty-level 2516 near the bottom 2504 of the medical fluid container. As illustrated, the primary chamber 2510 is larger than the secondary chamber 2512. In some embodiments, the secondary chamber 2512 is the same size as or larger than the primary chamber 2510.

The medical fluid container 2500 further includes a discharge chamber 2518 in fluid communication with the secondary chamber 2512. The discharge chamber 2518 is partially separated from the secondary chamber 2512 by a second wall 2520 that extends from the bottom 2504 of the medical fluid container 2500 to a full-level 2522 near the top 2502 of the medical fluid container 2500. In the illustrated embodiment, the discharge chamber 2518 is formed by the second wall 2520 and the right side 2508 exterior wall of the medical fluid container 2500. In some embodiments, the discharge chamber 2518 is formed by the second wall 2520 and another interior wall (e.g., a third wall), or an alternate exterior wall (e.g., left side 2506 wall).

The medical fluid container 2500 can be made of one or more materials. In some examples, the medical fluid container 2500 is made from a single material. For instance, in some examples, the primary chamber 2510, the secondary chamber 2512, the discharge chamber 2518, the first wall 2514, and the second wall 2520 are all formed of the same material. However, in some examples, the medical fluid container 2500 is made from multiple materials.

Continuing with FIG. 25, the medical fluid container 2500 can define a series of holes 2524, which can be used to hang the medical fluid container 2500. For instance, in some examples, the apparatus described with respect to FIGS. 14-19C can be used to hang the medical fluid container 2500 by using its one or more hooks to engage the series of holes 2524. The medical fluid container 2500 can further define one or more corner holes 2526, which can also be used to hang the medical fluid container 2500.

To fill/add fluid, the medical fluid container 2500 includes a fill port 2528. The fill port 2528 is fluidly connected to the primary chamber 2510 and is configured to receive a fluid in order for the fluid to reach the primary chamber 2510. In some examples, the fill port 2528 engages with tubing to receive fluid. In some embodiments, the medical fluid container includes integrated tubing that is in fluid communication with the fill port 2528 to receive fluid.

To drain/remove fluid, the medical fluid container 2500 includes a first drain port 2530 and a second drain port 2532. The first drain port 2530 is in fluid communication with the discharge chamber 2518 and leads to a first drain valve 2534. Thus, the first drain valve 2534 is also in fluid communication with the discharge chamber 2518. The first drain port 2530 and the first drain valve 2534 can be located proximate the bottom 2504 of the medical fluid container 2500. The first drain valve 2534 is configured to control emptying/draining of any fluid within the discharge chamber 2518 and can be in an open or closed position.

Similarly, the second drain port 2532 is in fluid communication with the primary chamber 2510 and leads to a second drain valve 2536. Thus, the second drain valve 2536 is also in fluid communication with the primary chamber 2510. The second drain port 2532 and the second drain valve 2536 can also be located proximate the bottom 2504 of the medical fluid container 2500. The second drain valve 2536 is configured to control emptying of any fluid within the primary chamber 2510 and by extension, any fluid within the secondary chamber 2512 as the secondary chamber 2512 is in fluid communication with the primary chamber 2510. The second drain valve 2536 can be in an open or closed position. While the illustrated embodiment of FIG. 25 includes a second drain port 2532 and second drain valve 2536, in some embodiments, the medical fluid container only includes the first drain port 2530 and the first drain valve 2534, and in some embodiments, the medical fluid container includes multiple drain ports and drain valves.

In an example operation of the medical fluid container 2500, fluid is received by the medical fluid container 2500 via the fill port 2528 and stored in the primary chamber 2510 and the secondary chamber 2512. As more fluid is received and stored in the primary chamber 2510 and the secondary chamber 2512, the fluid level (e.g., 2538) within the primary chamber 2510 and the secondary chamber 2512 rises accordingly. However, once the fluid level rises above the full-level 2522 of the second wall 2520, fluid within the primary chamber 2510 and the secondary chamber 2512 empties into the discharge chamber 2518. As fluid continues to flow into the discharge chamber 2518, a siphoning effect is created, which causes fluid in the primary chamber 2510 and the secondary chamber 2512 to continue to empty until the fluid level drops to the empty-level 2516 of the first wall 2514. With the first drain valve 2534 open, fluid empties from the discharge chamber 2518 out through the first drain valve 2534. In some examples, in order to have fluid in the primary chamber 2510 and the secondary chamber 2512 empty until the fluid level drops to the empty-level 2516 of the first wall 2514, the first drain valve 2534 must be open or the discharge chamber 2518 needs to be sufficiently large to hold such a volume of fluid. Additionally, fluid held by the primary chamber 2510 and the secondary chamber 2512, but which has a fluid level at or below the empty-level 2516 of the first wall 2514, can be emptied from the primary chamber 2510 and the secondary chamber 2512 via the second drain valve 2536. In this way, the second drain valve 2536 can drain fluid that does not empty through the discharge chamber 2518.

Figure 26:
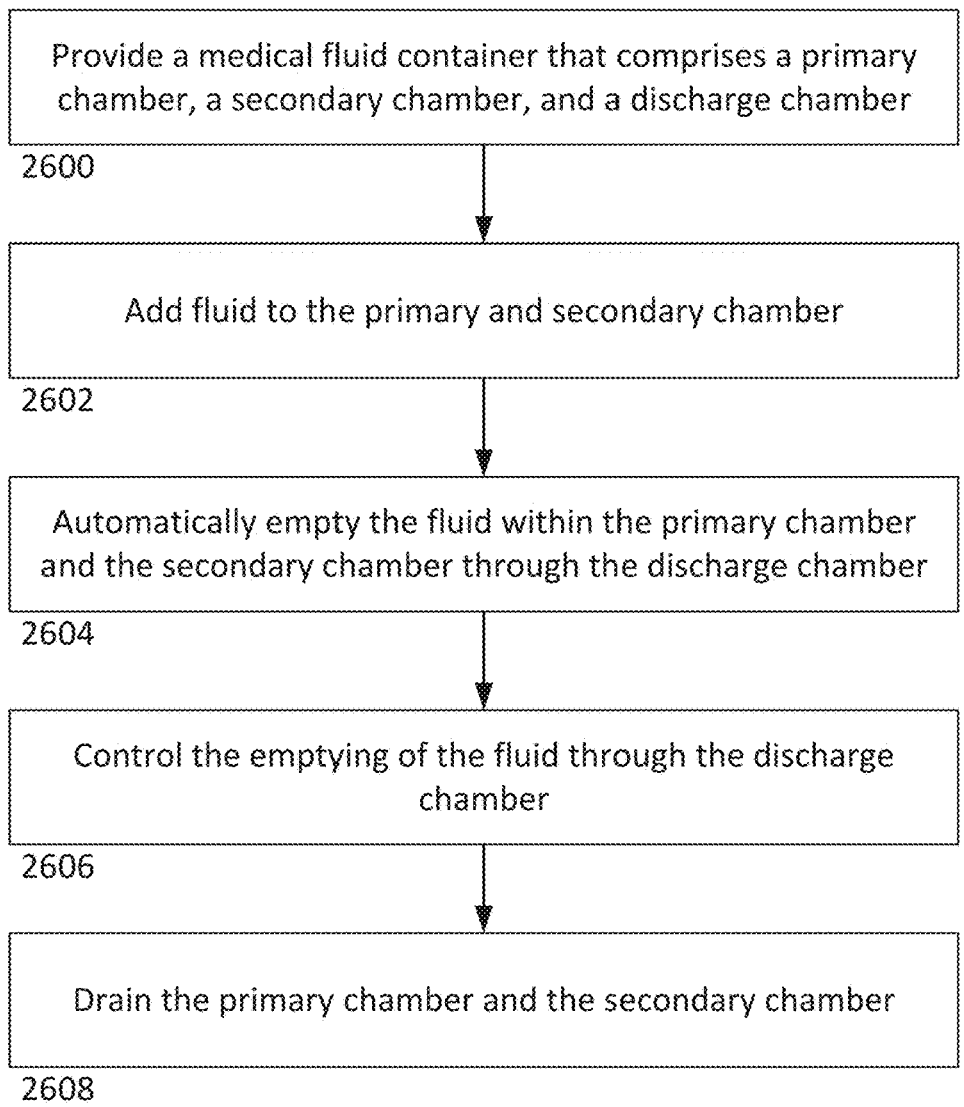
FIG. 26 is a flowchart of an example method involving the medical fluid container of FIG. 25 according to an aspect of the present disclosure.

Moving to FIG. 26, FIG. 26 is a flowchart of an example method involving the medical fluid container of FIG. 25 according to an aspect of the present disclosure. The method starts at step 2600 with providing a medical fluid container that comprises a primary chamber, a secondary chamber, and a discharge chamber. The secondary chamber is in fluid communication with the primary chamber and is partially separated from the primary chamber by a first wall that extends from a top of the medical fluid container to an empty-level near a bottom of the medical container. The discharge chamber is in fluid communication with the secondary chamber and is partially separated from the secondary chamber by a second wall that extends from the bottom of the medical fluid container to a full-level near the top of the medical fluid container.

The method continues with adding fluid (e.g., effluent) to the primary and secondary chambers in step 2602. In some examples, adding fluid to the primary and secondary chambers comprises adding fluid via a fill port which is located in one of the primary or secondary chambers. Fluid can fill both the primary and secondary chambers simultaneously as they are in fluid communication with each other.

Next, in step 2604, the method includes automatically emptying the fluid within the primary chamber and the secondary chamber through the discharge chamber. Automatically emptying the fluid occurs when fluid in the primary chamber and the secondary chamber rises above the full-level of the second wall. The automatically emptying the fluid can continue until the fluid in the primary chamber and the secondary chamber drops to the empty-level of the first wall.

In some embodiments, the method also includes the step 2606, which comprises controlling the emptying of the fluid through the discharge chamber. In some such embodiments, the medical fluid container can include a drain valve in fluid communication with the discharge chamber that is used to control the emptying of the fluid through the discharge chamber. The drain valve in fluid communication with the discharge chamber can be considered a first drain valve. In many instances, the drain valve can be in an open position during operation so that fluid automatically drains from the discharge chamber.

Additionally, in some embodiments, the method includes step 2608. Step 2608 comprises draining the primary chamber and the secondary chamber. To drain the primary chamber and the secondary chamber, the medical fluid container can include a drain valve in fluid communication with the primary chamber. The drain valve in fluid communication with the primary chamber can be considered a second drain valve. In some embodiments, the second drain valve can be used to drain the fluid from the primary chamber and the secondary chamber that does not empty through the discharge chamber. In many instances, this second drain valve can be in a closed position during operation so that fluid does not drain automatically from the primary chamber or the secondary chamber.

While the steps of FIG. 26 may be illustrated and discussed in a particular order, it will be appreciated that the steps of FIG. 26 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps. Moreover, while some steps are illustrated with dotted lines to indicate they are optional, in some examples, steps illustrated with solid lines can also be optional.

In the medical fluid container illustrated in FIG. 25 and the related method of FIG. 26, fluid is effectively siphoned from the primary chamber 2510 and the secondary chamber 2512 into the discharge chamber 2518 once it reaches the full level 2522 of the second wall 2520. The medical fluid container 2500 and its operation can be advantageous over other medical fluid containers for a variety of reasons. For instance, the medical fluid container can be used to receive effluent generated by an extracorporeal blood filtering machine and can automatically empty the effluent instead of a user replacing the medical fluid container with another, empty medical fluid container. Further, instead of simply draining the effluent, the medical fluid container can hold an amount of effluent before it automatically empties. This can be advantageous as the medical fluid container can be connected to a scale (e.g., effluent scale 246 of FIG. 2). In such examples, the scale can weigh the effluent in the medical fluid container while a controller (e.g., 249) can use the weight to adjust operation of the extracorporeal blood filtering machine as is described elsewhere herein. In contrast, if effluent is drained only via a drain, the weight of the effluent cannot be used to adjust the operation of an extracorporeal blood filtering machine.

Figure 27:
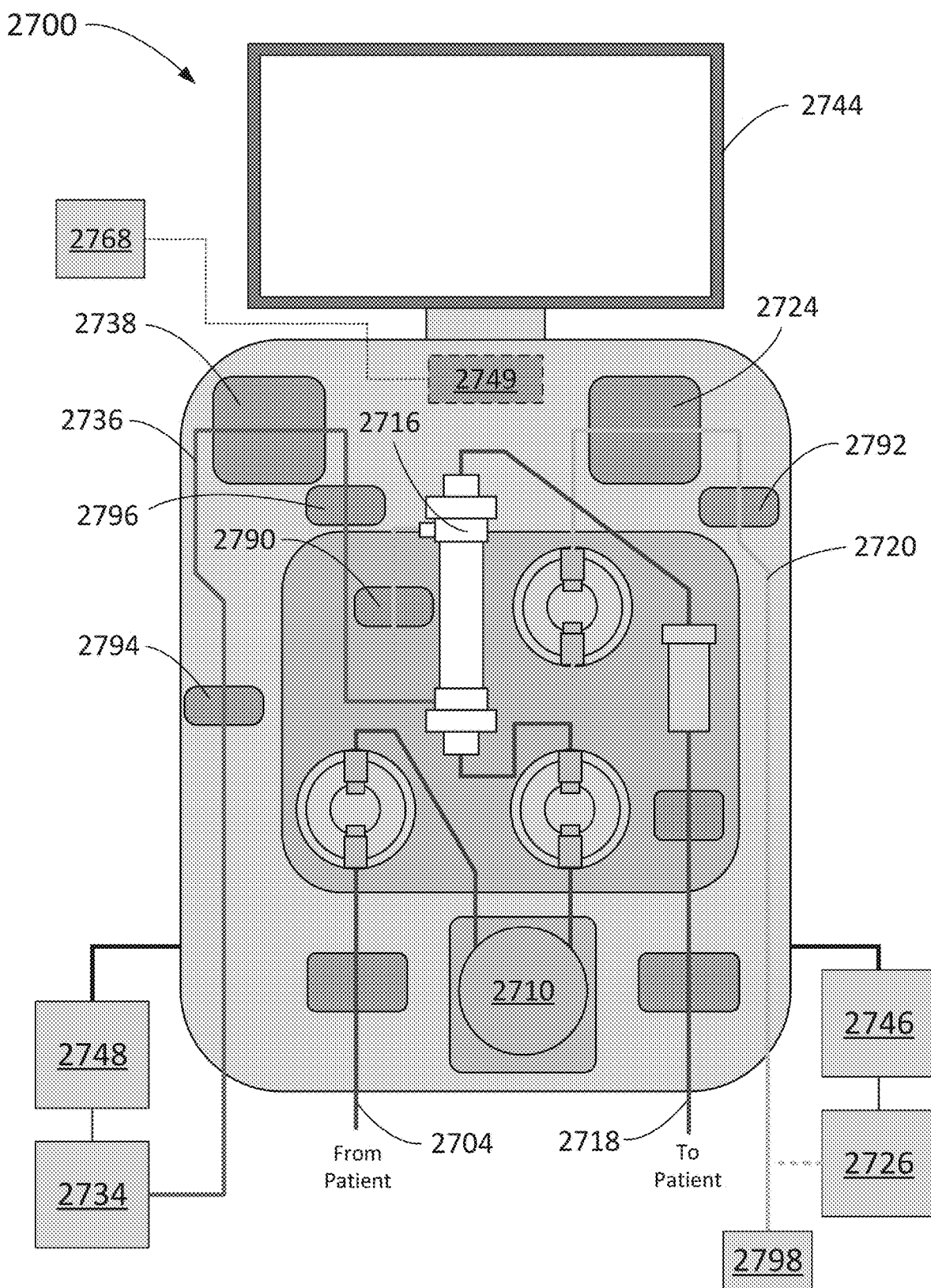
FIG. 27 is a schematic view of an example extracorporeal blood filtering machine according to an aspect of the present disclosure.

Moving to FIG. 27, FIG. 27 is a schematic view of an example extracorporcal blood filtering machine 2700 according to an aspect of the present disclosure. The extracorporeal blood filtering machine 2700 can include some or all of the features of the extracorporeal blood filtering machines described elsewhere herein (e.g., FIG. 2-6, 8, 10, 12). The extracorporcal blood filtering machine 2700 can also include features not previously described. For example, the extracorporeal blood filtering machine 2700 can include an effluent flow sensor 2746 (e.g., a weight scale), secondary effluent flow sensors 2790, 2792, a source fluid flow sensor 2748 (e.g., a weight scale), secondary source fluid flow sensors 2794, 2796, and a drain 2798. One of ordinary skill in the art will appreciate that the extracorporeal blood filtering machine 2700 of FIG. 27 is not limited to the illustrated components alone, as some components may be omitted for ease of illustration.

In the illustrated example of the extracorporeal blood filtering machine 2700 of FIG. 27, the extracorporeal blood filtering machine 2700 includes a blood circuit, an effluent circuit, and a source fluid circuit. As described elsewhere herein, the blood circuit can include a blood line having a blood inlet 2704 and a blood outlet 2718 along with a filter 2716 and a blood pump 2710. The effluent circuit can include an effluent line 2720 and an effluent pump 2724, which pumps effluent through the effluent line 2720 to an effluent receptacle 2726. In some examples, the effluent circuit can include one or more effluent flow sensors. The source fluid circuit can include a source fluid line 2736 and a source fluid pump 2738, which pumps source fluid from a source fluid reservoir 2734 through the source fluid line 2736. In some examples, the source fluid circuit can include one or more source fluid flow sensors. The extracorporeal blood filtering machine 2700 also includes a controller 2749 in communication with the blood pump 2710, the effluent pump 2724, and the source fluid pump 2738. The controller 2749 can also be in communication with other sensors of the extracorporeal blood filtering machine 2700 as discussed elsewhere herein. The controller 2749 can control various aspects of the extracorporeal blood filtering machine 2700, including the blood pump 2710, the effluent pump 2724, and the source fluid pump 2738. In some embodiments, the controller 2749 can control various aspects of the extracorporeal blood filtering machine 2700 in response to inputs (e.g., from user inputs, sensors, and the like). Additionally, the extracorporeal blood filtering machine 2700 includes a user input device 2768 and a display 2744 that are both in communication with the controller 2749. The user input device 2768 and/or the display 2744 can be configured to receive user input and provide the user input to the controller 2749. Additionally or alternatively, the display 2744 can receive output from the controller 2749 and display the output.

The extracorporeal blood filtering machine 2700 of FIG. 27 also includes the effluent flow sensor 2746, which is configured to measure an effluent flow quantity (e.g., weight, volume). In many examples, the effluent flow sensor 2746 comprises an effluent scale, which is configured to measure a dynamic effluent weight value of the effluent receptacle 2726. In some such examples, the dynamic effluent weight value of the effluent receptacle 2726 is used with an estimated or determined density value of the effluent to determine a volume of effluent in the effluent receptacle 2726.

In some embodiments, the extracorporeal blood filtering machine 2700 includes one or more secondary effluent flow sensors 2790, 2792 that are each configured to measure a secondary effluent flow quantity in the effluent line 2720 at a location different from the effluent flow sensor 2746. The secondary effluent flow sensors 2790, 2792 of FIG. 27 are in fluid communication with the effluent line 2720 and are configured to measure an effluent volume by measuring the fluid flow therethrough. While the secondary effluent flow sensor 2790 is illustrated as being before the effluent pump 2724, and the secondary effluent flow sensor 2792 is illustrated as being located after the effluent pump 2724, the secondary effluent flow sensor can be located anywhere along the effluent line 2720. Preferably, though, the secondary effluent flow sensor is located along the effluent line at a location different from the effluent flow sensor.

The extracorporeal blood filtering machine 2700 of FIG. 27 further includes the source fluid flow sensor 2748, which is configured to measure a source fluid flow quantity (e.g., weight, volume). In some examples, the source fluid flow sensor 2748 comprises a source fluid scale, which is configured to measure a dynamic source fluid weight value of the source fluid reservoir 2734. In some such examples, the dynamic source fluid weight value of the source fluid reservoir 2734 is used with an estimated or determined density value of the source fluid to determine a volume of source fluid in the source fluid reservoir 2734.

In some embodiments, the extracorporeal blood filtering machine 2700 includes one or more secondary source fluid flow sensors 2794, 2796 that are each configured to measure a secondary source fluid flow quantity in the source fluid line 2736 at a location different from the source fluid flow sensor 2748. The secondary source fluid flow sensors 2794, 2796 of FIG. 27 are in fluid communication with the source fluid line 2736 and are configured to measure a source fluid volume by measuring the fluid flow therethrough. While the secondary source fluid flow sensor 2794 is illustrated as being before the source fluid pump 2738, and the secondary source fluid flow sensor 2796 is illustrated as being located after the source fluid pump 2738, the secondary source fluid flow sensor can be located anywhere along the source fluid line 2736. Preferably, though, the secondary source fluid flow sensor is located along the source fluid line 2736 at a location different from the source fluid flow sensor.

Moving to example operations of the extracorporeal blood filtering machine 2700, the controller 2749 can be in communication with the blood pump 2710, the effluent pump 2724, and the effluent flow sensor 2746. The controller 2749 can then be configured to operate the extracorporeal blood filtering machine 2700 in an open-loop mode or a closed-loop mode. In the open-loop mode, the controller 2749 can set the blood pump speed and the effluent pump speed at respective fixed speeds. In the closed-loop mode, the controller 2749 can adjust the effluent pump speed based on the effluent flow quantity measured by the effluent flow sensor 2746. In some embodiments, the effluent receptacle 2726 comprises a drain (e.g., a sink or a toilet) when the controller 2749 is operating the extracorporeal blood filtering machine 2700 in the open-loop mode. Further, in some embodiments, the effluent receptacle 2726 comprises a bag (e.g., like the medical fluid receptacles described herein) when the controller 2749 is operating the extracorporeal blood filtering machine 2700 in the closed-loop mode.

In extracorporeal blood filtering machine embodiments that include a source fluid circuit, the controller 2749 can be in further communication with the source fluid pump 2738 and a source fluid flow sensor 2748. In such embodiments, when operating in the open-loop mode, the controller 2749 can set the source fluid pump speed at a fixed speed. Further, when operating in the closed-loop mode, the controller 2749 can adjust the source fluid pump speed based on the source fluid flow quantity measured by the source fluid flow sensor 2748.

As discussed elsewhere herein, the extracorporeal blood filtering machine 2700 can include one or more secondary source fluid flow sensors 2794, 2796 configured to measure a secondary source fluid flow quantity. In such embodiments, the controller 2749 can be in communication with the source fluid flow sensor 2748 and the secondary source fluid flow sensors 2794, 2796. The controller 2749 can then be configured to compare the secondary source fluid flow quantity with the source fluid flow quantity measured by the source fluid flow sensor 2748. If a difference between the secondary source fluid flow quantity and the source fluid flow quantity exceeds a threshold, the controller 2749 can output a source fluid flow mismatch alert. In some examples, the difference can be considered a "first difference" and the threshold can be considered a "first threshold." In some examples, the source fluid flow mismatch alert can be output to the user input device 2768 and/or the display 2744.

As discussed elsewhere herein, the extracorporeal blood filtering machine 2700 can include one or more secondary effluent flow sensors 2790, 2792 configured to measure a secondary effluent flow quantity. In such embodiments, the controller 2749 can be in communication with the effluent flow sensor 2746 and the secondary effluent flow sensors 2790, 2792. The controller 2749 can then be configured to compare the secondary effluent flow quantity with the effluent flow quantity measured by the effluent flow sensor 2746. If a difference between the secondary effluent flow quantity and the effluent flow quantity exceeds a threshold, the controller 2749 can output a flow mismatch alert. In some examples, the difference can be considered a "second difference" and the threshold can be considered a "second threshold." In some examples, the flow mismatch alert can be output to the user input device 2768 and/or the display 2744.

In some embodiments, the controller 2749 is configured to switch between operating in the open-loop mode and the closed-loop mode based on a user input (e.g., via user input device 2768 or display 2744). In some embodiments, the controller 2749 is configured to switch between operating in the open-loop mode and the closed-loop mode automatically. For instance, in some embodiments, the controller 2749 can receive a signal from a sensor (e.g., a movement sensor) to switch between operating in the open-loop mode and the closed-loop mode.

Figure 28:
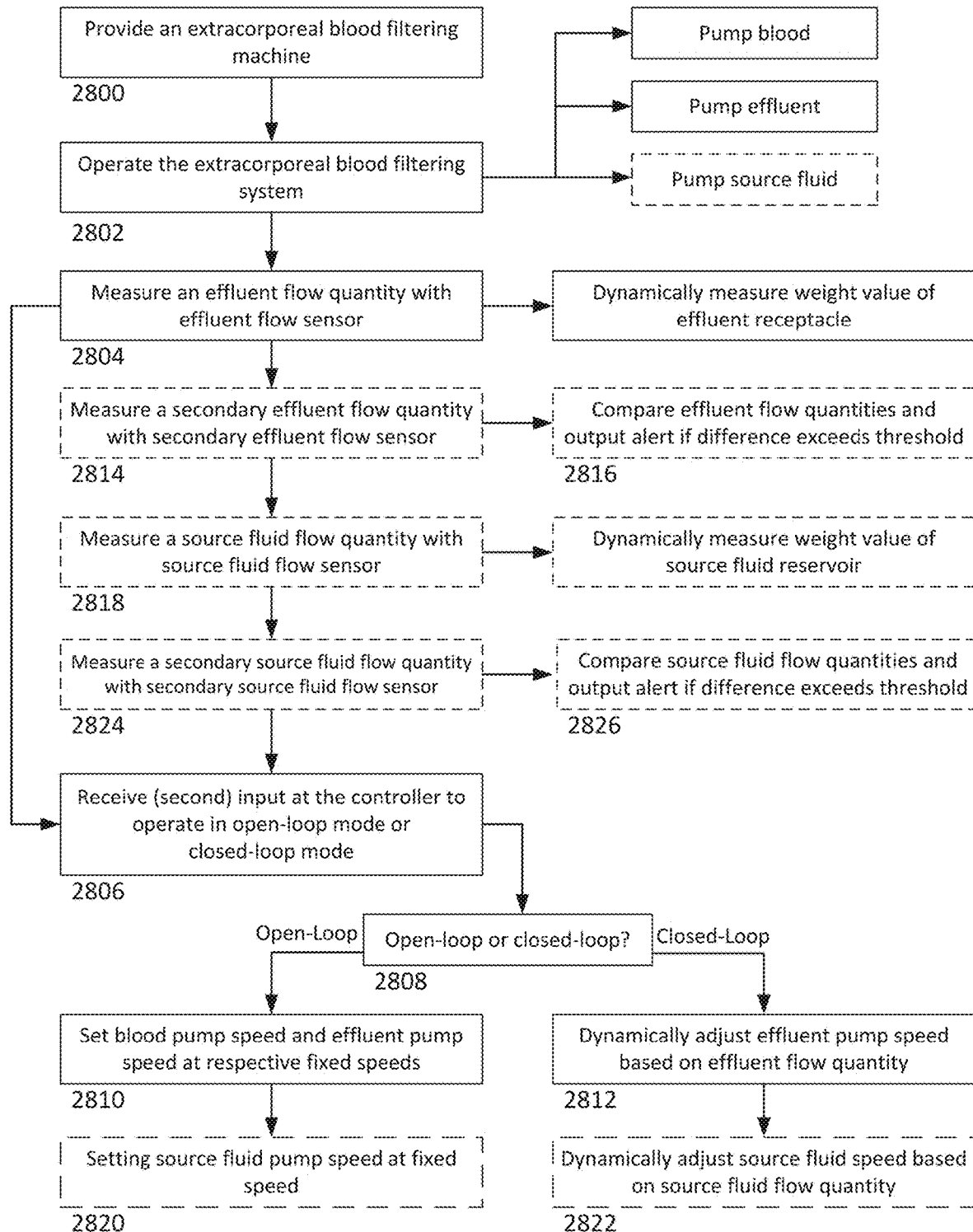
FIG. 28 is an example method of operating the extracorporeal blood filtering machine of FIG. 27 according to an aspect of the present disclosure.

Moving to FIG. 28, FIG. 28 is an example method of operating the extracorporeal blood filtering machine of FIG. 27 according to an aspect of the present disclosure. Starting at step 2800, the method includes providing an extracorporeal blood filtering machine. As described elsewhere herein, the extracorporeal blood filtering machine can include a blood circuit, an effluent circuit, an effluent flow sensor, and a controller.

Next, at step 2802, the method includes operating the extracorporcal blood filtering machine via the controller. Operating the extracorporeal blood filtering machine via the controller can include pumping blood with the blood pump at a blood pump speed from a patient, into the blood line through the blood inlet, through the filter, and back to the patient through the blood outlet. During operation, the filter can remove waste from the blood in the form of effluent and provide the effluent to the effluent line. Additionally, operating the extracorporeal blood filtering machine via the controller can include pumping the effluent with the effluent pump at an effluent pump speed from the filter, through the effluent line, into an effluent receptacle. In some examples, operating the extracorporeal blood filtering machine via the controller does not include operating the effluent pump.

The illustrated method continues with steps 2804 and 2806, which include measuring an effluent flow quantity with the effluent flow sensor (e.g., a dynamic effluent weight value from an effluent scale) and receiving an input at the controller to operate the extracorporcal blood filtering machine in an open-loop mode or in a closed-loop mode. In some embodiments, the controller receives an input from a user input device and/or a display.

Next the method includes the decision 2808. If the input received at the controller is to operate the extracorporeal blood filtering machine in the open-loop mode, the method includes setting the blood pump speed and the effluent pump speed by the controller at respective fixed speeds at step 2810. However, if the input received at the controller is to operate the extracorporeal blood filtering machine in the closed-loop mode, the method includes dynamically adjusting the effluent pump speed by the controller based on the effluent flow quantity at 2812.

In some examples, the effluent flow sensor comprises an effluent scale, and the method step 2804 includes dynamically measuring a weight value of the effluent receptacle. In some embodiments, the effluent receptacle comprises a drain when the controller is operating the extracorporeal blood filtering machine in the open-loop mode. In some embodiments, the effluent receptacle comprises a bag when the controller is operating the extracorporcal blood filtering machine in the closed-loop mode.

In some optional embodiments, the extracorporeal blood filtering machine includes a secondary effluent flow sensor on the effluent line. In such embodiments, the method can further include steps 2814 and 2816. Step 2814 includes taking a secondary effluent flow quantity measurement with the secondary effluent flow sensor. Step 2816 includes comparing the secondary effluent flow quantity measurement with the effluent flow quantity and outputting an effluent flow mismatch alert if a difference between the secondary effluent flow quantity measurement and the effluent flow quantity exceeds a threshold. While steps 2814 and 2816 are illustrated as occurring before the open-loop or closed-loop determination of step 2808, they can occur at any time. For example, steps 2814 and 2816 can occur during an open-loop mode operation.

Additionally, in some optional embodiments, the extracorporeal blood filtering machine includes a source fluid circuit and a source fluid flow sensor. In such embodiments, the operating the extracorporeal blood filtering machine of step 2802 further includes pumping source fluid with the source fluid pump at a source fluid pump speed from the source fluid reservoir, through the source fluid line, into the blood circuit. The method can also include step 2818. Step 2818 includes measuring a source fluid flow quantity with the source fluid flow sensor. Referring back to the decision step 2808, if the input received at the controller is to operate the extracorporeal blood filtering machine in the open-loop mode, the method can include setting the source fluid pump speed by the controller at a respective fixed speed as in step 2820. However, if the input received at the controller is to operate the extracorporeal blood filtering machine in the closed-loop mode, the method can include dynamically adjusting the source fluid pump speed by the controller based on the source fluid flow quantity as in step 2822. In both the open-loop mode and the closed-loop mode, the method can return to operating the extracorporeal blood filtering machine as in step 2802.

In some examples, the source fluid flow sensor comprises a source fluid scale and the method step 2812 includes dynamically measuring a weight value of the source fluid reservoir.

In some optional embodiments, the extracorporeal blood filtering machine includes a secondary source fluid flow sensor on the source fluid line. In such embodiments, the method can further include steps 2824 and 2826. Step 2824 includes taking a secondary source fluid flow quantity measurement with the secondary source fluid flow sensor. Step 2826 includes comparing the secondary source fluid flow quantity measurement with the source fluid flow quantity and outputting a source fluid flow mismatch alert if a difference between the secondary source fluid flow quantity measurement and the source fluid flow quantity exceeds a threshold. While steps 2824 and 2826 are illustrated as occurring before the open-loop or closed-loop determination of step 2808, they can occur at any time. For example, steps 2824 and 2826 can occur during an open-loop mode operation. Again, in both the open-loop mode and the closed-loop mode, the method can return to operating the extracorporeal blood filtering machine as in step 2802.

The method can optionally return to step 2806 after operating in the open-loop mode or the closed-loop mode. In step 2806 the method can comprise receiving a second input at the controller to switch operations. For instance, if the extracorporeal blood filtering machine is operating in the open-loop mode and receives a second input to operate in the closed-loop mode, the method continues with step 2812. In such an example, the extracorporeal blood filtering machine can switch from holding the effluent pump speed at the fixed speed, to dynamically adjusting the effluent pump speed by the controller based on the effluent flow quantity. Alternatively, if the extracorporeal blood filtering machine is operating in the closed-loop mode and receives a second input to operate in the open-loop mode, the method continues with step 2810. In such an example, the extracorporeal blood filtering machine can switch from dynamically adjusting the effluent pump speed by the controller based on the effluent flow quantity to holding the effluent pump speed at a fixed speed. The source fluid pump speed can similarly be switched to/from a fixed speed from/to dynamically adjusting its speed based on source fluid flow quantity.

While the steps of FIG. 28 may be illustrated and discussed in a particular order, it will be appreciated that the steps of FIG. 28 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps. Moreover, while some steps are illustrated with dotted lines to indicate they are optional, in some examples, steps illustrated with solid lines can also be optional (e.g., pumping effluent).

One advantage of the extracorporeal blood filtering machine being able to operate in an open-loop mode and/or a closed-loop mode is increased flexibility of the extracorporeal blood filtering machine. For example, as is explained further with respect of FIG. 29, FIG. 30, and FIG. 31, being able to operate in an open-loop mode can enable the extracorporeal blood filtering machine to be transported more easily. Another advantage of the illustrated and described extracorporeal blood filtering machine is increased accuracy in both the open-loop mode and closed-loop mode which is achieved in part by using the flow sensors. Additionally, even if the extracorporeal blood filtering machine starts to become inaccurate, a user can be easily alerted to the inaccuracy issue. In some embodiments, the extracorporeal blood filtering machine can be operated in open-loop mode with respect to the source fluid circuit and source fluid pump and in a closed-loop mode with respect to the effluent circuit and effluent pump, or vice versa.

Figure 29:
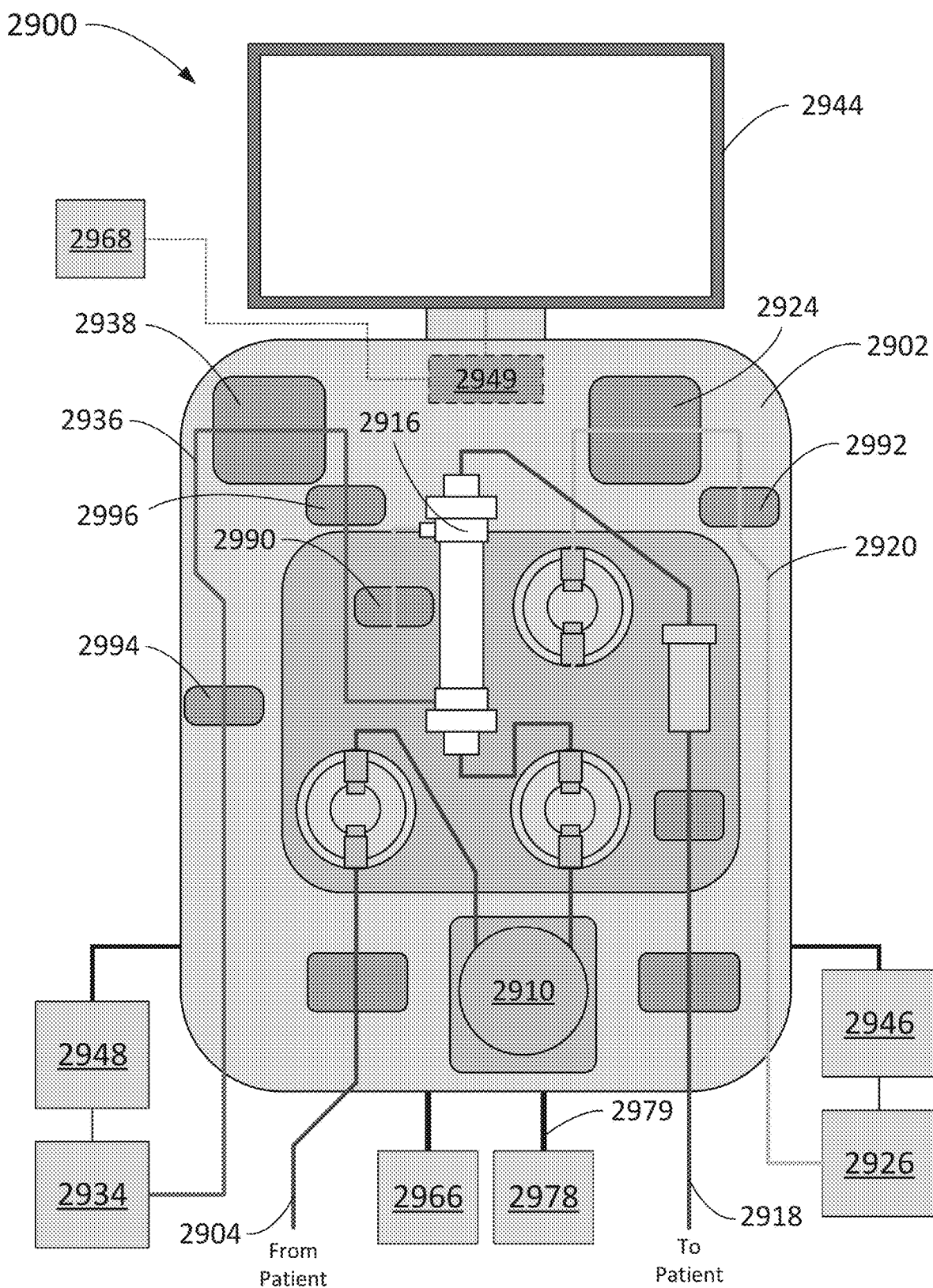
FIG. 29 is a schematic view of an example extracorporeal blood filtering system including an example extracorporeal blood filtering machine according to an aspect of the present disclosure.

Moving to FIG. 29, FIG. 29 is a schematic view of an example extracorporeal blood filtering system 2900 including an example extracorporeal blood filtering machine 2902 according to an aspect of the present disclosure. The extracorporeal blood filtering system 2900 can include some or all of the features related to an extracorporeal blood filtering machine and/or system described elsewhere herein (e.g., FIGS. 2-6, 8, 10, 12, 27). For example, the extracorporeal blood filtering system 2900 can include the various source line connection positions described in connection with FIGS. 3-6. The extracorporeal blood filtering system 2900 can also include features not previously described. For example, extracorporeal blood filtering system 2900 can include a battery 2966 and an external power source 2978. One of ordinary skill in the art will appreciate that the extracorporeal blood filtering system 2900 of FIG. 29 is not limited to the illustrated components alone as some components may be omitted for ease of illustration.

In the illustrated example of the extracorporeal blood filtering system 2900 of FIG. 29, the extracorporeal blood filtering system 2900 includes all the features of the extracorporeal blood filtering machine of FIG. 27 including the blood circuit, the effluent circuit, and the source fluid circuit. The extracorporeal blood filtering system 2900 further includes the battery 2966 and the external power source 2978. The battery 2966 is configured to provide power to the extracorporeal blood filtering machine 2902 for the extracorporeal blood filtering machine 2902 to operate. In some examples, the battery 2966 can have a large enough capacity to power the extracorporeal blood filtering machine 2902 for an extended period (e.g., 20 minutes or more). The battery 2966 can comprise any type of battery and can be configured to provide primary power and/or backup power to the extracorporeal blood filtering machine 2902. The battery 2966 can be electrically connected to some or all the components of the extracorporeal blood filtering machine 2902 to power said components. For example, the battery 2966 can be connected to the blood pump 2910, the source fluid pump 2938, the effluent pump 2924, the controller 2949, the display 2944, and other components of the extracorporeal blood filtering machine 2902 including sensors and scales. The battery 2966 can be integrated into the extracorporeal blood filtering machine 2902 or can be provided as part of the extracorporeal blood filtering system 2900 such as being on a cart containing the extracorporeal blood filtering machine 2902 (e.g., as illustrated in FIG. 1). In some examples, the extracorporeal blood filtering system 2900 includes multiple batteries.

Similarly, the external power source 2978 is configured to provide power to the extracorporeal blood filtering machine 2902 for the extracorporeal blood filtering machine 2902 to operate. The external power source 2978 can be connected to the extracorporeal blood filtering machine 2902 by a power connector 2979, such as a standard power plug. The external power source 2978 can be configured to provide primary power and/or backup power to the extracorporeal blood filtering machine 2902. In some examples, the battery 2966 provides backup power while the external power source 2978 provides primary power to the extracorporeal blood filtering machine 2902. The external power source 2978 can be electrically connected to some or all the components of the extracorporeal blood filtering machine 2902 to power said components. For example, the extracorporeal blood filtering machine 2902 can be connected to the blood pump 2910, the source fluid pump 2938, the effluent pump 2924, the controller 2949, the display 2944, and other components of the extracorporeal blood filtering machine 2902 including sensors and scales. In some examples, the extracorporeal blood filtering system 2900 includes multiple external power sources such as a primary external power source and a secondary, backup external power source.

Now referencing the controller 2949, the controller 2949 can be in communication with some or all components within the extracorporeal blood filtering system 2900 and can operate the extracorporeal blood filtering system 2900, including some or all aspects of the extracorporeal blood filtering machine 2902. For example, the controller 2949 is in communication with the extracorporeal blood filtering machine 2902 and is configured to operate the extracorporeal blood filtering machine 2902 in a stationary mode of operation and in a transport mode of operation. In both the stationary mode of operation and in the transport mode of operation, the blood pump 2910 is active and can pump blood.

However, the effluent pump 2924 can be in an effluent pump stationary state when the extracorporeal blood filtering machine is in the stationary mode of operation and in an effluent pump transport state when the extracorporeal blood filtering machine is in the transport mode of operation. The effluent pump 2924 can be active (e.g., pumping effluent) in the effluent pump stationary state and inactive (e.g., not pumping effluent) in the effluent pump transport state. Additionally or alternatively, in some examples, the effluent pump is closed-loop controlled in the effluent pump stationary state and is open-loop controlled in the effluent pump transport state. Closed-loop control and open-loop control are further described in connection with FIGS. 27-28.

In some examples, the controller 2949 can switch the extracorporeal blood filtering machine 2902 from the transport mode of operation to the stationary mode of operation. In some such examples, the controller 2949 can be configured to compare an estimated quantity of effluent that was collected in the effluent receptacle while the extracorporeal blood filtering machine was in the transport mode of operation with an actual quantity of effluent that was collected in the effluent receptacle while the extracorporeal blood filtering machine was in the transport mode of operation. The controller 2949 can further be configured to adjust the effluent pump 2924 to account for an effluent discrepancy between the estimated quantity of effluent and the actual quantity of effluent. For example, the controller 2949 could increase or decrease the effluent pump speed for a period of time to account for the discrepancy.

In some embodiments, to obtain the estimated quantity of effluent that was collected in the effluent receptacle in the transport mode of operation, the controller 2949 can use measurements from the effluent flow sensors 2990, 2992. In many embodiments, to obtain the actual quantity of effluent that was collected in the effluent receptacle in the transport mode of operation, the controller 2949 can use measurements from the effluent scale 2946. For example, an effluent weight value measured by the effluent scale 2946 just before the extracorporeal blood filtering machine 2902 is switched into the transport mode of operation can be compared with an effluent weight value measured by the effluent scale 2946 just after the extracorporeal blood filtering machine 2902 is switched back to the stationary mode of operation. Additionally, in some examples, the controller 2949 can receive measurements from one or more effluent density sensors (e.g., 1282, 1284 of FIG. 12) to obtain one or both of the estimated quantity of effluent or the actual quantity of effluent.

As illustrated in FIG. 29, the extracorporeal blood filtering system includes a user interface device 2968 and the display 2944 that are in communication with the controller 2949. Both the user interface device 2968 and the display 2944 can be used as user interfaces and can receive one or more parameters from a user. Further, the user interface device 2968 and the display 2944 can receive outputs from the controller 2949 and can, in some examples, display the output.

In some embodiments, the controller 2949 can be configured to receive an effluent open-loop limit parameter from a user through the user interface. Additionally, the controller 2949 can be configured to output an effluent error notification via the user interface when the effluent open-loop limit parameter has been exceeded in the transport mode of operation. An effluent open-loop limit parameter can comprise one or more parameters including but not limited to time of operation in the transport mode, a quantity of effluent, source fluid, and/or blood pumped in the transport mode, and a flow mismatch between effluent and/or source fluid flow sensors. In some examples, the controller 2949 is further configured to switch the effluent pump transport state to inactive when the effluent open-loop limit parameter has been exceeded in the transport mode of operation. This can be advantageous as the quantity of effluent pumped may no longer be accurate once the effluent open-loop limit parameter has been exceeded. An inaccurate quantity of effluent pumped can lead to fluid imbalance and other compromised treatment of a patient. Instead, by switching the effluent pump transport state to inactive, the amount of effluent pumped can be approximately known within a degree of error.

In some embodiments, the controller 2949 can be configured to receive a transport mode command from a user through the user interface. Additionally, the controller 2949 can be configured to switch from the stationary mode of operation to the transport mode of operation in response to the transport mode command.

Continuing with the controller 2949 of FIG. 29, the controller 2949 can be configured to operate the extracorporeal blood filtering machine 2902 in the stationary mode of operation when the extracorporeal blood filtering machine 2902 is receiving power from an external power source 2978 via a power connector 2979. Additionally, the controller 2949 can be configured to operate the extracorporeal blood filtering machine 2902 in the transport mode of operation when the extracorporeal blood filtering machine 2902 is receiving power from a battery 2966. In some embodiments, the controller 2949 is in communication with a user interface (e.g., user interface device 2968, display 2944) and is configured to detect when the controller is receiving power from the battery 2966. In such embodiments, the controller 2949 can output a prompt to a user via the user interface to switch the extracorporeal blood filtering machine 2902 to the transport mode of operation.

In some embodiments, the controller 2949 can be configured to detect that the extracorporeal blood filtering machine has begun to be transported (e.g., via a movement sensor such as an accelerometer). In some such embodiments, the controller 2949 can automatically switch the extracorporeal blood filtering machine 2902 into the transport mode of operation. Alternatively, in some such embodiments, the controller 2949 can output a prompt to a user via the user interface to switch the extracorporeal blood filtering machine 2902 to the transport mode of operation.

The controller 2949 can also be configured to resume operating the extracorporeal blood filtering machine 2902 in the stationary mode of operation after operating the extracorporeal blood filtering machine 2902 in the transport mode of operation. For example, the controller 2949 can resume operating in the stationary mode of operation when the extracorporeal blood filtering machine 2902 receives power from the external power source 2978 after receiving power from the battery 2966.

Embodiments of the extracorporeal blood filtering system 2900 can include a source fluid circuit with a source fluid pump 2938. Further, as described elsewhere herein, the controller 2949 is in communication with the extracorporeal blood filtering machine 2902 and is configured to operate the extracorporeal blood filtering machine 2902 in a stationary mode of operation and in a transport mode of operation. Thus, in similarity with the effluent pump 2924 operation, the source fluid pump 2938 can be in a source fluid pump stationary state in the stationary mode of operation and in a source fluid pump transport state in the transport mode of operation. The source fluid pump 2938 can be active (e.g., pumping source fluid) in the source fluid pump stationary state and can be inactive (e.g., not pumping source fluid) in the source fluid pump transport state. Additionally or alternatively, in some examples, the source fluid pump 2938 can be closed-loop controlled in the source fluid pump stationary state and can be open-loop controlled in the source fluid pump transport state. In some embodiments, the source fluid pump 2938 can be inactive in the source fluid pump transport state, and the effluent pump 2924 can be open-loop controlled in the effluent pump transport state. In some embodiments, the source fluid pump 2938 can be open-loop controlled in the source fluid pump transport state, and the effluent pump can be inactive in the effluent pump transport state. Closed-loop control and open-loop control are further described with respect to FIG. 27 and FIG. 28.

In some examples, the controller 2949 can switch the extracorporeal blood filtering machine 2902 from the transport mode of operation to the stationary mode of operation. In some such examples, the controller 2949 can be configured to compare an estimated quantity of source fluid that was pumped from the source fluid reservoir into the blood circuit while the extracorporeal blood filtering machine was in the transport mode of operation with an actual quantity of source fluid that was pumped from the source fluid reservoir into the blood circuit while the extracorporeal blood filtering machine was in the transport mode of operation. For example, a source fluid weight value measured by the source fluid scale 2948 just before the extracorporeal blood filtering machine 2902 is switched into the transport mode of operation can be compared with a source fluid weight value measured by the source fluid scale 2948 just after the extracorporeal blood filtering machine 2902 is switched back to the stationary mode of operation. The controller 2949 can further be configured to adjust the source fluid pump 2938 to account for a source fluid discrepancy between the estimated quantity of source fluid and the actual quantity of source fluid. For example, the controller 2949 could increase or decrease the source fluid pump speed for a period of time to account for the discrepancy.

Again, as described elsewhere herein, the controller 2949 can be in communication with a user interface. The controller 2949 can then be configured to receive a source fluid open-loop limit parameter from a user through the user interface. Additionally, the controller 2949 can be configured to output a source fluid error notification via the user interface when the source fluid open-loop limit parameter has been exceeded in the transport mode of operation. A source fluid open-loop limit parameter can comprise one or more parameters including but not limited to time of operation in the transport mode, a quantity of effluent, source fluid, and/or blood pumped in the transport mode, and a flow mismatch between effluent and/or source fluid flow sensors. In some examples, the controller 2949 is further configured to switch the source fluid pump transport state to inactive when the source fluid open-loop limit parameter has been exceeded in the transport mode of operation. This can be advantageous as the quantity of source fluid pumped may no longer be accurate once the source fluid open-loop limit parameter has been exceeded. An inaccurate quantity of source fluid pumped can lead to fluid imbalance and other compromised treatment of a patient. Instead, by switching the source fluid pump transport state to inactive, the amount of source fluid pumped can be approximately known within a degree of error.

Figure 30:
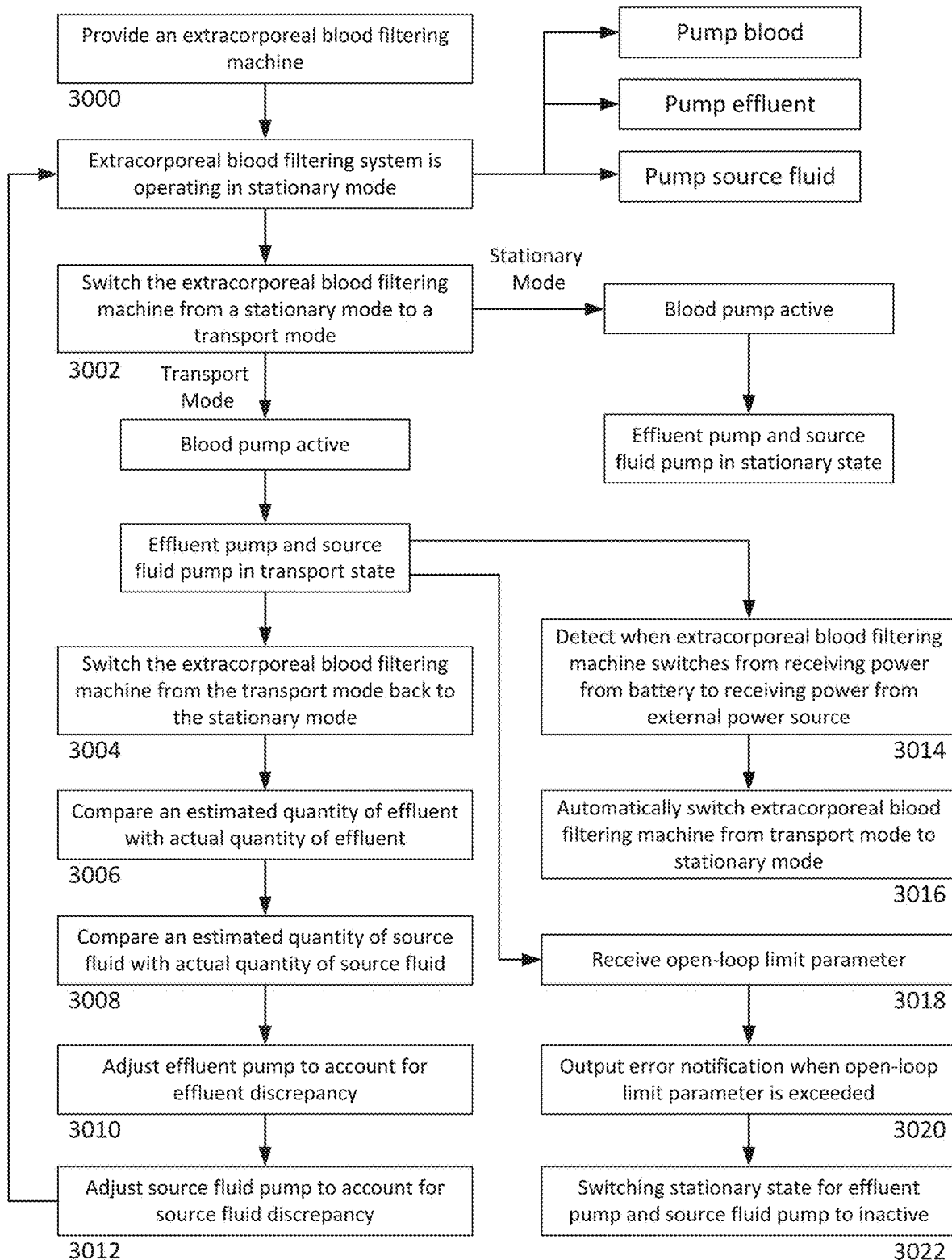
FIG. 30 is a flowchart of an example method of operating the extracorporeal blood filtering machine of FIG. 29 according to an aspect of the present disclosure.

Moving to FIG. 30, FIG. 30 is a flowchart of an example method of operating the extracorporeal blood filtering machine of FIG. 29 according to an aspect of the present disclosure. The method starts at step 3000 with providing an extracorporeal blood filtering machine. As described elsewhere herein, the extracorporeal blood filtering machine can include a blood circuit, an effluent circuit, and a source fluid circuit, along with their associated components. Next, while not an affirmative method step, the extracorporeal blood filtering machine can be operating in a stationary mode of operation. The stationary mode of operation can simply include operating the extracorporeal blood filtering machine. Operating the extracorporeal blood filtering machine generally includes pumping blood through the filter, pumping effluent generated by the filter into an effluent receptacle, and pumping source fluid into a blood line, as is described elsewhere herein.

The method continues at step 3002 with switching the extracorporcal blood filtering machine from a stationary mode of operation to a transport mode of operation. As illustrated, in the stationary mode of operation, the blood pump is active while the effluent pump and the source fluid pump are each in a stationary state. In some examples, the effluent pump and the source fluid pump are each active in the stationary state. In some examples, the effluent pump and the source fluid pump are each closed-loop controlled in the stationary state. Alternatively, in the transport mode of operation, the blood pump is again active while the effluent pump and the source fluid pump are each in a transport state. In some examples, the effluent pump and the source fluid pump are each inactive in the transport state. In some examples, the effluent pump and the source fluid pump are each open-loop controlled in the transport state. In some examples, one of the effluent pump and the source fluid pump is inactive in the transport state and the other of the effluent pump and the source fluid pump is open-loop controlled in the transport state. The method can then continue with step 3004, 3018, and/or 3014.

Starting with step 3004, the method can include switching the extracorporeal blood filtering machine from the transport mode of operation back to the stationary mode of operation. The method can further include comparing an estimated quantity of effluent that was collected in the effluent receptacle while the extracorporeal blood filtering machine was in the transport mode of operation with an actual quantity of effluent that was collected in the effluent receptacle while the extracorporeal blood filtering machine was in the transport mode of operation, as in step 3006. Additionally, the method can include comparing an estimated quantity of source fluid that was pumped from the source fluid reservoir into the blood circuit while the extracorporeal blood filtering machine was in the transport mode of operation with an actual quantity of source fluid that was pumped from the source fluid reservoir into the blood circuit while the extracorporeal blood filtering machine was in the transport mode of operation, as in step 3008.

Next, in steps 3010 and 3012, the method can include adjusting the effluent pump and/or the source fluid pump. In step 3010, the method includes adjusting the effluent pump to account for an effluent discrepancy between the estimated quantity of effluent and the actual quantity of effluent. In step 3012, the method includes adjusting the source fluid pump to account for a source fluid discrepancy between the estimated quantity of source fluid and the actual quantity of source fluid. In some embodiments, the method can return to the extracorporeal blood filtering machine being operated in the stationary mode.

Moving to step 3014, the method can include detecting when the extracorporeal blood filtering machine switches from receiving power from a battery to receiving power from an external power source via a power connector. If the switching of receiving power is detected, the method can further include automatically switching the extracorporeal blood filtering machine from the transport mode of operation to the stationary mode of operation as in step 3016. In some examples, the method can continue from step 3016 to step 3006 due to the transition from operating in the transport mode to operating in the stationary mode.

Moving to step 3018, the method can include receiving an open-loop limit parameter from a user (e.g., via a user interface). Next, in step 3020, the method can include outputting an error notification when the open-loop limit parameter has been exceeded in the transport mode of operation. Further, if the open-loop limit parameter has been exceeded in the transport mode of operation, the method can include switching the stationary state for each of the effluent pump and the source fluid pump to inactive as in step 3022.

Figure 31:
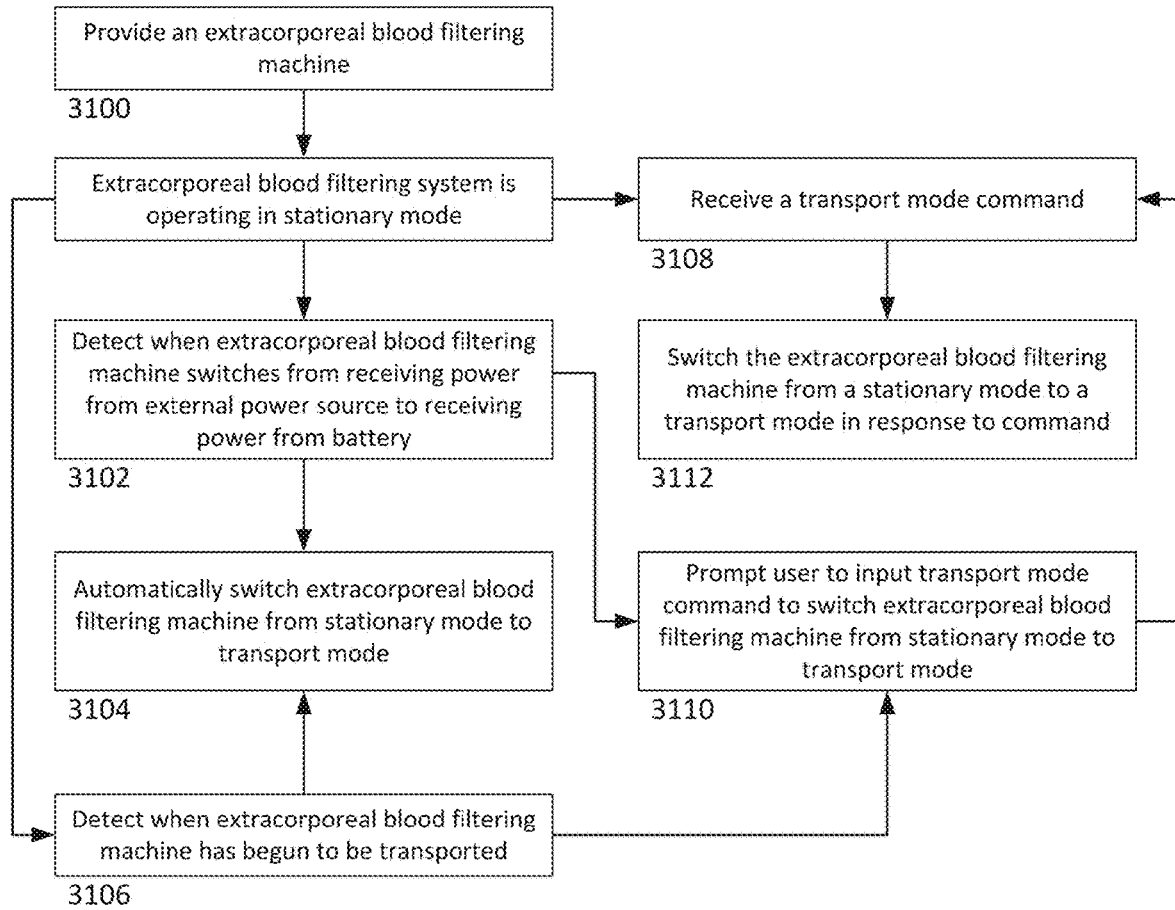
FIG. 31 is a flow chart of another example method of operating the example extracorporeal blood filtering machine of FIG. 29 according to an aspect of the present disclosure.

Moving to FIG. 31, FIG. 31 is a flow chart of an example method of operating the example extracorporeal blood filtering machine of FIG. 29 according to an aspect of the present disclosure. Starting with step 3100, the method can include providing an extracorporeal blood filtering machine (e.g., like those described elsewhere herein). Next, while not an affirmative step, the extracorporeal blood filtering machine can be operating in a stationary mode of operation. The stationary mode of operation can simply include operating the extracorporeal blood filtering machine. Operating the extracorporeal blood filtering machine generally includes pumping blood through the filter, pumping effluent generated by the filter into an effluent receptacle, and pumping source fluid into a blood line, as is described elsewhere herein. The method can then continue with step 3102, 3106, or 3108.

Starting with step 3102, the method can include detecting when the extracorporeal blood filtering machine switches from receiving power from an external power source via a power connector to receiving power from a battery. If the switching of receiving power is detected, the method can continue with step 3104 or 3110. Step 3104 includes automatically switching the extracorporeal blood filtering machine from the stationary mode of operation to the transport mode of operation. Alternatively, step 3110 includes prompting a user to input a transport mode command to switch the extracorporeal blood filtering machine from the stationary mode of operation to the transport mode of operation. From step 3110, the method can continue with step 3108.

Moving to step 3108, the method can include receiving a transport mode command from a user (e.g., via a user interface). Once received, the method continues with step 3112 which includes switching the extracorporeal blood filtering machine from a stationary mode of operation to a transport mode of operation in response to the transport mode command.

Moving to step 3106, the method can include detecting when the extracorporcal blood filtering machine has begun to be transported (e.g., via a movement sensor). From step 3106, the method can continue with either step 3104 or step 3110

As illustrated in the example method of operation illustrated in FIG. 31, the extracorporeal blood filtering machine can change from operating in the stationary mode to operating in the transport mode manually from receiving a transport mode command, or automatically, as in step 3104. In the manual method, the extracorporeal blood filtering machine can directly receive a transport command or receive a transport command after prompting a user. Further, to prompt the user, the extracorporeal blood filtering machine can detect a change in power source, as in step 3102, or a transportation indication (e.g., being moved) as in step 3016. Alternatively, the extracorporeal blood filtering machine can detect the change in the power source, as in step 3102, or the transportation indication, as in step 3016, to automatically switch operating modes.

While the steps of FIG. 30 and FIG. 31 may be illustrated and discussed in a particular order, it will be appreciated that the steps of FIG. 30 and FIG. 31 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps.

There are several advantages of the extracorporeal blood filtering machine of FIG. 29 and the associated methods of FIG. 30 and FIG. 31. For example, when a patient receiving extracorporeal blood filtering via the extracorporeal blood filtering machine moves from one place to another (e.g., to use the restroom), the effluent receptacle and/or the source fluid receptacle can move around during transport. The moving around can impact the weight values measured by the respective scales, and using those weight values in closed-loop control of the effluent pump and/or the source fluid pump can lead to fluid imbalance. This imbalance can be especially pronounced for very small patients who have a small overall quantity of bodily fluids relative to larger patients. Switching the extracorporeal blood filtering machine into transport mode, and out of closed-loop control of the respective pumps, can aid in patient fluid balance.

Figure 32:
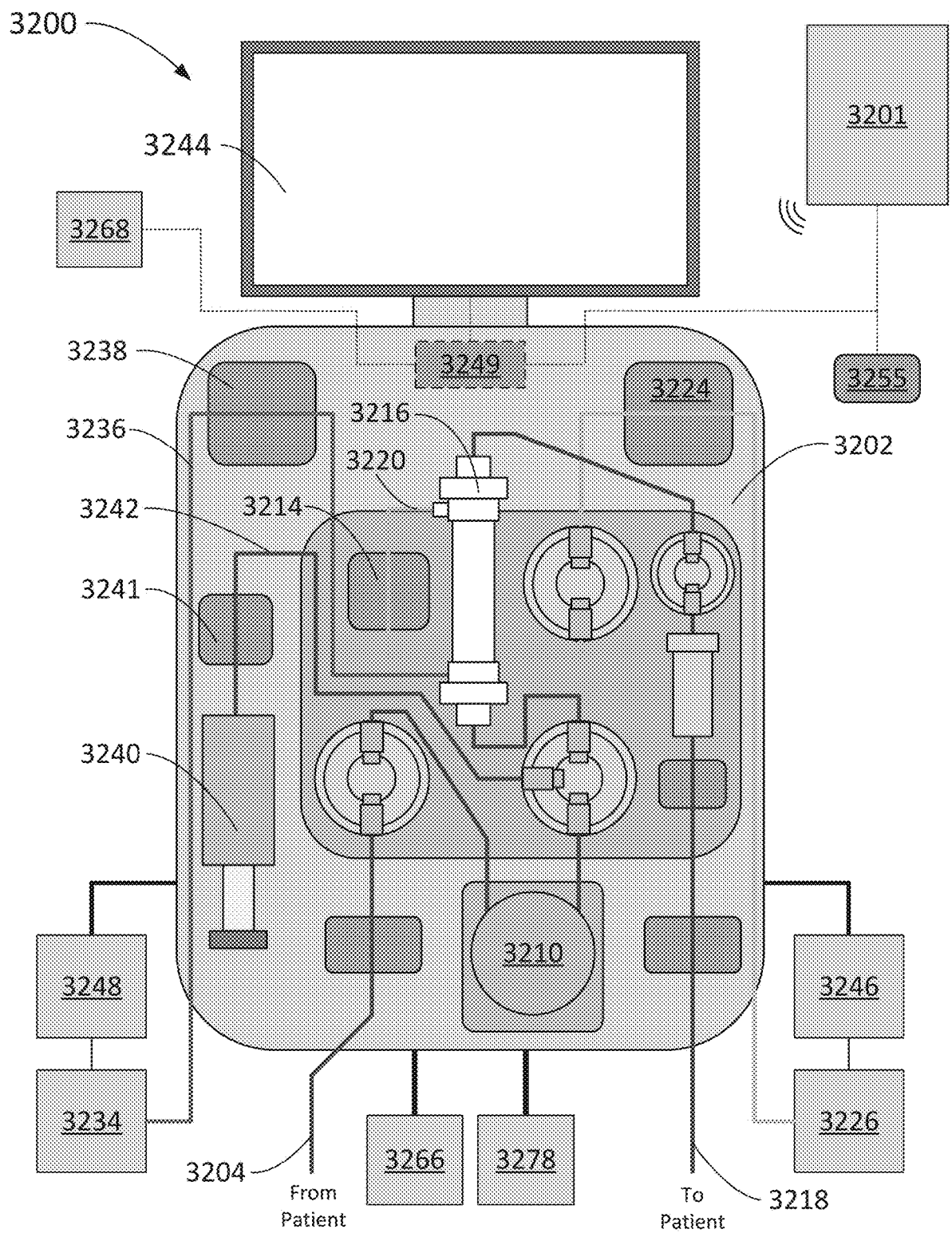
FIG. 32 is a schematic view of an example extracorporeal blood filtering system including an example extracorporeal blood filtering machine according to an aspect of the present discourse.

Moving to FIG. 32, FIG. 32 is a schematic view of an example extracorporeal blood filtering system 3200 including an example extracorporeal blood filtering machine 3202 according to an aspect of the present disclosure. The extracorporeal blood filtering system 3200 can include some or all of the features related to an extracorporeal blood filtering machine and/or system described elsewhere herein (e.g., FIGS. 2-6, 8, 10, 12, 27, 29). The extracorporeal blood filtering system 3200 can also include features not previously described. For example, extracorporeal blood filtering system 3200 can include an anticoagulant pump 3241 and can interact with an external device 3201. One of ordinary skill in the art will appreciate that the extracorporeal blood filtering system 3200 of FIG. 32 is not limited to the illustrated components alone as some components may be omitted for ease of illustration.

In the illustrated example of the extracorporeal blood filtering system 3200 of FIG. 32, the extracorporeal blood filtering system 3200 includes all the features of the extracorporeal blood filtering machine of FIG. 2 including the blood circuit, the effluent circuit, and the source fluid circuit. As described elsewhere herein, source fluid pumped by the source fluid circuit into the blood line can include one or more of dialysate replacement fluid, electrolyte fluid, or general nutritional injection fluid. The extracorporeal blood filtering system 3200 also includes the anticoagulant circuit of FIG. 2. The effluent circuit comprises an anticoagulant line 3242 fluidly connected to an anticoagulant reservoir 3240 and configured to be connected to the blood circuit. In some embodiments, the anticoagulant reservoir 3240 can be its own anticoagulant pump as the anticoagulant reservoir 3240 comprises a syringe. In some such embodiments, the syringe can be manually used to introduce anticoagulant into the blood circuit and can be referred to as a "manual pump." Alternatively, in some embodiments, the syringe can be pressed by a pump, piston, or other device that is automatic and can automatically introduce anticoagulant into the blood circuit. However, in some examples, the extracorporeal blood filtering system 3200 can include a separate anticoagulant pump 3241 configured to pump anticoagulant from the anticoagulant reservoir 3240 through the anticoagulant line 3242 into the blood circuit. As with the blood pump 3210, the effluent pump 3224, and the source fluid pump 3238, the anticoagulant pump 3241 can be in communication with the controller 3249 and can be controlled by the controller 3249.

Additionally, the extracorporeal blood filtering system 3200 can interact with an external device 3201. The external device 3201 can comprise a device that causes various kinds of fluid to flow into and/or out of the patient and can, in some examples, record an amount of fluid it causes to flow into or out of the patient. For example, the external device 3201 can include an infusion pump, a wound vacuum, and/or an extracorporeal membrane oxygenation machine. Fluids provided/received by external devices can include medications, electrolyte replacement fluid, nutritional fluid, albumin, anticoagulation fluid, and machines/receptacles that collect bodily fluids. The external device 3201 can also be in communication with the controller 3249 (e.g., wired or wireless communication) and can send external fluid inflow/outflow information to the controller 3249. The external fluid inflow/outflow information can comprise the amount of fluid the external device 3201 causes to flow into and/or out of the patient. In some embodiments, the extracorporeal blood filtering system 3200 includes multiple external devices that are in communication with the controller 3249 and can send external fluid inflow/outflow information.

Further, the extracorporeal blood filtering system 3200 can include a user interface which can be part of a user input device 3268 and/or a display 3244. For example, both the user input device 3268 and the display 3244 can be used as user interfaces and can receive one or more inputs from a user. Further, the user input device 3268 and the display 3244 can receive outputs from the controller 2949 and can, in some examples, display the output.

The extracorporeal blood filtering system 3200 can further interact with a pulse oximetry sensor 3255 that is configured to measure a blood oxygen saturation of a patient. The pulse oximetry sensor 3255 can be separate from the extracorporeal blood filtering machine 3202 and can be put on a patient's finger, for example. However, in some instances, the pulse oximetry sensor 3255 can be part of the extracorporeal blood filtering system 3200 and is in communication with the controller 3249. For example, the pulse oximetry sensor 3255 can provide the blood oxygen saturation it measures to the controller 3249. In some embodiments, the controller 3249 is configured to provide the blood oxygen saturation to the user interface (e.g., display 3244) for display. Additionally, in some embodiments, the controller 3249 can be configured to output an alarm signal to the user interface when the blood oxygen saturation measured by the pulse oximetry sensor is below an alarm threshold value (e.g., 88%).

Now referencing the controller 3249, the controller 3249 can be in communication with some or all components within the extracorporeal blood filtering system 3200 and can operate the extracorporeal blood filtering system 3200, including some or all aspects of the extracorporeal blood filtering machine 3202. For example, the controller 3249 is in communication with the extracorporeal blood filtering machine 3202 and is configured to operate the blood pump 3210, the effluent pump 3224, and the source fluid pump 3238 in order to filter a patient's blood.

The controller 3249 is configured to collect internal fluid inflow/outflow information related to fluid flowing into and out of a patient via the extracorporeal blood filtering machine 3202. The controller 3249 can collect the internal fluid inflow/outflow information through operation of the extracorporeal blood filtering machine 3202. For example, the controller 3249 can collect internal fluid outflow information from the effluent scale 3246, the effluent pump 3224, and/or from another effluent sensing device (e.g., flow sensors 2990, 2992 of FIG. 29) as the effluent is filtered out from a patient's blood. The fluid outflow information can thus comprise effluent flow information. Further, the controller 3249 can collect internal fluid inflow information from the source fluid scale 3248, the source fluid pump 3238, and/or from another source fluid sensing device (e.g., flow sensors 2994, 2996 of FIG. 29). The fluid inflow information can thus comprise source fluid flow information. Additionally, in some embodiments, the controller 3249 can collect internal fluid inflow information from the anticoagulant pump and/or other anticoagulant sensing device as anticoagulant is added to the blood circuit. The internal fluid inflow information can thus include anticoagulant flow information. In some embodiments, the internal fluid inflow/outflow information comprises blood flow information, which the controller 3249 can collect from the blood pump 3210 and/or other blood sensing device.

In some embodiments, the controller 3249 is also configured to receive external fluid inflow/outflow information related to fluid flowing into and out of a patient not via the extracorporeal blood filtering machine 3202. For example, the controller 3249 can receive the external inflow/outflow information from the external device 3201, which can produce the external fluid inflow/outflow information as it causes fluid to flow into and out of the patient. In some embodiments, the controller 3249 can receive the external inflow/outflow information by communicating directly with the external device 3201. Additionally or alternatively, in some embodiments, the controller 3249 can receive the external inflow/outflow information indirectly, such as through another device.

As described, the controller 3249 can collect the internal fluid inflow/outflow information and the external fluid inflow/outflow information automatically by communicating with various components. In some embodiments, the controller 3249 can receive the internal fluid inflow/outflow information and/or the external fluid inflow/outflow information via manual entry. For example, the controller 3249 can receive the external fluid inflow/outflow information by receiving manually entered external fluid inflow/outflow information. In some external inflow examples, a user can manually inject fluids, such as medications or diagnostic fluids, into the blood line or the patient directly and/or can hook the patient up to an IV. The amount of manually injected fluids can then be entered. In some external outflow examples, a user can manually enter an amount of output from chest tubes, wound or drainage bags, or the like. The manually entered fluid inflow/outflow information can be entered via one or more of the user input device 3268, the display 3244, or the external device 3201 itself.

The controller 3249 can be configured to determine a fluid inflow/outflow balance based on the internal fluid inflow/outflow information and the external fluid inflow/outflow information. The controller 3249 can further provide the fluid inflow/outflow balance information to the user interface (e.g., 3244) for display. The fluid inflow/outflow balance can comprise the net fluid inflow vs. fluid outflow from both internal and external sources. The fluid inflow/outflow balance can be displayed as the net fluid inflow vs. fluid outflow (e.g., a single positive or negative number) and/or as the gross fluid inflow vs. the gross fluid outflow (e.g., total fluid inflow and total fluid outflow). In some embodiments, the controller 3249 is configured to determine the fluid inflow/outflow balance information based in part on the blood oxygen saturation measured by the pulse oximetry sensor 3255. For example, a lower blood oxygen saturation may indicate an overload of fluid within a patient's body.

In some embodiments, the controller 3249 can be configured to collect the internal fluid inflow/outflow information, receive the external fluid inflow/outflow information, determine the fluid inflow/outflow balance information, and provide the fluid inflow/outflow balance information to the user interface for display all dynamically in real time. This can be advantageous as a user can quickly determine multiple facets of fluid inflow and fluid outflow for a patient by viewing the user interface and can take steps to make appropriate adjustments as necessary.

Figure 33:
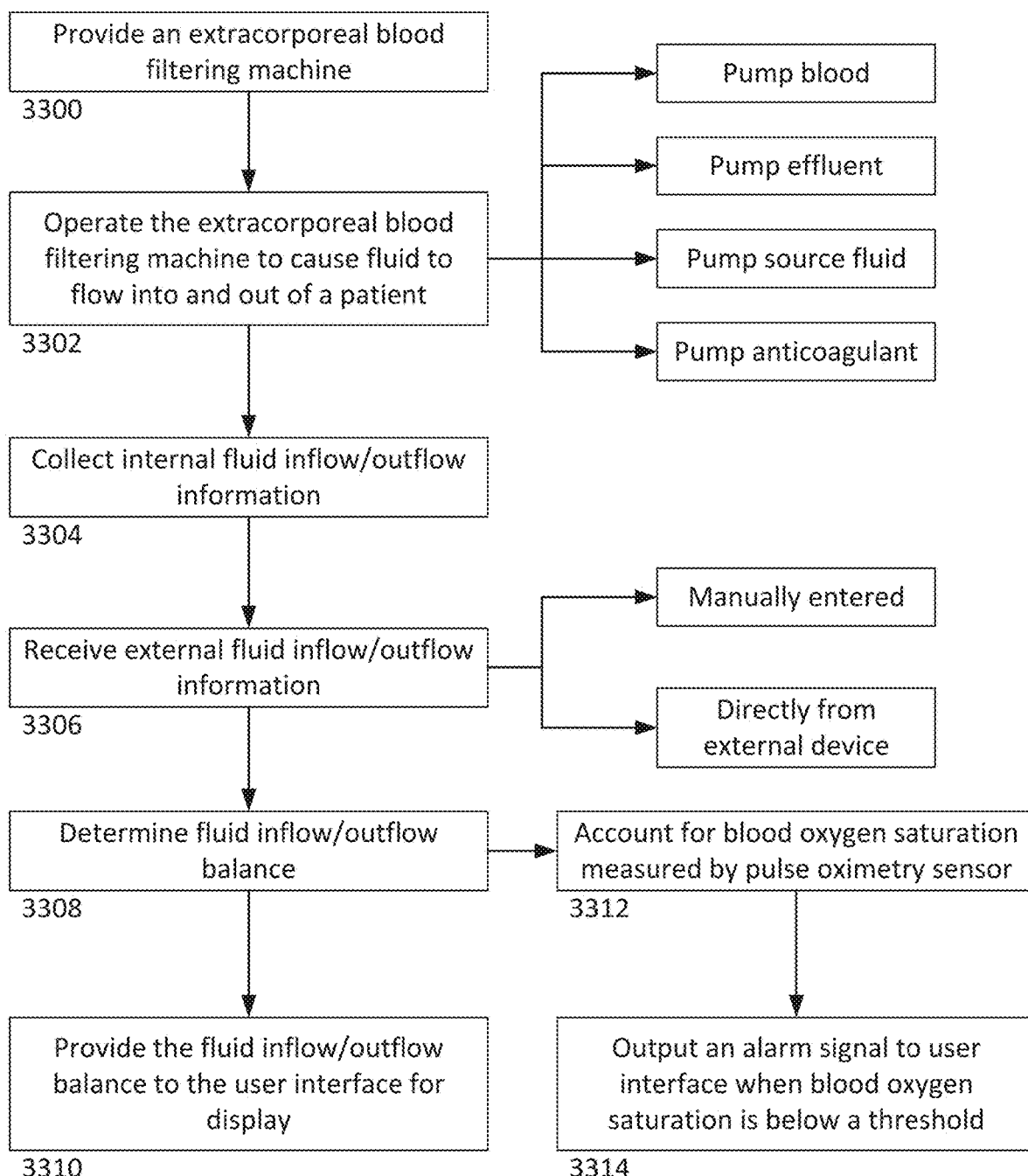
FIG. 33 is a flowchart of an example method of operating the extracorporeal blood filtering machine of FIG. 32 according to an aspect of the present disclosure.

Moving to FIG. 33, FIG. 33 is a flowchart of an example method of operating the extracorporeal blood filtering machine of FIG. 32 according to an aspect of the present disclosure. The method starts at step 3300, which includes providing an extracorporeal blood filtering machine. In some embodiments, the extracorporeal blood filtering machine can simply comprise a user interface and a controller. However, in some embodiments, the extracorporeal blood filtering machine can comprise other elements such as a blood circuit, an effluent circuit, a source fluid circuit, and an anticoagulant circuit.

The method continues at steps 3302 and 3304. Step 3302 includes operating the extracorporeal blood filtering machine with the controller to cause fluid to flow into and out of a patient, while step 3304 includes collecting internal fluid inflow/outflow information by the controller. The internal fluid inflow/outflow information can be related to the fluid flowing into and out of the patient through operation of the extracorporeal blood filtering machine. For example, the internal fluid inflow/outflow information can comprise blood flow information, effluent flow information, source fluid flow information, and/or anticoagulant flow information.

Next, in step 3306, the method includes receiving external fluid inflow/outflow information by the controller. In similarity with the internal fluid inflow/outflow information, the external fluid inflow/outflow information can be related to fluid flowing into and out of the patient other than through operation of the extracorporeal blood filtering machine (e.g., via an external device). In some examples, the receiving external fluid inflow/outflow information by the controller includes receiving manually entered external fluid inflow/outflow information by the controller. Additionally or alternatively, in some examples, receiving external fluid inflow/outflow information by the controller includes communicating directly with an external device that causes fluid to flow into or out of the patient.

The method further continues with step 3308 and step 3310. In step 3308, the method includes determining fluid inflow/outflow balance information by the controller based on the internal fluid inflow/outflow information and the external fluid inflow/outflow information. In step 3310, the method includes providing the fluid inflow/outflow balance information by the controller to the user interface for display.

In some embodiments, providing the extracorporeal blood filtering machine in step 3300 includes providing a pulse oximetry sensor configured to measure a blood oxygen saturation of a patient. In some such embodiments, the step of determining fluid inflow/outflow balance information includes accounting for blood oxygen saturation measured by the pulse oximetry sensor as in step 3312. Further, in some embodiments, the method can include outputting an alarm signal to the user interface when the blood oxygen saturation measured by the pulse oximetry sensor is below an alarm threshold value as in step 3314.

While the steps of FIG. 33 may be illustrated and discussed in a particular order, it will be appreciated that the steps of FIG. 33 need not be performed in the illustrated or described order. For instance, in some examples, method steps illustrated as occurring after other methods steps can, in actuality, occur before the other method steps. Further, some steps can be performed substantially simultaneously as other steps, while some steps can be performed any amount of time after other steps.

There are several advantages of the extracorporeal blood filtering machine of FIG. 32 and the associated method of FIG. 33. For example, although an extracorporeal blood filtering machine can ensure balance between the fluid it causes to flow into and out of a patient, it can be important to achieve overall fluid balance, accounting for fluid flowing into and out of the patient via various devices. Conventional methods of tracking such overall balance involve manually entering both internal and external fluid inflow/outflow information into a spreadsheet via a computer that is separate from the extracorporeal blood filtering machine. There are advantages to automatically capturing some or all of the fluid inflow/outflow information, and there are advantages to providing a user-friendly user interface for allowing manual entry of fluid inflow/outflow information and display of the overall fluid balance.

Figure 34:
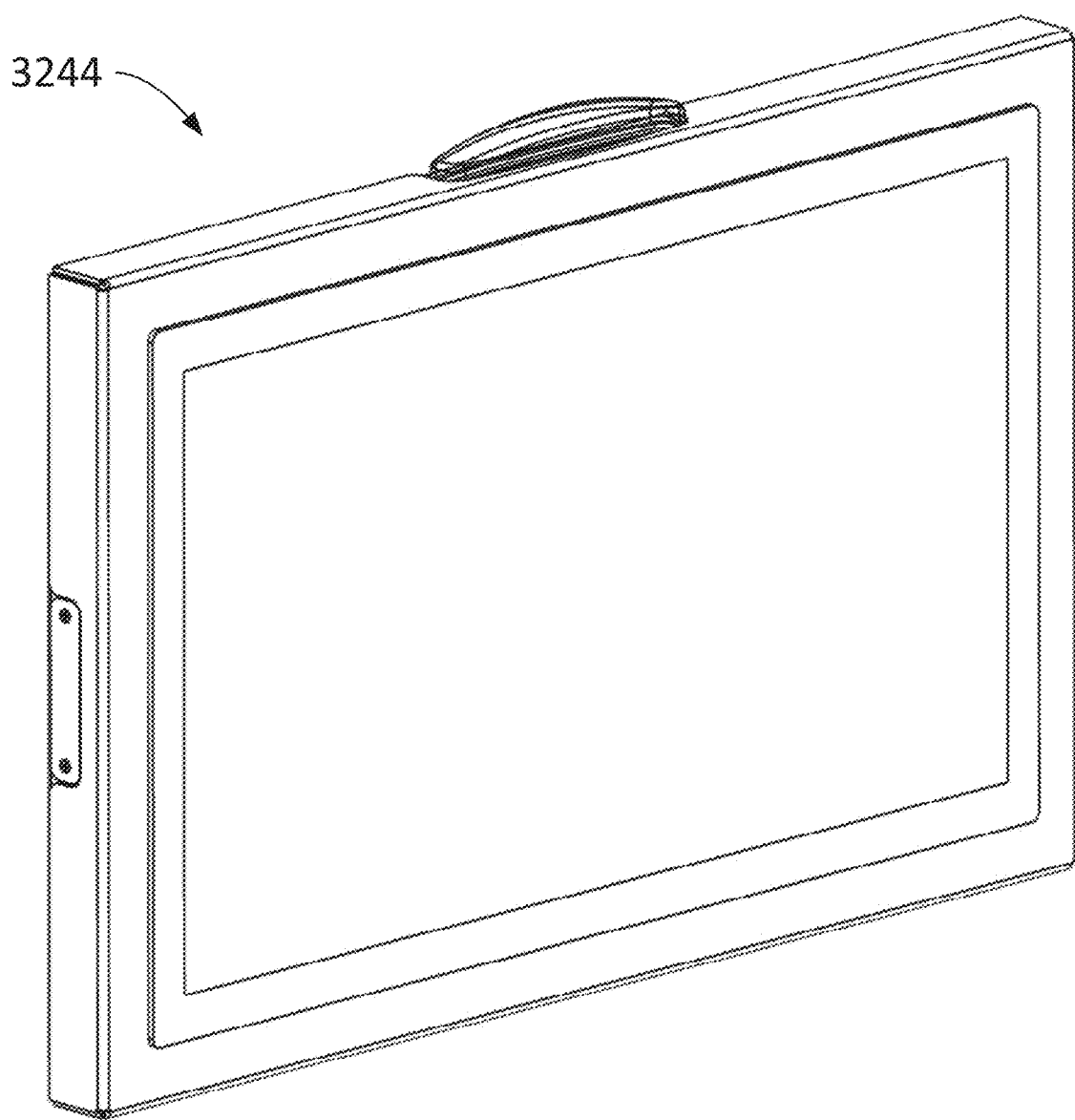
FIG. 34 is a perspective view of an example display according to an aspect of the present disclosure.

Moving to FIG. 34, FIG. 34 is a perspective view of an example display 3444 according to an aspect of the present disclosure. The display 3444 can be any type of display, but in some examples, includes a touch-enabled display. The display 3444 can also be considered a user interface or user input device and receive user inputs. As discussed elsewhere herein, the display 3444 can be in communication with a controller (e.g., 3249) and can display outputs received from the controller.

Various embodiments have been described. Such examples are non-limiting, and do not define or limit the scope of the invention in any way.

The invention claimed is:
1. An extracorporeal blood filtering machine comprising:
 a blood circuit that includes:
  a blood line comprising a blood inlet configured to receive blood from a patient and a blood outlet configured to return the blood to the patient,
  a filter fluidly connected to the blood line between the blood inlet and the blood outlet, and a blood pump configured to pump the blood from the blood inlet to the blood outlet through the filter, the filter configured to remove waste from the blood;
an effluent circuit that includes:
an effluent line fluidly connected to the filter, the effluent line configured to receive the waste from the filter in the form of effluent, and
an effluent pump configured to pump the effluent from the filter through the effluent line into an effluent receptacle;
a hemolysis sensor configured to sample the effluent in the effluent line and/or the blood in the blood line and output a hemolysis signal indicative of a detected degree of hemolysis; and
a controller in communication with the blood pump, the effluent pump, and the hemolysis sensor, the controller configured to receive the hemolysis signal and to output a hemolysis alert signal if the detected degree of hemolysis exceeds a hemolysis threshold.

2. The extracorporeal blood filtering machine of claim 1, wherein the hemolysis sensor is in optical communication with the effluent line and is configured to sample the effluent in the effluent line.

3. The extracorporeal blood filtering machine of claim 1, wherein the hemolysis sensor is fluidly connected to the blood line and configured to sample the blood in the blood line.

4. The extracorporeal blood filtering machine of claim 1, further comprising a display in communication with the controller, wherein the display is configured to receive the hemolysis alert signal from the controller and display a hemolysis alert.

5. The extracorporeal blood filtering machine of claim 1, further comprising a blood leak detector configured to detect a presence of blood within the effluent line, wherein the controller is in communication with the blood leak detector and is configured to output a blood leak alarm signal if the blood leak detector detects the presence of blood within the effluent line.

6. The extracorporeal blood filtering machine of claim 5, wherein the controller is further configured to stop the effluent pump if the blood leak detector detects the presence of blood within the effluent line.

7. The extracorporeal blood filtering machine of claim 1, wherein the hemolysis sensor is configured to sample the effluent in the effluent line and/or the blood in the blood line between the blood pump and the blood outlet.

8. The extracorporeal blood filtering machine of claim 7, further comprising a reference hemolysis sensor in communication with the controller and configured to sample the blood in the blood line between the blood inlet and the blood pump and to output a reference hemolysis signal indicative of a reference degree of hemolysis.

9. The extracorporeal blood filtering machine of claim 8, wherein the controller is configured to:
receive the reference hemolysis signal,
compare the reference hemolysis signal to the hemolysis signal, and
output a hemolysis mismatch alert signal if the hemolysis signal differs from the reference hemolysis signal by more than a threshold amount.

10. The extracorporeal blood filtering machine of claim 9, further comprising a display in communication with the controller, wherein the display is configured to receive the hemolysis mismatch alert signal from the controller and display a blood pump hemolysis alert.

11. A method comprising:
providing an extracorporeal blood filtering machine that includes:
a blood circuit that includes:
a blood line comprising a blood inlet and a blood outlet,
a filter fluidly connected to the blood line between the blood inlet and the blood outlet, and
a blood pump;
an effluent circuit that includes:
an effluent line fluidly connected to the filter, and
an effluent pump;
a hemolysis sensor; and
a controller in communication with the blood pump, the effluent pump, and the hemolysis sensor;
operating the extracorporeal blood filtering machine by the controller to:
pump blood with the blood pump from a patient into the blood inlet through the blood line to the filter and back to the patient through the blood line out of the blood outlet, the filter removing waste from the blood and providing the waste to the effluent line in the form of effluent, and
pump the effluent with the effluent pump through the effluent line into an effluent receptacle;
sampling the effluent in the effluent line and/or the blood in the blood line with the hemolysis sensor;
providing a hemolysis signal indicative of a detected degree of hemolysis from the hemolysis sensor to the controller; and
outputting a hemolysis alert signal with the controller if the detected degree of hemolysis exceeds a hemolysis threshold.

12. The method of claim 11, wherein sampling the effluent in the effluent line and/or the blood in the blood line with the hemolysis sensor comprises sampling the effluent in the effluent line with the hemolysis sensor.

13. The method of claim 11, wherein sampling the effluent in the effluent line and/or the blood in the blood line with the hemolysis sensor comprises sampling the blood in the blood line with the hemolysis sensor.

14. The method of claim 11, wherein:
the extracorporeal blood filtering machine further includes a display in communication with the controller, and
the method further comprises the display receiving the hemolysis alert signal from the controller and displaying a hemolysis alert.

15. The method of claim 11, wherein sampling the effluent in the effluent line and/or the blood in the blood line with the hemolysis sensor comprises sampling the effluent in the effluent line and/or the blood in the blood line between the blood pump and the blood outlet.

16. The method of claim 15, wherein:
the extracorporeal blood filtering machine further includes a reference hemolysis sensor in communication with the controller,
the method further comprises:
sampling the blood in the blood line between the blood inlet and the blood pump with the reference hemolysis sensor,
providing a reference hemolysis signal indicative of a reference degree of hemolysis from the reference hemolysis sensor to the controller,
comparing the reference hemolysis signal to the hemolysis signal with the controller, and outputting a hemolysis mismatch alert signal with the controller if the hemolysis signal differs from the reference hemolysis signal by more than a threshold amount.

17. The method of claim 16, wherein:

the extracorporeal blood filtering machine further includes a display in communication with the controller, the method further comprises:

provide the hemolysis mismatch alert signal from the controller to the display, and displaying a blood pump hemolysis alert on the display.

* * * * *